(12) United States Patent
Wittwer et al.

(10) Patent No.: US 7,670,832 B2
(45) Date of Patent: Mar. 2, 2010

(54) SYSTEM FOR FLUORESCENCE MONITORING

(75) Inventors: Carl T. Wittwer, Salt Lake City, UT (US); Kirk M. Ririe, Salt Lake City, UT (US)

(73) Assignees: University of Utah Research Foundation, Salt Lake City, UT (US); Idaho Technology, Inc., Salt Lake City, UT (US)

( * ) Notice: Subject to any disclaimer, the term of this patent is extended or adjusted under 35 U.S.C. 154(b) by 361 days.

(21) Appl. No.: 11/203,947

(22) Filed: Aug. 15, 2005

(65) Prior Publication Data

US 2006/0029965 A1     Feb. 9, 2006

Related U.S. Application Data

(60) Continuation of application No. 10/397,759, filed on Mar. 26, 2003, now Pat. No. 7,160,998, which is a continuation of application No. 09/799,160, filed on Mar. 5, 2001, now Pat. No. 6,569,627, which is a continuation of application No. 09/635,344, filed on Aug. 9, 2000, now Pat. No. 6,232,079, which is a division of application No. 08/869,276, filed on Jun. 4, 1997, now Pat. No. 6,174,670, which is a continuation-in-part of application No. 08/818,267, filed on Mar. 17, 1997, now abandoned, which is a continuation-in-part of application No. 08/658,993, filed on Jun. 4, 1996, now abandoned.

(51) Int. Cl.
*C12M 1/00* (2006.01)
*C12Q 1/68* (2006.01)

(52) U.S. Cl. ........................ 435/283.1; 435/6

(58) Field of Classification Search ........................ None
See application file for complete search history.

(56) References Cited

U.S. PATENT DOCUMENTS

| | | | |
|---|---|---|---|
| 1,006,767 A | 10/1911 | Mauger | |
| 1,456,005 A | 5/1923 | Harris | |
| 2,379,474 A | 7/1945 | Bramson | |
| 3,219,416 A | 11/1965 | Natelson | |
| 3,556,659 A | 1/1971 | Hawes | |
| 3,616,264 A | 10/1971 | Ray et al. | |
| 4,038,055 A | 7/1977 | Varano et al. | |
| 4,168,017 A | 9/1979 | Anderwald | |
| 4,286,456 A | 9/1981 | Sisti et al. | |
| 4,420,679 A | 12/1983 | Howe | |
| 4,468,423 A | 8/1984 | Hall | |
| 4,481,405 A | 11/1984 | Malick | |
| 4,599,169 A | 7/1986 | Ray | |
| 4,675,300 A | 6/1987 | Zare et al. | |
| 4,683,195 A | 7/1987 | Mullis et al. | |
| 4,683,202 A * | 7/1987 | Mullis ........................ | 435/91.2 |
| 4,684,465 A | 8/1987 | Leaseburge et al. | |
| 4,701,415 A | 10/1987 | Dutton et al. | |
| 4,708,782 A | 11/1987 | Andresen et al. | |
| 4,865,986 A | 9/1989 | Coy et al. | |
| 4,868,103 A | 9/1989 | Stavrianopoulos et al. | |
| 4,889,818 A | 12/1989 | Gelfand et al. | |
| 4,902,624 A | 2/1990 | Columbus et al. | |
| 4,908,112 A | 3/1990 | Pace | |
| 4,965,188 A | 10/1990 | Mullis et al. | |
| 4,981,801 A | 1/1991 | Suzuki et al. | |
| 5,038,852 A | 8/1991 | Johnson et al. | |
| 5,114,551 A | 5/1992 | Hjerten et al. | |
| 5,116,471 A | 5/1992 | Chien et al. | |
| 5,131,998 A | 7/1992 | Jorgenson et al. | |
| 5,137,695 A | 8/1992 | Rusnak et al. | |
| 5,141,621 A | 8/1992 | Zare et al. | |
| 5,169,511 A | 12/1992 | Allington et al. | |
| 5,169,521 A | 12/1992 | Oka et al. | |
| 5,173,163 A | 12/1992 | Tehrani | |
| 5,187,084 A | 2/1993 | Hallsby | |
| 5,207,987 A * | 5/1993 | Kureshy et al. ............... | 422/67 |
| 5,210,015 A | 5/1993 | Gelfand et al. | |
| 5,234,586 A | 8/1993 | Afeyan et al. | |

(Continued)

FOREIGN PATENT DOCUMENTS

| | | |
|---|---|---|
| AU | 528259 | 4/1983 |
| DE | 3 808 942 A1 | 9/1989 |
| EP | 0 229 943 A2 | 1/1985 |
| EP | 0 171 140 A2 | 2/1986 |
| EP | 0 211 334 A1 | 2/1987 |
| EP | 0 236 069 A2 | 2/1987 |
| EP | 232967 A2 * | 8/1987 |
| EP | 0 318 255 | 5/1989 |
| EP | 0 404 258 | 12/1990 |
| EP | 0 459 241 A1 | 5/1991 |

(Continued)

OTHER PUBLICATIONS

Higuchi et al. ("Simultaneous amplification and detection of specific DNA sequences" Biotechnology (N Y). Apr. 1992;10(4):413-7).*

(Continued)

*Primary Examiner*—Christopher M. Babic
(74) *Attorney, Agent, or Firm*—Homer W. Faucett, III; Ice Miller LLP

(57) ABSTRACT

The present invention is directed to devices for performing PCR and monitoring the reaction of a sample comprising a nucleic acid and a fluorescent dye. Illustrative devices comprise a heat exchange component for heating and cooling the sample, a control device for repeatedly operating the heat exchange component to subject the sample to thermal cycling, an excitation source for optically exciting the sample to cause the sample to fluoresce, a photodetector for detecting temperature-dependent fluorescence levels from the sample, and a processor configured to record and process emissions from the fluorescent dye.

14 Claims, 53 Drawing Sheets

U.S. PATENT DOCUMENTS

| | | | |
|---|---|---|---|
| 5,240,577 A | 8/1993 | Jorgenson et al. | |
| 5,316,913 A | 5/1994 | Butcher et al. | |
| 5,333,675 A | 8/1994 | Mullis et al. | |
| 5,346,672 A | 9/1994 | Stapleton et al. | |
| 5,348,853 A | 9/1994 | Wang et al. | |
| 5,364,790 A | 11/1994 | Atwood et al. | |
| 5,380,489 A | 1/1995 | Sutton et al. | |
| 5,415,839 A * | 5/1995 | Zaun et al. | 422/64 |
| 5,425,921 A | 6/1995 | Coakley et al. | |
| 5,436,134 A | 7/1995 | Haugland et al. | |
| 5,449,621 A | 9/1995 | Klein | |
| 5,455,175 A | 10/1995 | Wittwer et al. | |
| 5,563,037 A | 10/1996 | Sutherland et al. | |
| 5,565,322 A | 10/1996 | Heller | |
| 5,573,906 A | 11/1996 | Bannwarth et al. | |
| 5,585,242 A | 12/1996 | Bouma et al. | |
| 5,599,504 A | 2/1997 | Hoso et al. | |
| 5,789,173 A | 8/1998 | Peck et al. | |
| 5,804,380 A | 9/1998 | Harley et al. | |
| 5,863,726 A | 1/1999 | Harley et al. | |
| 5,871,908 A | 2/1999 | Henco et al. | |
| 5,891,639 A | 4/1999 | Harley et al. | |
| 5,925,517 A * | 7/1999 | Tyagi et al. | 435/6 |
| 6,106,777 A * | 8/2000 | Fujita et al. | 422/50 |
| 6,143,496 A | 11/2000 | Brown et al. | |
| 6,153,411 A | 11/2000 | Abaszadegan et al. | |

FOREIGN PATENT DOCUMENTS

| | | |
|---|---|---|
| EP | 0 475 760 A2 | 9/1991 |
| EP | 0 488 769 A2 | 11/1991 |
| EP | 0 519 623 A2 | 12/1992 |
| EP | 0 566 751 | 10/1993 |
| EP | 0 580 362 A1 | 1/1994 |
| EP | 0 640 828 A1 | 8/1994 |
| EP | 0 636 413 | 2/1995 |
| EP | 0 643 140 | 3/1995 |
| EP | 06040828 | 3/1995 |
| EP | 0 674 009 | 9/1995 |
| EP | 0 686 699 | 12/1995 |
| FR | 2 122 187 | 8/1972 |
| JP | 6 212 986 | 3/1987 |
| WO | WO 89 09437 | 10/1989 |
| WO | WO 92 20778 | 11/1992 |
| WO | WO9309128 | 5/1993 |
| WO | WO 95 13399 | 5/1995 |
| WO | WO 95/21266 | 8/1995 |
| WO | WO 95 21382 | 8/1995 |
| WO | WO 95 30139 | 11/1995 |
| WO | WO 95 32306 | 11/1995 |
| WO | WO 96 00901 | 1/1996 |
| WO | WO 96 06354 | 2/1996 |

OTHER PUBLICATIONS

Latimer et al. ("Ethidium bromide does not fluoresce when intercalated adjacent to 7-deazaguanine in duplex DNA" J Biol Chem. Jul. 25, 1991;266(21):13849-51).*

Schneeberger et al. ("Quantitative detection of reverse transcriptase-PCR products by means of a novel and sensitive DNA stain"PCR Methods Appl. Feb. 1995;4(4):234-8.*

Schneeberger et al. ("Quantitative detection of reverse transcriptase-PCR products by means of a novel and sensitive DNA stain"PCR Methods Appl. Feb. 1995;4(4):234-8).*

Applied and Environmental Microbiology, 1996, vol. 62, No. 5, pp. 1649-1655.

Nucleic Acids Research, 1994, vol. 22, No. 20, pp. 4321-4325.

Barnes, W.M., "PCR Amplification of up to 35-kb DNA with High Fidelity and High Yield from * Bacteriophage Templates," Proc. Natl. Acad. Sci. USA, vol. 91, pp. 2216-2220 (1994).

Brown, A.B., et al., "Rapid Cycle Amplification For Construction of Competititve Templates," Genetic Engineering with PCR, Edited by: Horton, R.M., Horizon Scientific Press, Wymondam, U. K., Chap. 4 (1997).

Cao, T.M., "A Simple and Inexpensive System to Amplify DNA by PCR," BioTechniques, vol. 7, No. 6, pp. 566-567 (1989).

Cardullo, R.A., et al., "Detection of Nucelic Acid Hybridization by Nonradiative Fluorescence Resonance Energy Transfer," Proc. Natl. Acad. Sci. USA, vol. 85, pp. 8790-8794 (1988).

Cotton, R.G.H., "Detection of Single Base Changes in Nucleic Acids," The Biochemical Journal, vol. 263, pp. 1-10, Oct. 1, 1989.

Denton, P., et al., "A Low-Cost Air-Driven Cycling Oven," PCR Protocols: A Guide to Methods and Applications, Edited by M.A. Innis, et al, Academic Press, Inc., San Diego, Chap. 52, pp. 435-441 (1990).

Findlay, J.B., et al., "Automated Closed-Vessel System for in Vitro Diagnostics Based on Polymerase Chain Reaction," Clinical Chemistry, vol. 39, No. 9, pp. 1927-1933 (1993).

Ghosh, S.S., et al., "Real Time Kinetics of Reduction Endonuclease Cleavage Monitored by Fluorescence Resonance Energy Transfer," Nucleic Acids Research, vol. 22, No. 15, pp. 3155-3159 (1994).

Goldner, H., "PCR update: New Techniques Multiply Uses," R&D Magazine, vol. 36, No. 4, p. 55 (Mar. 1994).

Graham, A., "A Haystack of Needles: Applying the Polymerase Chain Reaction," Chemistry and Industry, No. 18, p. 718 (Sep. 19, 1994).

Gustafson, E.C., et al. "Effect of Heat Denaturation of Target DNA on the PCR Amplification," Gene, vol. 123, pp. 241-244 (1993).

Higuchi, R., et al., "Simultaneous Amplification and Detection fo Specific DNA Sequences," Bio/Technology, vol. 10, pp. 413-417 (1992).

Higuchi, R., et al., "Kinetic PCR Analysis: Real-time Monitoring of DNA Amplification Reactions," Bio/Technology, vol. 11, pp. 1026-1030 (1993).

Hillen, W., et al., "High Resolution Experimental and Theoretical Thermal Denaturation Studies on Small Overlapping Restriction Fragments Containing the *Escherichia coli* Lactose Genectic Control Region," The Journal of Biological Chemistry, vol. 256, No. 6, pp. 2761-2766 (1981).

Hiyoshi, M., et al., "Assay of DNA Denaturation by Polymerase Chain Reaction-Driven Fluorescence Resonance Energy Transfer," Analytical Biochemistry, vol. 221, pp. 306-311 (1994).

Hoffman, L.M., et al., "Use of a Gas Chromatograph Oven for DNA Amplification by the Polymerase Chain Reaction," BioTechniques, vol. 6, No. 10, pp. 923-936 (1988).

Holland, P.M., et al., "Detection of Specific Polymerase Chain Reaction Product by Utilizing the 5**3* Exonuclease Activity of Thermus Aquaticus DNA Polymerase," Proc. Natl. Acad. Sci. USA, vol. 88, pp. 7276-7280 (1991).

Hopfenbeck, J.A., et al., "Digoxigenin-Labeled Probes Amplified from Genomic DNA Detect T-Cell Gene Rearrangements," American Journal of Clinical Pathology, vol. 97, No. 5, pp. 638-644 (1992).

Ishiguro, T., et al. "Homogeneous Quantitative Assay of Hepatitis C Virus RNA by Polymerase Chain Reaction in the Presence of a Fluorescent Intercalater," Analytical Biochemistry, vol. 229, pp. 207-213 (1995).

Kang, J., et al, "Exact Quantification of DNA-RNA Copy Numbers by PCR-TGGE," PCR Strategies, Academic Press, Inc., Chap. 15, pp. 189-198 (1995).

Ke, S., et al., "Influence of Nearest Neighbor Sequence on the Stability of Base Pair Mismatches in Long DNA: Determined by Temperature-Gradient Gel Electrophoresis," Nucelic Acids Research, vol. 21, No. 22, pp. 5137-5143 (1993).

Lee, L.G., et al., "Allelic Discrimination by Nick-Translation PCR with Fluorogenic Probes," Nucleic Acids Research, vol. 21, No. 16, pp. 3761-3766 (1993).

Linz, U., "Thermocycler Temperature Variation Invalidates PCR Results," Biotechniques, vol. 9, No. 3, pp. 286-290 (1990).

Livak, K.J., et al., "Oligonucleotides with Flourescent Dyes at Opposite Ends Provide a Quenched Probe System Useful for Detecting PCR Product and Nucelic Acid Hybridization," PCR Methods and Applications, vol. 4, pp. 357-362 (1995).

Livak, K.J., "Quantitation of DNA/RNA Using Real-Time PCR Detection," Perkin-Elmer Applied Biosystems Report (1996).

Morrison, L.E., "Detection of Energy Transfer and Fluorescence Quenching," Nonisotopic DNA Probe Techniques, Edited by: Larry J. Kricka, Academic Press, Inc., San Diego, Chap. 13, pp. 311-352 (1992).

Morrison, L.E., et al., "Sensitive Fluorescence-Based Thermodynamic and Kinetic Measurements of DNA Hybridization in Solution," Biochemistry, vol. 32, pp. 3095-3104 (1993).

Nisson, P., et al., "Real-Time Monitoring of DNA Maniupluations Using Biosensor Technology," Analytic Biochemistry, vol. 224, pp. 400-408 (1995).

Oste, C.C., "PCR Instrumentation: Where Do We Stand?," The Polymerase Chain Reaction, Edited by Mullis, et al., Birkhauser, Boston, Chap. 14 (1994).

Perry, R.H., et al., "Heat Transmission by Radiation," Chemical Engineers' Handbook, 5th ed., McGraw Hill Book Co., New York, Chap. 10, pp. 48-56 (????).

Ririe, K.M., et al., "Product Differentiation by Analysis of DNA Melting Curves during the Polymerase Chain Reaction," Analytical Biochemistry, vol. 254, pp. 154-160 (1997).

Segal, G.H., et al., "Identification of Monclonal B-cell Populations by Rapid Cycle Polymerase Chain Reaction," The American Journal of Pathology, vol. 141, No. 6, pp. 1291-1297 (1992).

Service, R.E., "The Incredible Shrinking Laboratory: Microchips Allow Miniaturization of Analytical Laboratories," Science, vol. 268, No. 5207, pp. 26 (Apr. 7, 1995).

Stimpson, D.I., "Real-time Detection of DNA Hybridization and Melting on Oligonucleotide Arrays by Using Optical Wave Guides," Proc. Natl. Acad. Sci. USA, vol. 92, pp. 6379-6383 (1995).

Swerdlow, H., et al., "Fully Automated DNA Reaction and Analysis in a Fluidic Capillary Instrument," Anal. Chem., vol. 69, pp. 848-855 (1997).

Tombler, E.R., et al., "Spectrofluorometric Assay for Hybridization of Oligodeoxynucleotides Using Ethidum Dimer," BioTechniques, vol. 15, No. 6, pp. 1060-1064 (1993).

Tyagi, S., et al., "Molecular Beacons: Probes that Fluoresce upon Hybridization," Nature Biotechnology, vol. 14, pp. 303-308 (1996).

Weis, J.H., et al. "Detection of Rare mRNAs via Quantitative RT-PCR," Trends in Genetics, vol. 8, No. 8, pp. 263-264 (1992).

Wilding, et al., "PCR in Silicon Microstructure," Clinical Chemistry, vol. 40, No. 9, pp. 1815-1818, (1994).

Williard, H.H., et al., "Gas Chromatography," Instrumental Methods of Analysis, 6th ed., Wadsworth Publishing Co., Belmont, CA, Chap. 16, p. 454 (????).

Wittwer, C.T., et al., "Minimizing the Time Required for DNA Amplification by Efficient Heat Transfer to Small Samples," Analytical Biochemistry, vol. 186, pp. 328-331 (1990).

Wittwer, C.T., et al., "Automated Polymerase Chain Reaction in Capillary Tubes with Hot Air," Nucleic Acids Research, vol. 17, No. 11, pp. 4353-4357 (1989).

Wittwer, C.T., et al., "Rapid Cycle DNA Amplification: Time and Temperature Optimization," BioTechniques, vol. 10, No. 1, pp. 76-83 (1991).

Wittwer, C.T., et al., "Rapid Cycle Allele-Specific Amplification: Studies with the Cystic Fibrosis *F508 Locus," Clinical Chemistry, vol. 39, No. 5, pp. 804-809 (1993).

Wittwer, C.T., et al., "Rapid Cycle DNA Amplificiation," The Polymerase Chain Reaction, Edited by: Mullis, et al, Birkhauser, Boston, Chap. 15 (1994).

Wittwer, C.T., et al., "Continuous Fluorescence Monitoring of Rapid Cycle DNA Amplification," BioTechniques, vol. 22, pp. 130-138 (1997).

Wittwer, C.T., et al., "The LightCycler: A Microvolume Multisample Fluorimeter with Rapid Temperature Control," BioTechniques, vol. 22, pp. 176-181 (1997).

Wittwer, C.T., et al., "Fluorescence Monitoring of Rapid Cycle PCR for Quantification," Gene Quantification, Edited by: Ferre, F., Birkhauser, Boston (1997).

Yguerabide, J., et al., "Quantitative Fluorescence Method for Continuous Measurement of DNA Hybridization Kinetics Using a Fluorescent Intercalator," Analytical Biochemistry, vol. 228, pp. 208-220 (1995).

Biotherm Corporation Advertisement, BioOven (1991).

Ericomp Advertisement, Twinblock System (1991).

Techne Advertisement, PHC-1 Dri-Block (1988).

Hybaid Advertisement, Hybaid Heating and Cooling Block (1988).

Eppendorf Advertisement, Eppendorf MicroCycler (1988).

COY Advertisement, Tempcycler Model 50 Microtube Incubator (1991).

Idaho Technology Advertisement and Specification Sheets for 1605 Product (1991).

Perkin-Elmer Advertisement, ABI Prism 7700 Sequence Detection System (1991).

Clark, et al., "Cassettes Simplify Small-sample Dialysis," R&D Magazine, p. 31, Sep. 1995.

"Let the Microchip Fall Where Diagnostics Lies: Implications: A Diagnostic Revolution?," Genesis Report-Dx, vol. 4, No. 3 (1994).

"Let the Microchip Fall Where Diagnostics Lies: Implications: Affymetrix: DNA on a Chip," Genesis Report-Dx, vol. 4, No. 3 (1994).

"PCR Detection Blows Cover on Lyme Disease, Q Fever," Biotechnology Newswatch, vol. 10, No. 1 (Jan. 1, 1990).

Schoffner et al., "Chip PCR. I. Surface passivation of microfabricated silicon-glass chips or PCR," Nucleic Acids Research, vol. 24, No. 2, pp. 375-379, 1996.

Cheng et al., "Chip PCR. II. Investigation of different PCR amplification systems in microfabricated silicon-glass chips," Nucleic Acids Research, vol. 24, No. 2, pp. 380-385, 1996.

Operation manual for HP-5880A Gas Chromatograph.

Operation manual for the MIC 6000.

Landsorp, et al., Single Laser Three Color Immunofluorescence Staining Procedures Based on Energy Transfer Between Phycoerythrin and Cyanine 5, Cytometry 12: 723-730 (1991).

Becker, Andreas, et al., "A Quantitative Method of Determining Initial Amounts of DNA by Polymerase Chain Reaction Cycle Titration Using Digital lmagingin and a Novel DNA STain," Analytical Biochemistry, Article No. 0230, vol. 237, pp. 204-207 (1996).

Skeidsvoll, Jarle, et al., "Analysis of Double-Stranded DNA by Capillary Electrophoresis with Laser-Induced Fluorescence Detection Using the Monomeric Dye SYBR Green 1," Analytical Biochemistery, vol. 231, pp. 359-365 (1995).

Karlsen, Frank et al., "SYBR Green I DNA staining increases the detection sensitivity of viruses by polymerase chain reaction," Journal of Virological Methods 55, pp. 153-156 (1995).

Marie, Dominique, et al., "Application of the Novel Nucelic Acid Dyes YOYO-1, YO-PRO-1, and PicoGreen for Flow Cytrometric Analysis of Marine Prokaryotes," Applied and Environemental Microbiology, pp. 1649-1655 (May 1996).

* cited by examiner

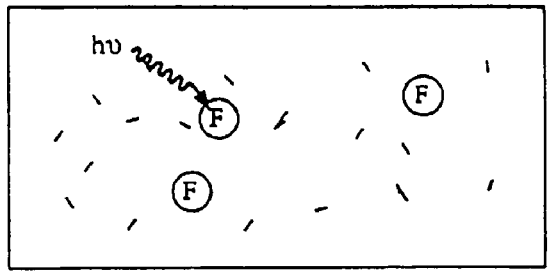 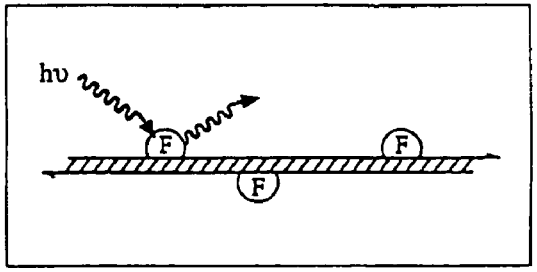
Fig. 5A(1)  Fig. 5A(2)
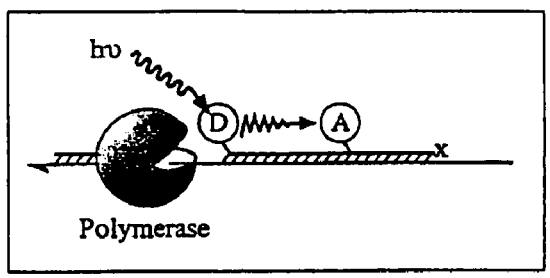 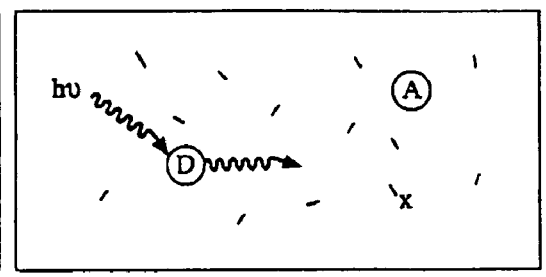
Fig. 5B(1)  Fig. 5B(2)
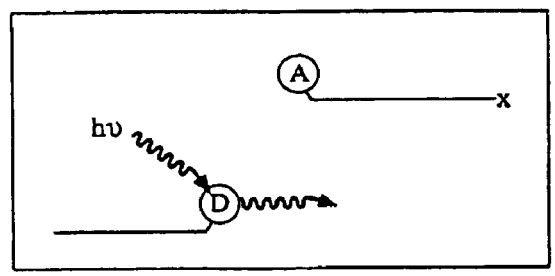 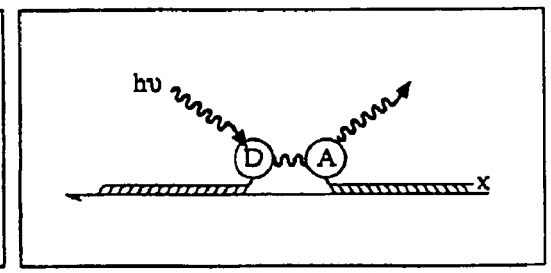
Fig. 5C(1)  Fig. 5C(2)

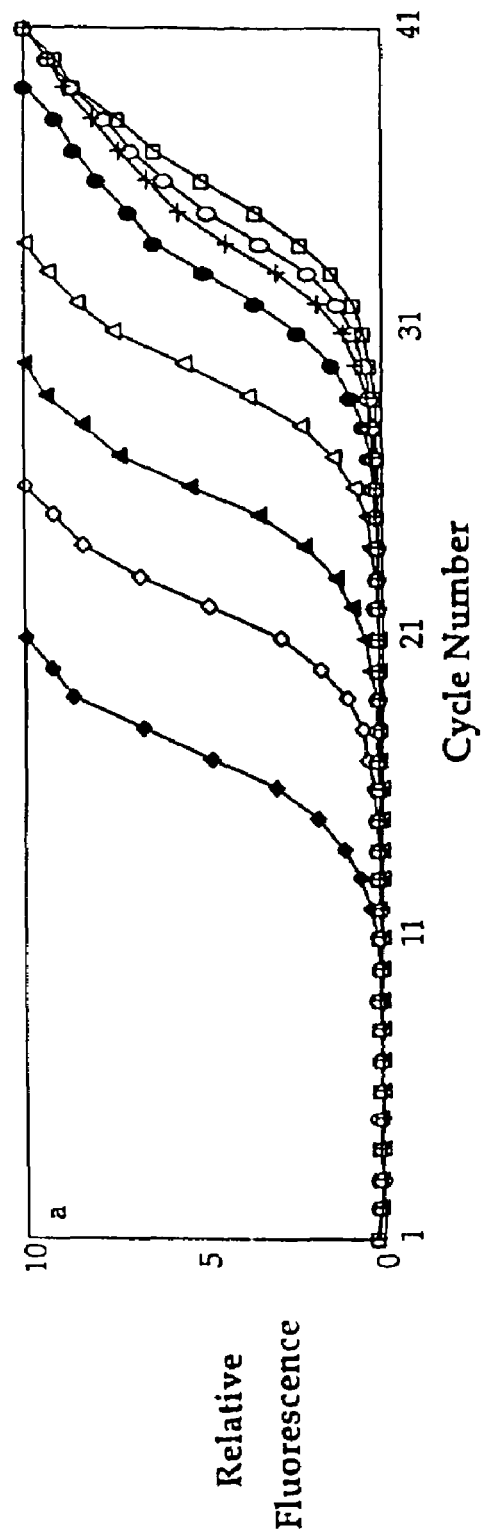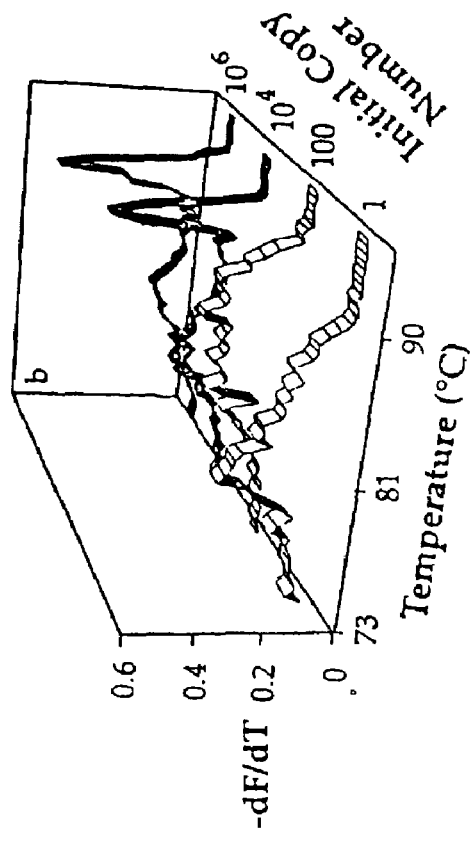
Fig. 42A
Fig. 42B

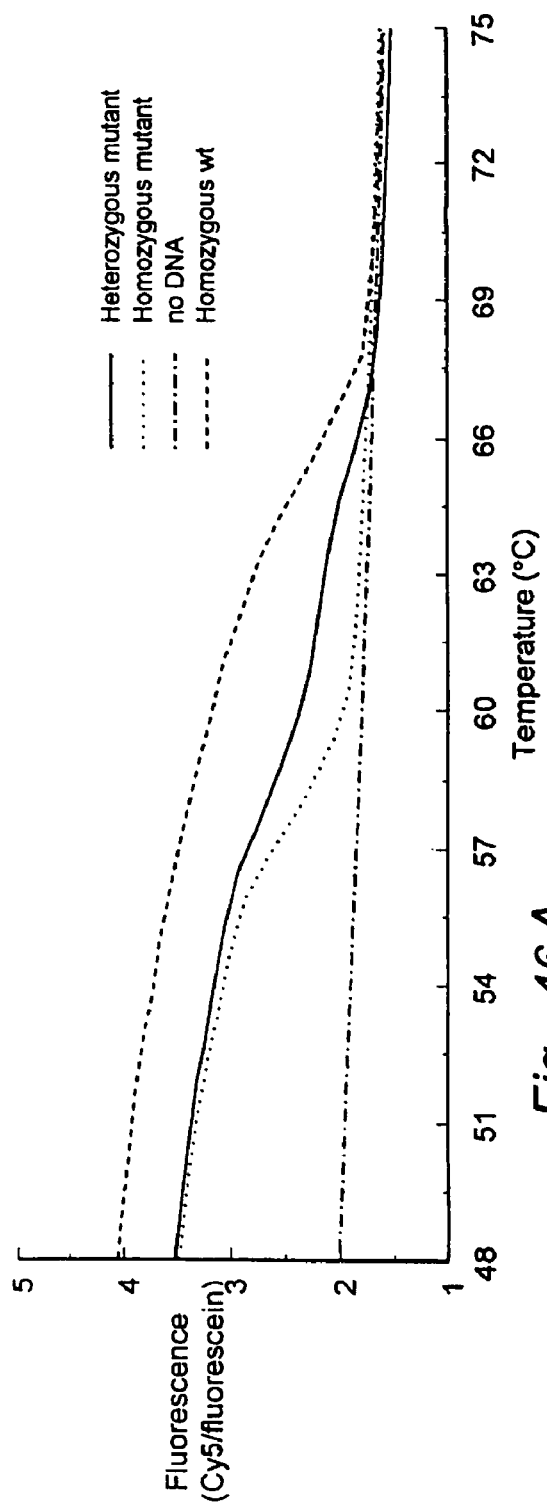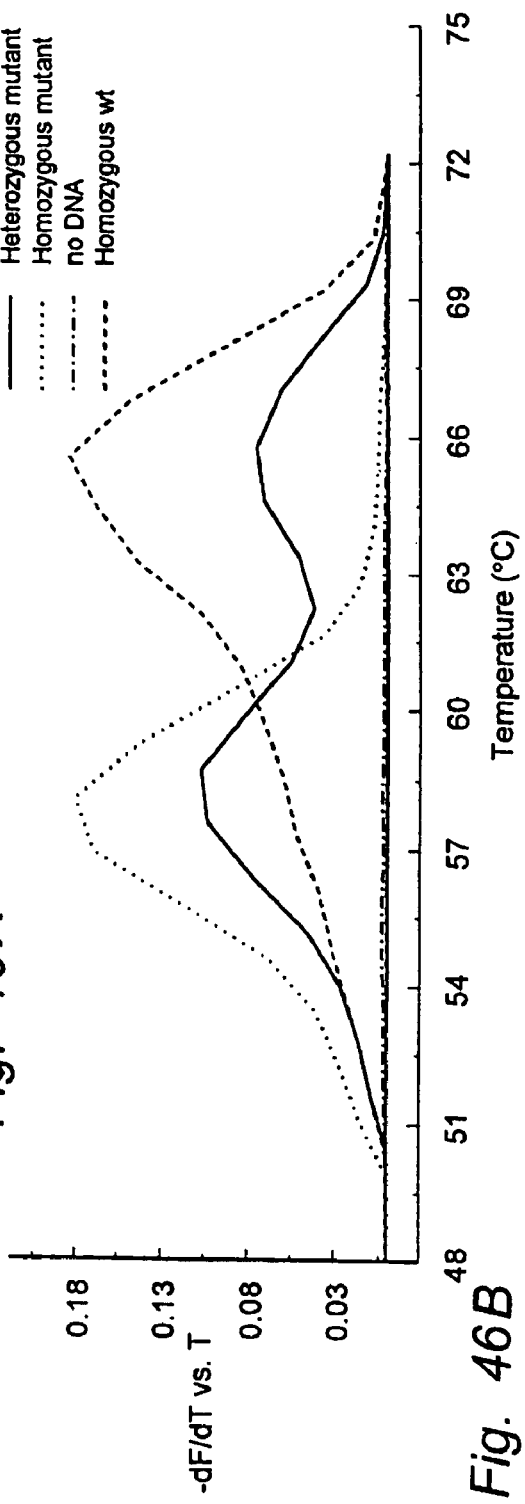
Fig. 46A
Fig. 46B

SYSTEM FOR FLUORESCENCE MONITORING

CROSS REFERENCE TO RELATED APPLICATIONS

This application is a continuation of U.S. application Ser. No. 10/397,759, filed Mar. 26, 2003 now U.S. Pat. No. 7,160, 998; which is a continuation of U.S. application Ser. No. 09/799,160, filed Mar. 5, 2001, now U.S. Pat. No. 6,569,627; which is a continuation of U.S. application Ser. No. 09/635, 344, filed Aug. 9, 2000, now U.S. Pat. No. 6,232,079; which is a divisional of U.S. application Ser. No. 08/869,276, filed Jun. 4, 1997, now U.S. Pat. No. 6,174,670; which is a continuation-in-part of U.S. application Ser. No. 08/818,267, filed Mar. 17, 1997 now abandoned; which is a continuation-in-part of U.S. patent application Ser. No. 08/658,993, filed Jun. 4, 1996, now abandoned. Each of the above-identified applications are now each individually incorporated herein by reference in their entireties.

MICROFICHE APPENDIX

A microfiche appendix is contained in U.S. application Ser. No. 08/869,276, herein incorporated by reference.

BACKGROUND OF THE INVENTION

This invention relates generally to observing fluorescence signals resulting from hybridization in conjunction with the polymerase chain reaction. More specifically, the present invention relates to observing hybridization with fluorescence during and/or immediately after PCR and using this information for product identification, sequence alteration detection, and quantification.

The polymerase chain reaction (PCR) is fundamental to molecular biology and is the first practical molecular technique for the clinical laboratory. Despite its usefulness and popularity, current understanding of PCR is not highly advanced. Adequate conditions for successful amplifications must be found by trial and error and optimization is empirical. Even those skilled in the art are required to utilize a powerful technique without a comprehensive or predictive theory of the process.

PCR is achieved by temperature cycling of the sample, causing DNA to denature (separate), specific primers to attach (anneal), and replication to occur (extend). One cycle of PCR is usually performed in 2 to 8 min, requiring 1 to 4 hours for a 30-cycle amplification. The sample temperature response in most PCR instrumentation is very slow compared to the times required for denaturation, annealing, and extension. The physical (denaturation and annealing) and enzymatic (extension) reactions in PCR occur very quickly. Amplification times for PCR can be reduced from hours to less than 15 min. Incorporated herein by reference in their entireties are each of the following individual applications, which disclose such a rapid cycling system: U.S. application Ser. No. 08/818,267, filed Mar. 17, 1997, entitled Method for Detecting the Factor V Leiden Mutation, which is a continuation-in-part of U.S. patent application Ser. No. 08/658,993, filed Jun. 4, 1996, entitled System And Method For Monitoring PCR Processes, which is a continuation-in-part of U.S. patent application Ser. No. 08/537,612, filed Oct. 2, 1995, entitled Method For Rapid Thermal Cycling of Biological Samples, which is a continuation-in-part of U.S. patent application Ser. No. 08/179,969, filed Jan. 10, 1994, (now U.S. Pat. No. 5,455,175), entitled Rapid Thermal Cycling Device, which is a continuation-in-part of U.S. patent application Ser. No. 07/815,966 filed Jan. 2, 1992, (now abandoned) entitled Rapid Thermal Cycling Device which is a continuation-in-part of U.S. patent application Ser. No. 07/534,029 filed Jun. 4, 1990, (now abandoned) entitled Automated Polymerase Chain Reaction Device. The copending U.S. application filed in the U.S. Patent and Trademark Office on Jun. 4, 1997, entitled System and Method for Carrying Out and Monitoring Biological Processes as Ser No. 08/869,275 and naming Carl T. Wittwer, Kirk M. Ririe, Randy P. Rasmussen, and David R. Hillyard as applicants, is also hereby incorporated by reference in its entirety. Rapid cycling techniques are made possible by the rapid temperature response and temperature homogeneity possible for samples in high surface area-to-volume sample containers such as capillary tubes. For further information, see also: C. T. Wittwer, G. B. Reed, and K. M. Ririe, Rapid cycle DNA amplification, in K. B. Mullis, F. Ferre, and R. A. Gibbs, The polymerase chain reaction, Birkhauser, Boston, 174-181, (1994). Improved temperature homogeneity allows the time and temperature requirements of PCR to be better defined and understood. Improved temperature homogeneity also increases the precision of any analytical technique used to monitor PCR during amplification.

Fluorimetry is a sensitive and versatile technique with many applications in molecular biology. Ethidium bromide has been used for many years to visualize the size distribution of nucleic acids separated by gel electrophoresis. The gel is usually transilluminated with ultraviolet light and the red fluorescence of double stranded nucleic acid observed. Specifically, ethidium bromide is commonly used to analyze the products of PCR after amplification is completed. Furthermore, EPA 0 640 828 A1 to Higuchi & Watson, hereby incorporated by reference, discloses using ethidium bromide during amplification to monitor the amount of double stranded DNA by measuring the fluorescence each cycle. The fluorescence intensity was noted to rise and fall inversely with temperature, was greatest at the annealing/extension temperature (50° C.), and least at the denaturation temperature (94° C.). Maximal fluorescence was acquired each cycle as a measure of DNA amount. The Higuchi & Watson application does not teach using fluorescence to monitor hybridization events, nor does it suggest acquiring fluorescence over different temperatures to follow the extent of hybridization. Moreover, Higuchi & Watson fails to teach or suggest using the temperature dependence of PCR product hybridization for identification or quantification of PCR products.

The Higuchi & Watson application, however, does mention using other fluorophores, including dual-labeled probe systems that generate fluorescence when hydrolyzed by the 5'-exonuclease activity of certain DNA polymerases, as disclosed in U.S. Pat. No. 5,210,015 to Gelfand et al. The fluorescence observed from these probes primarily depends on hydrolysis of the probe between its two fluorophores. The amount of PCR product is estimated by acquiring fluorescence once each cycle. Although hybridization of these probes appears necessary for hydrolysis to occur, the fluorescence signal primarily results from hydrolysis of the probes, not hybridization, wherein an oligonucleotide probe with fluorescent dyes at opposite ends thereof provides a quenched probe system useful for detecting PCR product and nucleic acid hybridization, K. J. Livak et al., 4 PCR Meth. Appl. 357-362 (1995). There is no suggestion of following the temperature dependence of probe hybridization with fluorescence to identify sequence alterations in PCR products.

The specific hybridization of nucleic acid to a complementary strand for identification has been exploited in many different formats. For example, after restriction enzyme digestion, genomic DNA can be size fractionated and hybridized to probes by Southern blotting. As another example, single base mutations can be detected by "dot blots" with allele-specific oligonucleotides. Usually, hybridization is performed for minutes to hours at a single temperature to achieve the necessary discrimination. Alternately, the extent of hybridization can be dynamically monitored while the temperature is changing by using fluorescence techniques. For example, fluorescence melting curves have been used to monitor hybridization. L. E. Morrison & L. M. Stols, Sensitive fluorescence-based thermodynamic and kinetic measurements of DNA hybridization in solution, 32 Biochemistry 3095-3104, 1993). The temperature scan rates are usually 10° C./hour or less, partly because of the high thermal mass of the fluorimeter cuvette.

Current methods for monitoring hybridization require a lot of time. If hybridization could be followed in seconds rather than hours, hybridization could be monitored during PCR amplification, even during rapid cycle PCR. The many uses of monitoring hybridization during PCR, as will be fully disclosed herein, include, product identification and quantification, sequence alteration detection, and automatic control of temperature cycling parameters by fluorescence feedback The prior art, as explained above, carries out temperature cycling slowly and empirically. When analysis of PCR products by hybridization is needed, additional time consuming steps are required. Thus, it would be a great advance in the art to provide methods for monitoring hybridization during PCR and analyzing the reaction while it is taking place, that is, during or immediately after temperature cycling without manipulation of the sample. By monitoring hybridization during PCR, the underlying principles that allow PCR to work can be followed and used to analyze and optimize the reaction during amplification.

BRIEF SUMMARY OF THE INVENTION

It is an object of the present invention to provide a double-strand-specific DNA dye for monitoring product hybridization during PCR.

It is another object of the invention to provide a system for identifying PCR-amplified products by their fluorescence melting curves.

It is also an object of the invention to provide a method for improving the sensitivity of PCR quantification with double-strand-specific DNA dyes.

It is still another objection of the invention for determining the amount of specific product amplified by PCR by melting curves to correct for nonspecific amplification detected with the double-strand-specific DNA dye.

It is a further object of the invention to provide a method of relative quantification of different PCR products with double-strand-specific dyes.

It is yet another object of the invention to provide a method of product quantification by the reannealing kinetics of the product in the presence of a double-strand-specific DNA dye.

It is a still further object of the invention to provide a novel resonance energy transfer pair to monitor primer and/or probe hybridization.

It is still another object of the invention to provide a method of product quantification by the reannealing kinetics of a probe to the product using a resonance energy transfer pair.

It is also an object of the present invention to provide a method to determine initial template copy number by following the fluorescence of a hybridization probe or probes each cycle during PCR amplification.

It is another object of the invention to provide a system for homogeneous detection of PCR products by resonance energy transfer between two labeled probes that hybridize internal to the PCR primers.

It is still another object of the invention to provide a system for homogeneous detection of PCR products by resonance energy transfer between one labeled primer and one labeled probe that hybridizes internal to the PCR primers.

It is yet another object of the invention to provide a system for detection of sequence alterations internal to PCR primers by resonance energy transfer and probe melting curves.

It is a further object of the invention to provide a system for relative quantification of different PCR products by probe melting curves.

It is yet another object of the invention to provide methods to determine the initial template copy number by curve fitting the fluorescence vs cycle number plot.

It is still another object of the invention to provide a system and method for performing PCR rapidly and also continuously monitoring the reaction and adjusting the reaction parameters while the reaction is ongoing.

It is another object of the invention to replace the nucleic acid probes by synthetic nucleic acid analogs or derivatives, e.g. by peptide nucleic acids (PNA), provided that they can also be labeled with fluorescent compounds.

These and other objects and advantages of the invention will become more fully apparent from the description and claims which follow, or may be learned by the practice of the invention.

The present invention particularly decreases the total time required for PCR amplification and analysis over prior art techniques while at the same time allowing the option of significantly increasing the quality of the reaction by optimizing amplification conditions.

The present invention provides methods and applications for continuous fluorescence monitoring of DNA amplification. Required instrumentation combines optical components with structures to provide rapid temperature cycling to continuously monitor DNA amplification by a variety of different fluorescence techniques. In one illustrative embodiment, fluorescence is acquired continuously from a single sample or alternately from multiple samples on a rotating carousel with all of the samples being simultaneously subjected to rapid thermal cycling. Further information on associated instrumentation can be found in the U.S. patent applications referenced above.

In accordance with one aspect of the present invention, fluorescence during DNA amplification was monitored by: 1) the double strand-specific dye SYBR Green I, and 2) resonance energy transfer of fluorescein to Cy5™ or Cy5.5™ with hybridization probes. Fluorescence data acquired once per cycle allow quantification of initial template copy number.

Furthermore, in contrast to measuring fluorescence once per cycle, embodiments of the present invention are disclosed which monitor temperature, time and fluorescence continuously throughout each cycle thus producing a 3-dimensional spiral. This 3-dimensional spiral can be reduced to temperature vs. time, fluorescence vs. time, and fluorescence vs. temperature plots. Fluorescence vs. temperature plots of the fluorescence from hybridization probes can be used to detect sequence alterations in the product. These sequence alterations may be natural, as in mutations or polymorphisms, or artificial, as in an engineered alternative template for quantitative PCR.

In accordance with another aspect of the present invention, fluorescence monitoring is used to acquire product melting curves during PCR by fluorescence monitoring with double-strand-specific DNA specific dyes. Plotting fluorescence as a function of temperature as the thermal cycler heats through the dissociation temperature of the product gives a PCR product melting curve. The shape and position of this DNA melting curve is a function of GC/AT ratio, length, and sequence, and can be used to differentiate amplification products separated by less than 2° C. in melting temperature. Desired products can be distinguished from undesired products, including primer dimers. Analysis of melting curves can be used to extend the dynamic range of quantitative PCR and to differentiate different products in multiplex amplification. Using double strand dyes, product denaturation, reannealing and extension can be followed within each cycle. Continuous monitoring of fluorescence allows acquisition of melting curves and product annealing curves during temperature cycling.

The present invention provides reagents and methods for rapid cycle PCR with combined amplification and analysis by fluorescence monitoring in under thirty minutes, more preferably in under fifteen minutes, and most preferably in under ten minutes.

A method for analyzing a target DNA sequence of a biological sample comprises amplifying the target sequence by polymerase chain reaction in the presence of two nucleic acid probes that hybridize to adjacent regions of the target sequence, one of the probes being labeled with an acceptor fluorophore and the other probe labeled with a donor fluorophore of a fluorescence energy transfer pair such that upon hybridization of the two probes with the target sequence, the donor and acceptor fluorophores are within 25 nucleotides of one another, the polymerase chain reaction comprising the steps of adding a thermostable polymerase and primers for the targeted nucleic acid sequence to the biological sample and thermally cycling the biological sample between at least a denaturation temperature and an elongation temperature;

exciting the biological sample with light at a wavelength absorbed by the donor fluorophore and detecting the emission from the fluorescence energy transfer pair.

A method for analyzing a target DNA sequence of a biological sample comprises amplifying the target sequence by polymerase chain reaction in the presence of two nucleic acid probes that hybridize to adjacent regions of the target sequence, one of the probes being labeled with an acceptor fluorophore and the other probe labeled with a donor fluorophore of a fluorescence energy transfer pair such that upon hybridization of the two probes with the target sequence, the donor and acceptor fluorophores are within 25 nucleotides of one another, the polymerase chain reaction comprising the steps of adding a thermostable polymerase and primers for the targeted nucleic acid sequence to the biological sample and thermally cycling the biological sample between at least a denaturation temperature and an elongation temperature;

exciting the sample with light at a wavelength absorbed by the donor fluorophore; and monitoring the temperature dependent fluorescence from the fluorescence energy transfer pair.

A method of real time monitoring of a polymerase chain reaction amplification of a target nucleic acid sequence in a biological sample comprises (a) adding to the biological sample an effective amount of two nucleic acid primers and a nucleic acid probe, wherein one of the primers and the probe are each labeled with one member of a fluorescence energy transfer pair comprising an acceptor fluorophore and a donor fluorophore, and wherein the labeled probe hybridizes to an amplified copy of the target nucleic acid sequence within 15 nucleotides of the labeled primer;

(b) amplifying the target nucleic acid sequence by polymerase chain reaction;

(c) illuminating the biological sample with light of a selected wavelength that is absorbed by said donor fluorophore; and (d) detecting the fluorescence emission of the sample.

An improved method of amplifying a target nucleic acid sequence of a biological sample comprises (a) adding to the biological sample an effective amount of a nucleic-acid-binding fluorescent entity;

(b) amplifying the target nucleic acid sequence using polymerase chain reaction, comprising thermally cycling the biological sample using initial predetermined temperature and time parameters, and then (i) illuminating the biological sample with a selected wavelength of light that is absorbed by the fluorescent entity during the polymerase chain reaction;

(ii) monitoring fluorescence from the sample to determine the optimal temperature and time parameters for the polymerase chain reaction; and (iii) adjusting the initial temperature and time parameters in accordance with the fluorescence.

In one illustrative embodiment, the fluorescent entity comprises a double strand specific nucleic acid binding dye, and in another illustrative embodiment the fluorescent entity comprises a fluorescently labeled oligonucleotide probe that hybridizes to the targeted nucleic acid sequence.

A method or detecting a target nucleic acid sequence of a biological sample comprises (a) adding to the biological sample an effective amount of a pair of oligonucleotide probes that hybridize to the target nucleic acid sequence, one of the probes being labeled with an acceptor fluorophore and the other probe labeled with a donor fluorophore of a fluorescence energy transfer pair, wherein an emission spectrum of the donor fluorophore and an absorption spectrum of the acceptor fluorophore overlap less than 25%, the acceptor fluorophore has a peak extinction coefficient greater than 100,000 $M^{-1}cm^{-1}$ and upon hybridization of the two probes, the donor and acceptor fluorophores are within 25 nucleotides of one another;

(b) illuminating the biological sample with a selected wavelength of light that is absorbed by said donor fluorophore; and (c) detecting the emission of the biological sample.

An illustrative resonance energy transfer pair comprises fluorescein as the donor and Cy5 or Cy5.5 as the acceptor.

A method of real time monitoring of a polymerase chain reaction amplification of a target nucleic acid sequence in a biological sample comprises amplifying the target sequence by polymerase chain reaction in the presence of two nucleic acid probes that hybridize to adjacent regions of the target sequence, one of the probes being labeled with an acceptor fluorophore and the other probe labeled with a donor fluorophore of a fluorescence energy transfer pair such that upon hybridization of the two probes with the target sequence, the donor and acceptor fluorophores are within 25 nucleotides of one another, the polymerase chain reaction comprising the steps of adding a thermostable polymerase and primers for the targeted nucleic acid sequence to the biological sample and thermally cycling the biological sample between at least a denaturation temperature and an elongation temperature;

exciting the biological sample with light at a wavelength absorbed by the donor fluorophore and detecting the emission from the biological sample; and monitoring the temperature dependent fluorescence from the fluorescence energy transfer pair.

A method of real time monitoring of a polymerase chain reaction amplification of a target nucleic acid sequence in a biological sample comprises amplifying the target sequence by polymerase chain reaction in the presence of SYBR™ Green I, the polymerase chain reaction comprising the steps of adding a thermostable polymerase and primers for the targeted nucleic acid sequence to the biological sample and thermally cycling the biological sample between at least a denaturation temperature and an elongation temperature;

exciting the biological sample with light at a wavelength absorbed by the SYBR™ Green I and detecting the emission from the biological sample; and monitoring the temperature dependent fluorescence from the SYBR™ Green I. Preferably, the monitoring step comprises determining a melting profile of the amplified target sequence.

A method for analyzing a target DNA sequence of a biological sample comprises (a) adding to the biological sample an effective amount of two nucleic acid primers and a nucleic acid probe, wherein one of the primers and the probe are each labeled with one member of a fluorescence energy transfer pair comprising an acceptor fluorophore and a donor fluorophore, and wherein the labeled probe hybridizes to an amplified copy of the target nucleic acid sequence within 15 nucleotides of the labeled primer;

(b) amplifying the target nucleic acid sequence by polymerase chain reaction;

(c) illuminating the biological sample with light of a selected wavelength that is absorbed by said donor fluorophore and detecting the fluorescence emission of the sample. In another illustrative embodiment, the method further comprises the step of monitoring the temperature dependent fluorescence of the sample, preferably by determining a melting profile of the amplified target sequence.

A method of detecting a difference at a selected locus in a first nucleic acid as compared to a second nucleic acid comprises (a) providing a pair of oligonucleotide primers configured for amplifying, by polymerase chain reaction, a selected segment of the first nucleic acid and a corresponding segment of the second nucleic acid, wherein the selected segment and corresponding segment each comprises the selected locus, to result in amplified products containing a copy of the selected locus;

(b) providing a pair of oligonucleotide probes, one of the probes being labeled with an acceptor fluorophore and the other probe being labeled with a donor fluorophore of a fluorogenic resonance energy transfer pair such that upon hybridization of the two probes with the amplified products the donor and acceptor are in resonance energy transfer relationship, wherein one of the probes is configured for hybridizing to the amplified products such that said one of the probes spans the selected locus and exhibits a melting profile when the difference is present in the first nucleic acid that is distinguishable from a melting profile of the second nucleic acid;

(c) amplifying the selected segment of first nucleic acid and the corresponding segment of the second nucleic acid by polymerase chain reaction in the presence of effective amounts of probes to result in an amplified selected segment and an amplified corresponding segment, at least a portion thereof having both the probes hybridized thereto with the fluorogenic resonance energy transfer pair in resonance energy transfer relationship;

(d) illuminating the amplified selected segment and the amplified corresponding segment with the probes hybridized thereto with a selected wavelength of light to elicit fluorescence by the fluorogenic resonance energy transfer pair;

(e) measuring fluorescence emission as a function of temperature to determine in a first melting profile of said one of the probes melting from the amplified selected segment of first nucleic acid and a second melting profile of said one of the probes melting from the amplified corresponding segment of second nucleic acid; and (f) comparing the first melting profile to the second melting profile, wherein a difference therein indicates the presence of the difference in the sample nucleic acid.

A method of detecting a difference at a selected locus in a first nucleic acid as compared to a second nucleic acid comprises (a) providing a pair of oligonucleotide primers configured for amplifying, by polymerase chain reaction, a selected segment of the first nucleic acid and a corresponding segment of the second nucleic acid, wherein the selected segment and corresponding segment each comprises the selected locus, to result in amplified products containing a copy of the selected locus;

(b) providing an oligonucleotide probe, wherein one of the primers and the probe are each labeled with one member of a fluorescence energy transfer pair comprising an donor fluorophore and an acceptor fluorophore, and wherein the labeled probe and labeled primer hybridize to the amplified products such that the donor and acceptor are in resonance energy transfer relationship, and wherein the probe is configured for hybridizing to the amplified products such that said probe spans the selected locus and exhibits a melting profile when the difference is present in the first nucleic acid that is distinguishable from a melting profile of the second nucleic acid;

(c) amplifying the selected segment of first nucleic acid and the corresponding segment of the second nucleic acid by polymerase chain reaction in the presence of effective amounts of primers and probe to result in an amplified selected segment and an amplified corresponding segment, at least a portion thereof having the labeled primer and probe hybridized thereto with the fluorogenic resonance energy transfer pair in resonance energy transfer relationship;

(d) illuminating the amplified selected segment and the amplified corresponding segment with the labeled primer and probe hybridized thereto with a selected wavelength of light to elicit fluorescence by the fluorogenic resonance energy transfer pair;

(e) measuring fluorescence emission as a function of temperature to determine in a first melting profile of said probe melting from the amplified selected segment of first nucleic acid and a second melting profile of said probe melting from the amplified corresponding segment of second nucleic acid; and (f) comparing the first melting profile to the second melting profile, wherein a difference therein indicates the presence of the difference in the sample nucleic acid.

A method of detecting heterozygosity at a selected locus in the genome of an individual, wherein the genome comprises a mutant allele and a corresponding reference allele, each comprising the selected locus, comprises (a) obtaining sample genomic DNA from the individual;

(b) providing a pair of oligonucleotide primers configured for amplifying, by polymerase chain reaction, a first selected segment of the mutant allele and a second selected segment of the corresponding reference allele wherein both the first and second selected segments comprise the selected locus;

(c) providing a pair of oligonucleotide probes, one of the probes being labeled with an acceptor fluorophore and the other probe being labeled with a donor fluorophore of a fluorogenic resonance energy transfer pair such that upon hybridization of the two probes with the amplified first and second selected segments one of the probes spans the selected locus and exhibits a first melting profile with the amplified first selected segment that is distinguishable from a second melting profile with the amplified second selected segment;

(d) amplifying the first and second selected segments of sample genomic DNA by polymerase chain reaction in the presence of effective amounts of probes to result in amplified first and second selected segments, at least a portion thereof having both the probes hybridized thereto with the fluorogenic resonance energy transfer pair in resonance energy transfer relationship;

(e) illuminating the amplified first and second selected segments having the probes hybridized thereto with a selected wavelength of light to elicit fluorescence by the donor and acceptor;

(f) measuring a fluorescence emission as a function of temperature to determine a first melting profile of said one of the probes melting from the amplified first selected segment and a second melting profile of said one of the probes melting from the amplified second selected segment; and (g) comparing the first melting profile to the second melting profile, wherein distinguishable melting profiles indicate heterozygosity in the sample genomic DNA.

A method of detecting heterozygosity at a selected locus in the genome of an individual, wherein the genome comprises a mutant allele and a corresponding reference allele, each comprising the selected locus, comprises (a) obtaining sample genomic DNA from the individual;

(b) providing a pair of oligonucleotide primers configured for amplifying, by polymerase chain reaction, a first selected segment of the mutant allele and a second selected segment of the corresponding reference allele wherein both the first and second selected segments comprise the selected locus;

(c) providing an oligonucleotide probe, wherein one of the primers and the probe are each labeled with one member of a fluorescence energy transfer pair comprising an donor fluorophore and an acceptor fluorophore, and wherein the labeled probe and labeled primer hybridize to the amplified first and second selected segments such that one of the probes spans the selected locus and exhibits a first melting profile with the amplified first selected segment that is distinguishable from a second melting profile with the amplified second selected segment;

(d) amplifying the first and second selected segments of sample genomic DNA by polymerase chain reaction in the presence of effective amounts of primers and probe to result in amplified first and second selected segments, at least a portion thereof having both the labeled primer and probe hybridized thereto with the fluorogenic resonance energy transfer pair in resonance energy transfer relationship;

(e) illuminating the amplified first and second selected segments having the labeled primer and probe hybridized thereto with a selected wavelength of light to elicit fluorescence by the donor and acceptor;

(f) measuring a fluorescence emission as a function of temperature to determine a first melting profile of said probe melting from the amplified first selected segment and a second melting profile of said probe melting from the amplified second selected segment; and (g) comparing the first melting profile to the second melting profile, wherein distinguishable melting profiles indicate heterozygosity in the sample genomic DNA.

A method of determining completion of a polymerase chain reaction in a polymerase chain reaction mixture comprising (1) a nucleic acid wherein the nucleic acid or a polymerase-chain-reaction-amplified product thereof consists of two distinct complementary strands, (2) two oligonucleotide primers configured for amplifying by polymerase chain reaction a selected segment of the nucleic acid to result in an amplified product, and (3) a DNA polymerase for catalyzing the polymerase chain reaction, comprises (a) adding to the mixture (1) an effective amount of an oligonucleotide probe labeled with a resonance energy transfer donor or a resonance energy transfer acceptor of a fluorogenic resonance energy transfer pair, wherein the probe is configured for hybridizing to the amplified product under selected conditions of temperature and monovalent ionic strength, and (2) an effective amount of a reference oligonucleotide labeled with the donor or the acceptor, with the proviso that as between the probe and reference oligonucleotide one is labeled with the donor and the other is labeled with the acceptor, wherein the reference oligonucleotide is configured for hybridizing to the amplified product under the selected conditions of temperature and monovalent ionic strength such that the donor and the acceptor are in resonance energy transfer relationship when both the probe and the reference oligonucleotide hybridize to the amplified product;

(b) amplifying the selected segment of nucleic acid by polymerase chain reaction to result in the amplified product, at least a portion thereof having both the probe and the reference oligonucleotide hybridized thereto with the fluorogenic resonance energy transfer pair in resonance energy transfer relationship; and (c) illuminating the amplified product having the probe and reference oligonucleotide hybridized thereto with a selected wavelength of light for eliciting fluorescence by the fluorogenic resonance energy pair and monitoring fluorescence emission and determining a cycle when the fluorescence emission reaches a plateau phase, indicating the completion of the reaction.

A method of determining completion of a polymerase chain reaction in a polymerase chain reaction mixture comprising (1) a nucleic acid wherein the nucleic acid or a polymerase-chain-reaction-amplified product thereof consists of two distinct complementary strands, (2) two oligonucleotide primers configured for amplifying by polymerase chain reaction a selected segment of the nucleic acid to result in an amplified product, and (3) a DNA polymerase for catalyzing the polymerase chain reaction, comprises (a) adding to the mixture an effective amount of a nucleic-acid-binding fluorescent dye;

(b) amplifying the selected segment of nucleic acid by polymerase chain reaction in the mixture to which the nucleic-acid-binding fluorescent dye has been added to result in the amplified product with nucleic-acid-binding fluorescent dye bound thereto; and (c) illuminating amplified product with nucleic-acid-binding fluorescent dye bound thereto with a selected wavelength of light for eliciting fluorescence therefrom and monitoring fluorescence emission and determining a cycle when the fluorescence emission reaches a plateau phase, indicating the completion of the reaction. Preferably, the nucleic-acid-binding fluorescent dye is a member selected from the group consisting of SYBR™ GREEN I, ethidium bromide, pico green, acridine orange, thiazole orange, YO-PRO-1, and chromomycin A3, and more preferably is SYBR™ GREEN I.

A method of controlling temperature cycling parameters of a polymerase chain reaction comprising repeated cycles of annealing, extension, and denaturation phases of a polymerase chain reaction mixture comprising a double-strand-specific fluorescent dye, wherein the parameters comprise duration of the annealing phase, duration of the denaturation phase, and number of cycles, comprises (a) illuminating the reaction with a selected wavelength of light for eliciting fluorescence from the fluorescent dye and continuously monitoring fluorescence during the repeated annealing, extension, and denaturation phases;

(b) determining at least
  (i) duration for fluorescence to stop increasing during the extension phase, or
  (ii) Duration for fluorescence to decrease to a baseline level during the denaturation phase, or
  (iii) a number of cycles for fluorescence to reach a preselected level during the extension phase; and (c) adjusting the length of the extension phase according to the length of time for fluorescence to stop increasing during the extension phase, the length of the denaturation phase according to the length of time for fluorescence to decrease to the baseline level during the denaturation phase, or the number of cycles according to the number of cycles for fluorescence to reach the preselected level during the extension phase.

A method of determining a concentration of an amplified product in a selected polymerase chain reaction mixture comprises (a) determining a second order rate constant for the amplified product at a selected temperature and reaction conditions by monitoring rate of hybridization of a known concentration of the amplified product;

(b) determining rate of annealing for an unknown concentration of the amplified product; and (c) calculating the concentration of the amplified product from the rate of annealing and the second order rate constant.

Preferably, the rate of annealing is determined after multiple cycles of amplification. One illustrative method of determining the second order rate constant comprises the steps of raising the temperature of a first polymerase chain reaction mixture comprising a known concentration of the amplified product and an effective amount of a double-strand specific fluorescent dye, above the denaturation temperature of the amplified product to result in a denatured amplified product;

rapidly reducing the temperature of the first polymerase chain reaction mixture comprising the known amount of denatured amplified product to a selected temperature below the denaturation temperature of the amplified product while continuously monitoring the fluorescence of the first polymerase chain reaction mixture as a function of time;

plotting fluorescence as a function of time for determining maximum fluorescence, minimum fluorescence, the time at minimum fluorescence, and a second order rate constant for the known concentration of amplified product from the equation wherein F is fluorescence, $F_{max}$ is maximum fluorescence, $F_{min}$ is minimum fluorescence, k is $$F = F_{max} - \frac{F_{max} - F_{min}}{k(t - t_0)[DNA] + 1}$$

the second order rate constant, $t_0$ is the time at $F_{min}$, and [DNA] is the known concentration of the amplified product.

A method of determining a concentration of a selected nucleic acid template by competitive quantitative polymerase chain reaction comprises the steps of:

(a) in a reaction mixture comprising:
  (i) effective amounts of each of a pair of oligonucleotide primers configured for amplifying, in a polymerase chain reaction, a selected segment of the selected template and a corresponding selected segment of a competitive template to result in amplified products thereof,
  (ii) an effective amount of an oligonucleotide probe labeled with a resonance energy transfer donor or a resonance energy transfer acceptor of a fluorogenic resonance energy transfer pair, wherein the probe is configured for hybridizing to the amplified products such that the probe melts from the amplified product of the selected template at a melting temperature that is distinguishable from the melting temperature at which the probe melts from the amplified product of the competitive template,
  (iii) an effective amount of a reference oligonucleotide labeled with the donor or the acceptor, with the proviso that as between the probe and transfer oligonucleotide one is labeled with the donor and the other is labeled with the acceptor, wherein the reference oligonucleotide is configured for hybridizing to the amplified products such that the donor and the acceptor are in resonance energy transfer relationship when both the probe and the reference oligonucleotide hybridize to the amplified products;

amplifying, by polymerase chain reaction, an unknown amount of the selected template and a known amount of the competitive template to result in the amplified products thereof;

(b) illuminating the reaction mixture with a selected wavelength of light for eliciting fluorescence by the fluorogenic resonance energy transfer pair and determining a fluorescence emission as a function of temperature as the temperature of the reaction mixture is changed to result in a first melting curve of the probe melting from the amplified product of the selected template and a second melting curve of the probe melting from the competitive template;

(c) converting the first and second melting curves to first and second melting peaks and determining relative amounts of the selected template and the competitive template from such melting peaks; and (d) calculating the concentration of the selected template based on the known amount of the competitive template and the relative amounts of selected template and competitive template.

A fluorogenic resonance energy transfer pair consists of fluorescein and Cy5 or Cy5.5.

A method of determining a concentration of a selected nucleic acid template in a polymerase chain reaction comprises the steps of:

(a) in a reaction mixture comprising:
  (i) effective amounts of each of a first pair of oligonucleotide primers configured for amplifying, in a polymerase chain reaction, a selected first segment of the selected template to result in an amplified first product thereof,
  (ii) effective amounts of each of a second pair of oligonucleotide primers configured for amplifying, in a polymerase chain reaction, a selected second segment of a reference template to result in an amplified second product thereof,
  (iii) an effective amount of a nucleic-acid-binding fluorescent dye;

amplifying, by polymerase chain reaction, an unknown amount of the selected template to result in the amplified first product and a known amount of the reference template to result in the amplified second product thereof;

(b) illuminating the reaction mixture with a selected wavelength of light for eliciting fluorescence by the nucleic-acid-binding fluorescent dye and continuously monitoring the fluorescence emitted as a function of temperature to result in a melting curve of the amplified products wherein the first product and second product melt at different temperatures;

(c) converting the melting curves to melting peaks and determining relative amounts of the selected template and the reference template from such melting peaks; and (d) calculating the concentration of the selected template based on the known amount of the reference template and the relative amounts of selected template and reference template.

A method of monitoring amplification of a selected template in a polymerase chain reaction that also comprises a positive control template comprises the steps of:

(a) in a reaction mixture comprising:
  (i) effective amounts of each of a first pair of oligonucleotide primers configured for amplifying, in a polymerase chain reaction, a selected first segment of the selected template to result in an amplified first product thereof,
  (ii) effective amounts of each of a second pair of oligonucleotide primers configured for amplifying, in a polymerase chain reaction, a selected second segment of the positive control template to result in an amplified second product thereof,
  (iii) an effective amount of a nucleic-acid-binding fluorescent dye;

subjecting the selected template and the positive control template to conditions for amplifying the selected template and the positive control template by polymerase chain reaction; and (b) illuminating the reaction mixture with a selected wavelength of light for eliciting fluorescence by the nucleic-acid-binding fluorescent dye and continuously monitoring the fluorescence emitted as a function of temperature during an amplification cycle of the polymerase chain reaction to result in a first melting peak of the amplified first product, if the selected template is amplified, and a second melting peak of the amplified second product, if the positive control template is amplified;

wherein obtaining of the second melting curve indicates that the polymerase chain reaction was operative, obtaining the first melting curve indicates that the selected first segment was amplifiable, and absence of the first melting curve indicates that the selected first segment was not amplifiable.

A method of detecting the factor V Leiden mutation in an individual, wherein the factor V Leiden mutation consists of a single base change at the factor V Leiden mutation locus as compared to wild type, comprises the steps of:

(a) obtaining sample genomic DNA from the individual;

(b) providing wild type genomic DNA as a control;

(c) providing a pair of oligonucleotide primers configured for amplifying by polymerase chain reaction a selected segment of the sample genomic DNA and of the wild type genomic DNA wherein the selected segment comprises the factor V Leiden mutation locus to result in amplified products containing a copy of the factor V Leiden mutation locus;

(d) providing an oligonucleotide probe labeled with a resonance energy transfer donor or a resonance energy transfer acceptor of a fluorogenic resonance energy transfer pair, wherein the probe is configured for hybridizing to the amplified products such that the probe spans the mutation locus and exhibits a melting profile when the factor V Leiden mutation is present in the sample genomic DNA that is differentiable from a melting profile of the wild type genomic DNA;

(e) providing a transfer oligonucleotide labeled with the resonance energy transfer donor or the resonance energy transfer acceptor, with the proviso that as between the probe and transfer oligonucleotide one is labeled with the resonance energy transfer donor and the other is labeled with the resonance energy transfer acceptor, wherein the transfer oligonucleotide is configured for hybridizing to the amplified products such that the resonance energy transfer donor and the resonance energy transfer acceptor are in resonance energy transfer relationship when both the probe and the transfer oligonucleotide hybridize to the amplified products;

(f) amplifying the selected segment of sample genomic DNA and wild type genomic DNA by polymerase chain reaction in the presence of effective amounts of oligonucleotide probe and transfer oligonucleotide to result in amplified selected segments, at least a portion thereof having both the probe and the transfer oligonucleotide hybridized thereto with the fluorogenic resonance energy transfer pair in resonance energy transfer relationship;

(g) determining fluorescence as a function of temperature during an amplification cycle of the polymerase chain reaction to result in a melting profile of the probe melting from the amplified segment of sample genomic DNA and a melting profile of the probe melting from the amplified segment of wild type genomic DNA; and (h) comparing the melting profile for the sample genomic DNA to the melting profile for the wild type genomic DNA, wherein a difference therein indicates the presence of the factor V Leiden mutation in the sample genomic DNA.

A method of analyzing nucleic acid hybridization comprises the steps of (a) providing a mixture comprising a nucleic acid sample to be analyzed and a nucleic acid binding fluorescent entity; and (b) monitoring fluorescence while changing temperature at a rate of $\geq 0.1°$ C./second.

A method of quantitating an initial copy number of a sample containing an unknown amount of nucleic acid comprises the steps of (a) amplifying by polymerase chain reaction at least one standard of known concentration in a mixture comprising the standard and a nucleic acid binding fluorescent entity;

(b) measuring fluorescence as a function of cycle number to result in a set of data points;

(c) fitting the data points to a given predetermined equation describing fluorescence as a function of initial nucleic acid concentration and cycle number;

(d) amplifying the sample containing the unknown amount of nucleic acid in a mixture comprising the sample and the nucleic acid binding fluorescent entity and monitoring fluorescence thereof; and (e) determining initial nucleic acid concentration from the equation determined in step (c).

A fluorescence resonance energy transfer pair is disclosed wherein the pair comprises a donor fluorophore having an emission spectrum and an acceptor fluorophore having an absorption spectrum and an extinction coefficient greater than 100,000 $M^{-1}cm^{-1}$, wherein the donor fluorophore's emission spectrum and the acceptor fluorophore's absorption spectrum overlap less than 25%. One illustrative fluorescence resonance energy transfer pair described is where the donor fluorophore is fluorescein and the acceptor fluorophore is Cy5 or Cy5.5.

A method for analyzing a target DNA sequence of a biological sample comprises
  amplifying the target sequence by polymerase chain reaction in the presence of a nucleic acid binding fluorescent entity, said polymerase chain reaction comprising the steps of adding a thermostable polymerase and primers for the targeted nucleic acid sequence to the biological sample and thermally cycling the biological sample between at least a denaturation temperature and an elongation temperature;
  exciting the sample with light at a wavelength absorbed by the nucleic acid binding fluorescent entity; and
  monitoring the temperature dependent fluorescence from the nucleic acid binding fluorescent entity as temperature of the sample is changed. Preferably, the nucleic acid binding fluorescent entity comprises a double stranded nucleic acid binding fluorescent dye, such as SYBR™ Green I. The temperature dependent fluorescence can be used to identify the amplified products, preferably by melting curve analysis. Relative amounts of two or more amplified products can be determined by analysis of melting curves. For example, areas under the melting curves are found by non-linear least squares regression of the sum of multiple gaussians.

BRIEF DESCRIPTION OF THE SEVERAL VIEWS OF THE DRAWINGS

FIGS. 5A, B & C illustrate the mechanism of fluorescence generation for three different methods of fluorescence monitoring of PCR: (A)(1) and (A)(2) double-stranded DNA dye, (B)(1) and (B)(2) hydrolysis probe, and (C)(1) and (C)(2) hybridization probes.

FIGS. 42A-D show (A) a relative fluorescence v. cycle number plot for PCR amplified products from various amounts of β-globin template, (B) melting peaks and (C) electrophoretic bands of the various products, and (D) corrected fluorescence of the data of (A).

FIGS. 46A&B show (A) melting curves and (B) melting peaks for PCR products of a person heterozygous for the factor V Leiden mutation (solid line), homozygous for the factor V Leiden mutation (dotted line), homozygous wild type (broken line), and no DNA control (alternating dot and dash).

DETAILED DESCRIPTION

Figure 1:
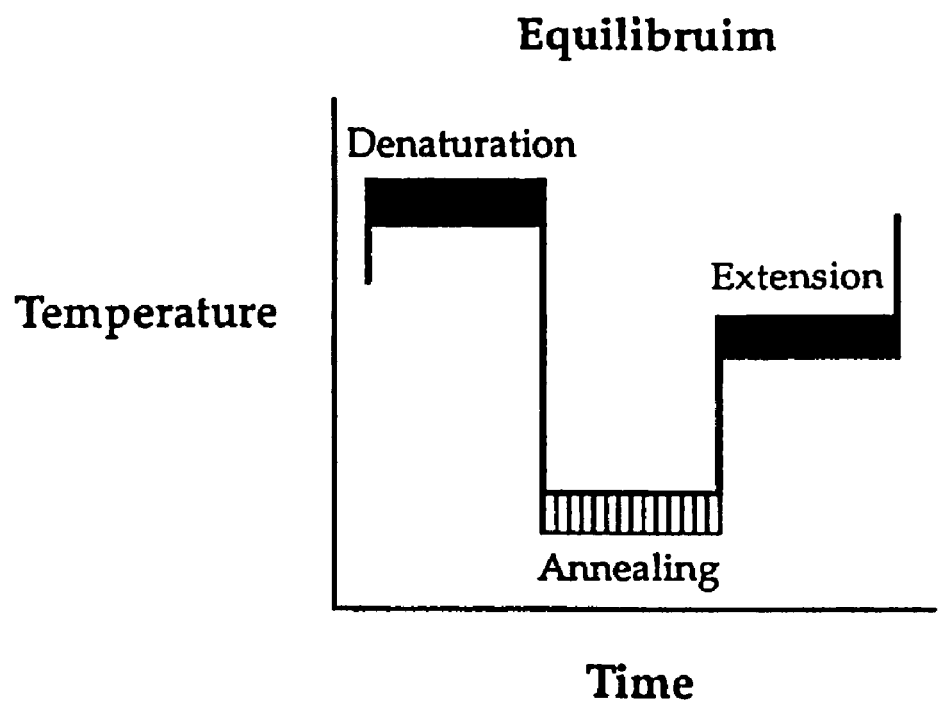
FIGS. 1A&B are graphs representing an equilibrium PCR paradigm (A) and a kinetic PCR paradigm (B).
Figure 1:
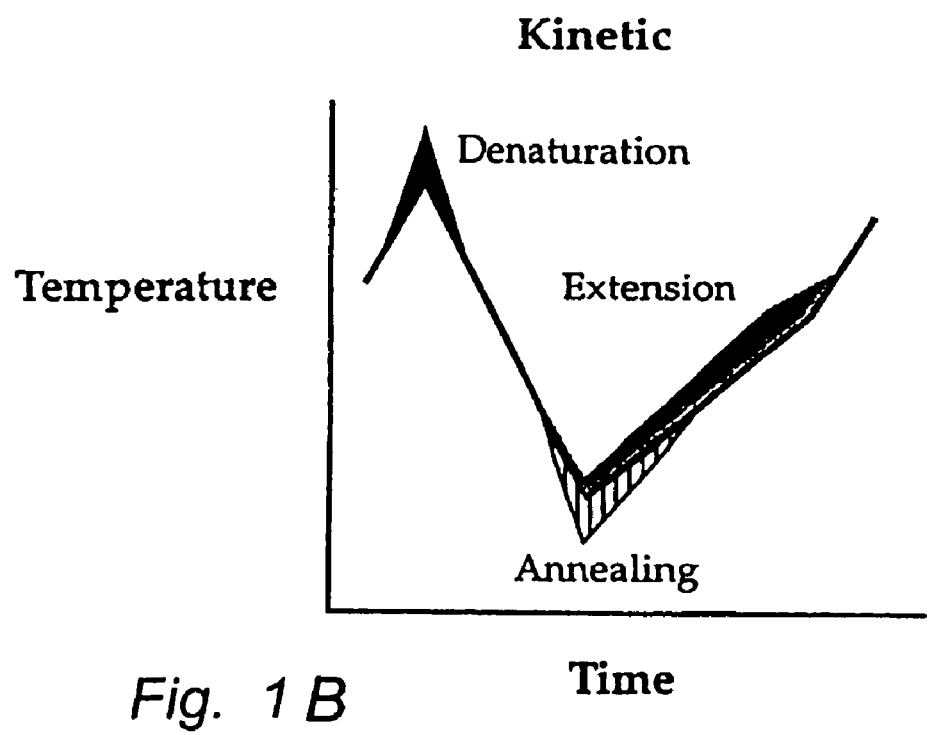

Before the present methods for monitoring hybridization during PCR are disclosed and described, it is to be understood that this invention is not limited to the particular configurations, process steps, and materials disclosed herein as such configurations, process steps, and materials may vary somewhat. It is also to be understood that the terminology employed herein is used for the purpose of describing particular embodiments only and is not intended to be limiting since the scope of the present invention will be limited only by the appended claims and equivalents thereof.

It must be noted that, as used in this specification and the appended claims, the singular forms "a," "an," and "the" include plural referents unless the context clearly dictates otherwise.

In describing and claiming the present invention, the following terminology will be used in accordance with the definitions set out below.

As used herein, "nucleic acid," "DNA," and similar terms also include nucleic acid analogs, i.e. analogs having other than a phosphodiester backbone. For example, the so-called "peptide nucleic acids," which are known in the art and have peptide bonds instead of phosphodiester bonds in the backbone, are considered within the scope of the present invention.

As used herein, "continuous monitoring" and similar terms refer to monitoring multiple times during a cycle of PCR, preferably during temperature transitions, and more preferably obtaining at least one data point in each temperature transition.

As used herein, "cycle-by-cycle" monitoring means monitoring the PCR reaction once each cycle, preferably during the annealing phase of PCR.

As used herein, "fluorescence resonance energy transfer relationship" and similar terms refer to adjacent hybridization of an oligonucleotide labeled with a donor fluorophore and another oligonucleotide labeled with an acceptor fluorophore to a target nucleic acid such that the donor fluorophore can transfer resonance energy to the acceptor fluorophore such that the acceptor fluorophore produces a measurable fluorescence emission. If the donor fluorophore and acceptor fluorophore are spaced apart by too great a distance, then the donor fluorophore cannot transfer resonance energy to the acceptor fluorophore such that the acceptor fluorophore emits measurable fluorescence, and hence the donor fluorophore and acceptor fluorophore are not in resonance energy transfer relationship. Preferably, when the two labeled oligonucleotides are both probes and neither functions as a PCR primer ("probe-probe"), then the donor and acceptor fluorophores are within about 0-25 nucleotides, more preferably within about 0-5 nucleotides, and most preferably within about 0-2 nucleotides. A particularly preferred spacing is 1 nucleotide.

When one of the labeled oligonucleotides also functions as a PCR primer ("probe-primer"), then the donor and acceptor fluorophores are preferably within about 0-15 nucleotides and more preferably within about 4-6 nucleotides.

As used herein, "effective amount" means an amount sufficient to produce a selected effect. For example, an effective amount of PCR primers is an amount sufficient to amplify a segment of nucleic acid by PCR provided that a DNA polymerase, buffer, template, and other conditions, including temperature conditions, known in the art to be necessary for practicing PCR are also provided.

PCR requires repetitive template denaturation and primer annealing. These hybridization transitions are temperature-dependent. The temperature cycles of PCR that drive amplification alternately denature accumulating product at a high temperature and anneal primers to the product at a lower temperature. The transition temperatures of product denaturation and primer annealing depend primarily on GC content and length. If a probe is designed to hybridize internally to the PCR product, the melting temperature of the probe also depends on GC content, length, and degree of complementarity to the target. Fluorescence probes compatible with PCR can monitor hybridization during amplification.

In accordance with the present invention, which is preferably used in connection with rapid cycling (fully described in the above-mentioned U.S. Ser. No. 08/658,993, filed Jun. 4, 1996, entitled System And Method For Monitoring PCR Processes, and U.S. Ser. No. 08/537,612, filed Oct. 2, 1995, entitled Method For Rapid Thermal Cycling of Biological Samples), a kinetic paradigm for PCR is appropriate. Instead of thinking about PCR as three reactions (denaturation, annealing, extension) occurring at three different temperatures for three time periods (FIG. 1A), a kinetic paradigm for PCR is more useful (FIG. 1B). With a kinetic paradigm, the temperature vs. time curve consists of continuous transitions between overlapping reactions. Denaturation and annealing are so rapid that no holding time at a particular temperature is necessary. Extension occurs over a range of temperatures at varying rates. A complete analysis would require knowledge of all relevant rate constants over all temperatures. If rate constants of all reactions were known, a "physicochemical description of PCR" could be developed. Determining these rates would require precise sample temperature control and is greatly simplified by reaction monitoring during temperature cycling.

Figure 2:
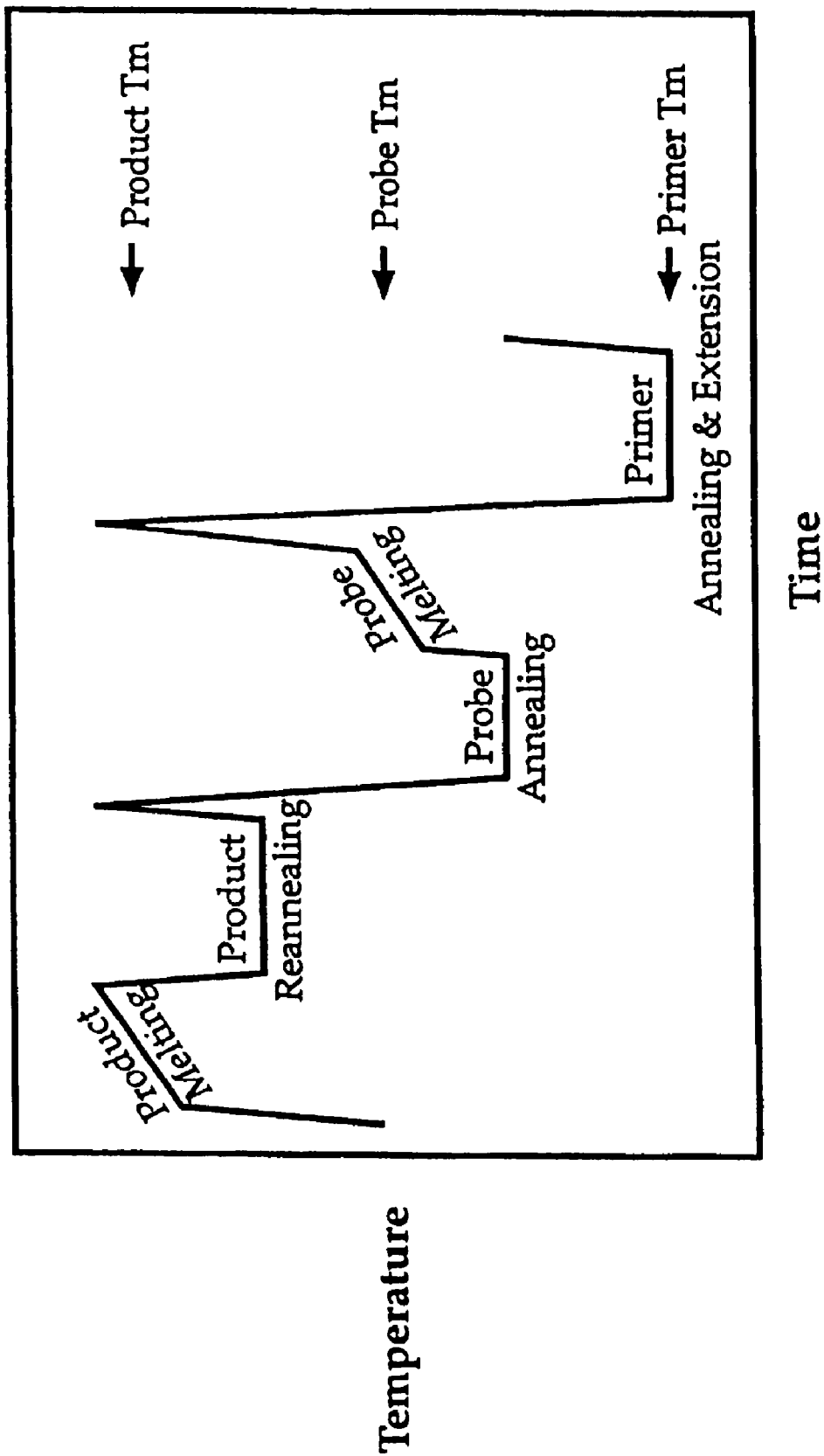
FIG. 2 illustrates useful temperature v. time segments for fluorescence hybridization monitoring.

FIG. 2 illustrates useful temperature v. time segments for fluorescence hybridization monitoring. Product melting curves are obtained during a slow temperature increase to denaturation. By quickly lowering the temperature after denaturation to a constant temperature, product, probe, or primer annealing can optionally be followed. Probe melting curves are obtained by slowly heating through temperatures around the probe Tm. The embodiment represented in FIG. 2 provides all analysis during temperature cycling with immediate real time display. Fluorescent probes are included as part of the amplification solution for continuous monitoring of primer, probe, or product hybridization during temperature cycling.

The fluorescence hybridization techniques contained herein are based on rapid cycling, with its advantages in speed and specificity.

Figure 3:
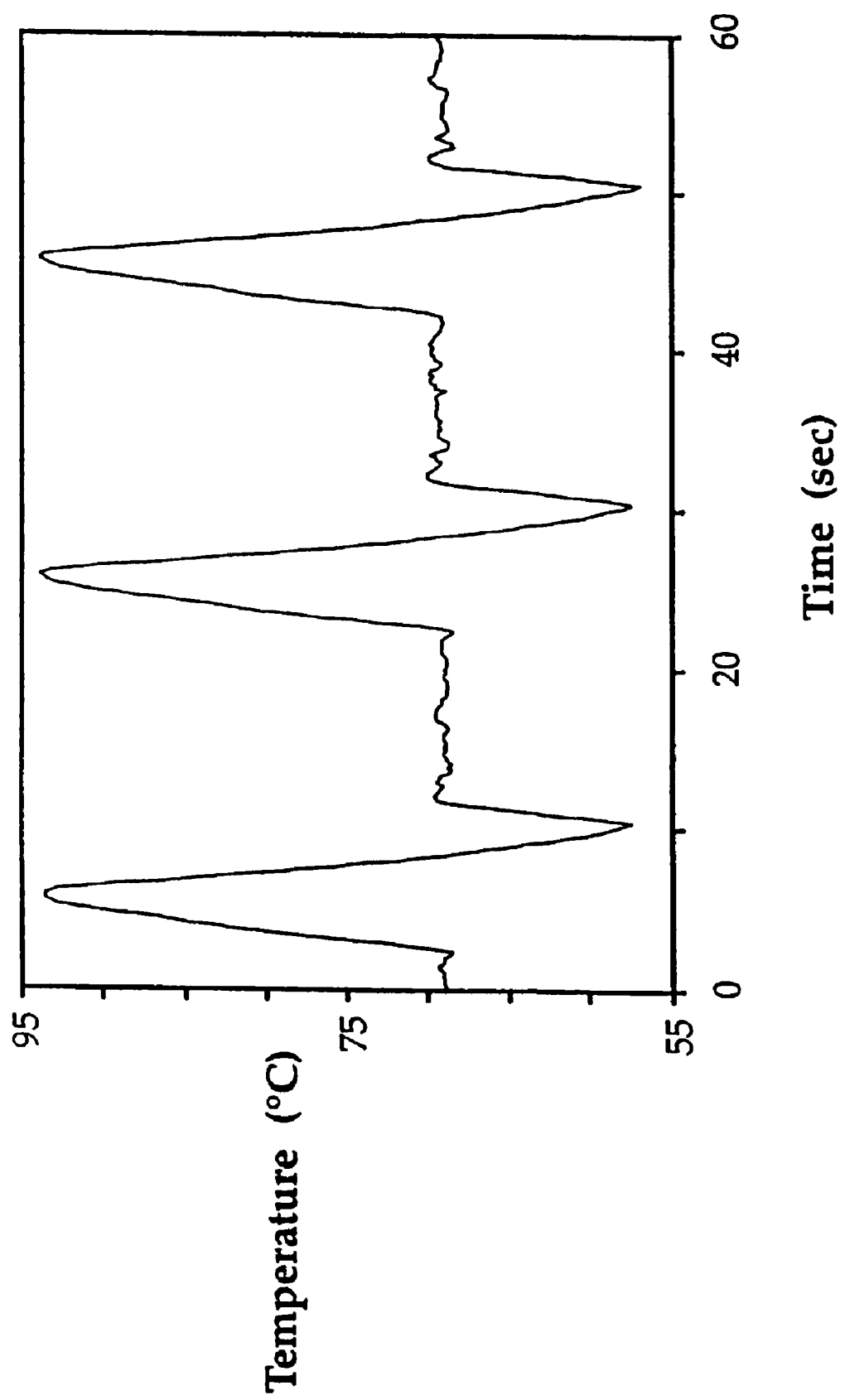
FIG. 3 is a temperature v. time chart exemplary of rapid temperature cycling for PCR.

A sample temperature profile during rapid cycle PCR is shown in FIG. 3. Denaturation and annealing appear as temperature "spikes" on these figures, as opposed to the broad plateaus of conventional temperature cycling for PCR, e.g. FIG. 1A. Rapid temperature cycling is contrasted to conventional temperature cycling in FIG. 4, wherein it is shown that 30 cycles of amplification can be completed in 15 minutes and the resulting PCR products contain many fewer side products. Thus, with rapid cycling the required times for amplification are reduced approximately 10-fold, and specificity is improved.

EXAMPLE 1

Figure 4:
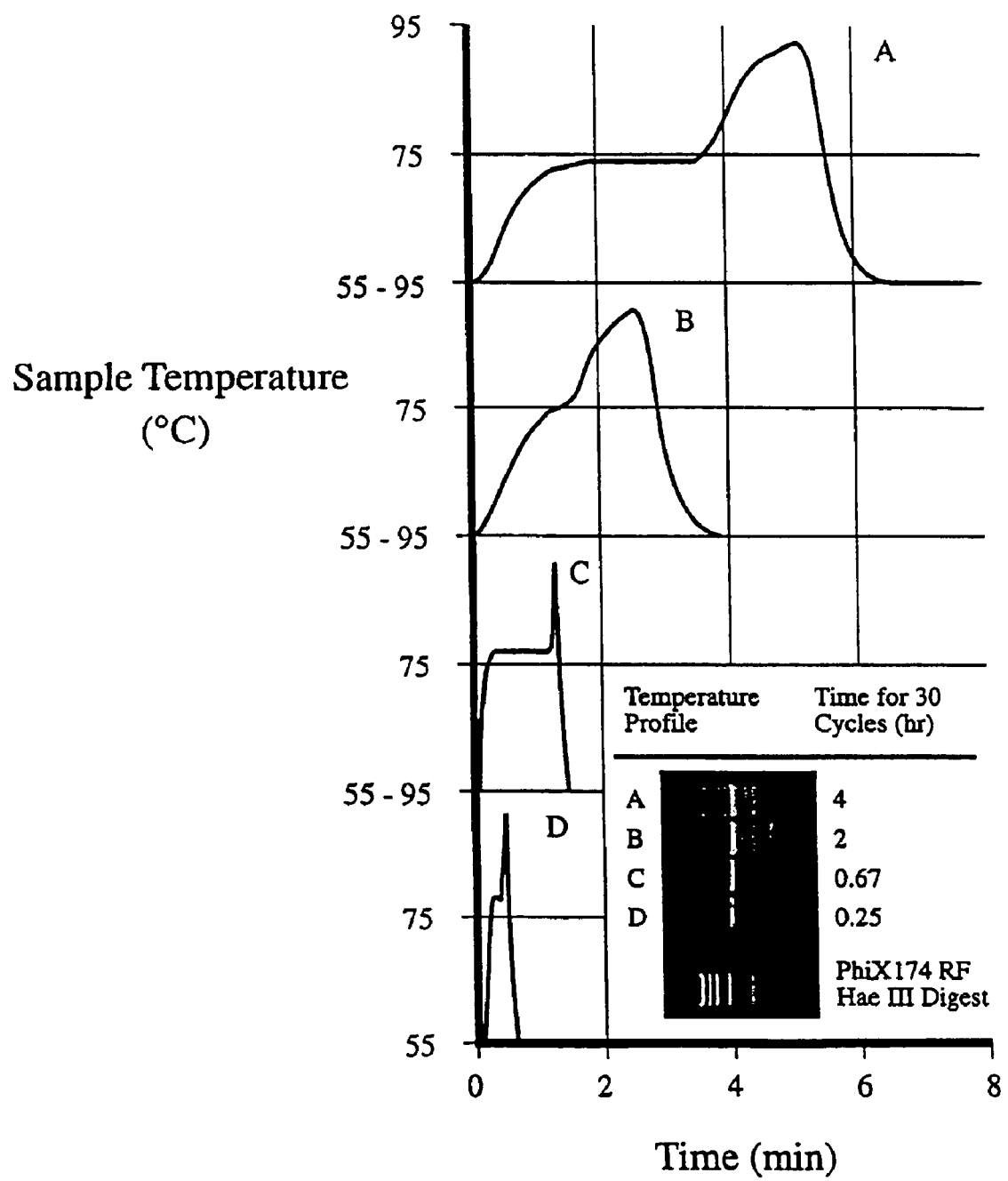
FIG. 4 shows the results of four different temperature/time profiles (A-D) and their resultant amplification products after thirty cycles (inset).

FIG. 4 shows the results of four different temperature/time profiles (A-D) and their resultant amplification products after thirty cycles (A-D). The profiles A and B in FIG. 4 were obtained using a prior art heating block device using a prior art microfuge tube. As can be seen in FIG. 4, the transitions between temperatures are slow and many nonspecific bands are present in profiles A and B. Profile B shows improvement in eliminating some of the nonspecific bands (in contrast to profile A) by limiting the time each sample remains at each temperature, thus indicating that shorter times produce more desirable results.

Profiles C and D were obtained using a rapid temperature cycler. As can be seen in FIG. 4, amplification is specific and, even though yield is maximal with 60-second elongation times (C), it is still entirely adequate with 10-second elongation times (D).

The optimal times and temperatures for the amplification of a 536 bp fragment of beta-globin from human genomic DNA were also determined. Amplification yields and product specificity were optimal when denaturation (93° C.) and annealing (55° C.) were less than 1 second. No advantage was found to longer denaturation or annealing times. The yield increased with longer elongation times at 77° C., but there was little change with elongation times longer than 10-20 seconds. These unexpected results indicate that the previously available devices used for DNA amplification are not maximizing the conditions needed to optimize the physical and enzymatic requirements of the reaction.

Further information can be obtained from: C. T. Wittwer et al., Rapid Cycle Allele-Specific Amplification with Cystic Fibrosis delta F(508) Locus, 39 *Clinical Chemistry* 804 (1993) and C. T. Wittwer et al., Rapid DNA Amplification, THE POLYMERASE CHAIN REACTION 174 (1994), which are both now incorporated herein by this reference. The instrumentation used for fluorescence acquisition and rapid temperature cycling is fully disclosed in Ser. No. 08/537,612, supra.

As indicated earlier, the polymerase chain reaction can be performed rapidly. In addition to facilitating rapid heat transfer, the use of optically clear capillary tubes allows for continuous fluorescence monitoring of DNA amplification in accordance with the present invention.

Fluorescent probes can be used to detect and monitor DNA amplification. Useful probes include double-stranded-DNA-specific dyes and sequence-specific probes. Three different fluorescence techniques for following DNA amplification are compared in FIG. 5. In FIG. 5A, fluorescence depends on the hybridization of PCR product as detected with a double-strand-specific DNA dye. In FIG. 5B, fluorescence depends on the hydrolysis of a 5'-exonuclease quenching probe, which is well known in the art as discussed above. FIG. 5C diagrams a hybridization scheme based on resonance energy transfer between fluorophores on two adjacent probes. The method of FIG. 5A is not sequence specific, although product specificity can be determined by melting curves, one aspect of the current invention. Both FIGS. 5B and 5C are sequence specific. However, the hybridization method also allows analysis with melting curves, another aspect of the current invention.

In monitoring fluorescence from reactions involving hydrolysis probes as in FIG. 5B and from reactions involving hybridization probes as in FIG. 5C, it is advantageous to measure fluorescence emitted by both the donor fluorophore and the acceptor fluorophore. In practice, the majority of the fluorescence emitted by hydrolysis probes is from the donor fluorophore, and the majority of the fluorescence emitted by hybridization probes is from the acceptor fluorophore.

Double-strand-specific DNA dye selection. Those skilled in the art will be familiar with the use of ethidium bromide in fluorescence techniques. When a double strand-specific fluorescent dye is present during amplification, fluorescence generally increases as more double stranded product is made, see R. Higuchi et al., Simultaneous amplification and detection of specific DNA sequences, 10 Bio/Technology 413-417 (1992). A fluorescence PCR assay for hepatitis C RNA using the intercalater, YO—PRO-1 is also known in the art. See T. Ishiguro et al., Homogeneous quantitative assay of hepatitis C virus RNA by polymerase chain reaction in the presence of a fluorescent intercalater, 229 Anal. Biochem. 207-213 (1995). It is preferred that SYBR™ Green I, which is well known in the art and available from Molecular Probes of Eugene, Oreg., be used as a double-strand-specific dye. The molecular structure of this dye is a trade secret, but it is recommended by the manufacturer as a more sensitive double-strand-specific dye for DNA detection on gels. SYBR™ Green I is heat labile, however, and thus is not useful for fluorescence monitoring of PCR according to conventional methods where the temperature of the reaction mixture is maintained at melting temperatures for extended periods of time. Because of this heat lability, it was unexpected to discover that SYBR™ Green I can be used to monitor PCR reactions when melting temperatures are not maintained for extended periods, i.e. when PCR is carried out by rapid cycling according to the kinetic paradigm described above.

EXAMPLE 2

Different double-strand-specific DNA dyes were compared by monitoring the amplification of a 110 base pair fragment from the PCO3/PCO4 primer pair of the human beta-globin gene from 10,000 template copies. Primers were synthesized by standard phosphoramidite chemistry as known in the art, namely, using Pharmacia Biotech Gene Assembler Plus (Piscataway, N.J.). The human beta-globin primers PC03/PC04 (110 base pairs) are described in C. T. Wittwer et al., Automated polymerase chain reaction in capillary tubes with hot air, 17 Nucl. Acids. Res. 4353-4357 (1989), which is now incorporated herein by reference. DNA amplification was performed in 50 mM Tris, pH 8.5 (25° C.), 3 mM MgCl$_2$, 500 µg/ml bovine serum albumin, 0.5 µM of each primer, 0.2 mM of each deoxynucleoside triphosphate and 0.2 U of Taq polymerase per 5 µl sample unless otherwise stated in the following examples. Purified amplification product was used as DNA template and was obtained by phenol/chloroform extraction and ethanol precipitation, see D. M. Wallace, Large- and small-scale phenol extractions and precipitation of nucleic acids, 152 Methods in Enzymology 33-48 (1987), followed by removal of primers by repeated washing through a Centricon 30 microconcentrator (Amicon, Danvers, Mass.). Template concentrations were determined by absorbance at 260 nm. A(260):A(280) ratios of templates were greater than 1.7.

SYBR™ Green I (Molecular Probes, Eugene, Oreg.) was used at a 1:10,000 dilution, ethidium bromide was at 5 µg/ml, and acridine orange was at 3 µg/ml. These concentrations were determined to be optimal concentrations for maximizing the fluorescence signal observed during amplification for each dye. Excitation was through a 450-490 nm interference filter from a xenon arc source, except for ethidium bromide, where a 520-550 nm excitation was used. For SYBR™ Green I, the emission at 520-550 nm was monitored. Ethidium bromide fluorescence was observed through a 580-620 nm bandpass. The acridine orange signal was taken as the ratio of green (520-550 nm) to red (>610 nm) fluorescence. The fluorescence of the sample before amplification was compared to the fluorescence after 35 cycles (94° C. max, 60° C. for 20 sec) at 60° C. The fluorescence increase was 5.3-fold for SYBR™ Green I, 1.7-fold for ethidium bromide, and 1.2-fold for acridine orange. In separate experiments, the fluorescence from SYBR™ Green I was stable for greater than 30 min at 70° C. It is also conveniently excited with visible light and is claimed to be less of a mutagen than ethidium bromide. Background fluorescence in all cases arose primarily from the primers.

SYBR™ Green I is a preferred double-strand-specific dye for fluorescence monitoring of PCR, primarily because of superior sensitivity, arising from greater discrimination between double stranded and single stranded nucleic acid. SYBR™ Green I can be used in any amplification and is inexpensive. In addition, product specificity can be obtained by analysis of melting curves, as will be described momentarily.

Resonance energy transfer dye selection for hybridization probes. Fluorescence resonance energy transfer can occur between 2 fluorophores if they are in physical proximity and the emission spectrum of one fluorophore overlaps the excitation spectrum of the other. Introductory theory on fluorescence resonance energy transfer can be found in many recent review articles. The rate of resonance energy transfer is:

$$(8.785E-5)(t^{-1})(k^2)(n^{-4})(q_D)(R^{-6})(J_{DA}), \text{where:}$$

t=excited state lifetime of the donor in the absence of the acceptor;

$k^2$=is an orientation factor between the donor and acceptor;

n=refractive index of visible light in the intervening medium;

$q_D$=quantum efficiency of the donor in the absence of the acceptor;

R=distance between the donor and acceptor (in angstroms);

$J_{DA}$=the integral of $(F_D)(e_A)(W^4)$ with respect to W at all overlapping wavelengths with:

$F_D$=peak normalized fluorescence spectrum of the donor, $e_A$=molar absorption coefficient of the acceptor ($M^{-1}cm^{-1}$), and W=wavelength (nm).

For any given donor and acceptor, a distance where 50% resonance energy transfer occurs can be calculated and is abbreviated $R_0$. Because the rate of resonance energy transfer depends on the 6th power of the distance between donor and acceptor, resonance energy transfer changes rapidly as R varies from $R_0$. At 2 $R_0$, very little resonance energy transfer occurs, and at 0.5 $R_0$, the efficiency of transfer is nearly complete, unless other forms of de-excitation predominate (i.e., collisional quenching). $R_0$ values for many different donor and acceptor pairs have been compiled and vary between 22 and 72 angstroms.

In double helical DNA, 10 bases are separated by about 34 angstroms. By labeling the bases of DNA with donor and acceptor fluorophores, resonance energy transfer has be used as a spectroscopic ruler to observe the helical geometry of DNA and analyze the structure of a four-way DNA junction. Resonance energy transfer can also be used as a monitor of hybridization. If a labeled oligonucleotide is hybridized to a labeled template strand, R can be brought from much greater than $R_0$ to well below $R_0$, increasing resonance energy transfer dramatically. Alternately, 2 labeled probes can be hybridized to the same template strand for a similar change in fluorescence energy transfer.

The practical use of resonance energy transfer to monitor hybridization depends on the sensitivity required and how much time is available. Using a competitive hybridization technique with 1 nM labeled probes, PCR-amplified DNA was detected after 15 min at 40° C. Faster signal generation is desirable. If only seconds were required for hybridization, PCR products could conveniently be quantified each cycle of amplification. Even further, the extent of probe hybridization could be monitored within a temperature cycle.

Hybridization is a second order process (see B. Young & M. Anderson, Quantitative analysis of solution hybridization, In: Nucleic Acid Hybridization: A Practical Approach 47-71, (B. Hames, S. Higgins eds., 1985). When the concentration of the probe is much greater than the concentration of the target, the hybridization rate is inversely proportional to concentration of probe. For example, by doubling the probe concentration, the hybridization time is cut in half. High probe concentrations would be necessary for cycle-by-cycle monitoring during PCR, because hybridization must occur before the hybridization site is covered by polymerase extension.

The high probe concentrations required for hybridization monitoring during PCR require a resonance energy transfer pair with unique characteristics. Consider excitation of a donor (D) and an acceptor (A) pair with light. The number of fluorophores of D and A directly excited will be proportional to the extinction coefficient (e) of each fluorophore at the excitation wavelength, or:

Number of D molecules directly excited=$(K)(e_D)$

Number of A molecules directly excited=$(K)(e_A)$ where K is a proportionality constant. De-excitation of the donor will occur by fluorescence, resonance energy transfer, and other processes summarized as thermal quenching. If $p_F$=probability of resonance energy transfer, and $p_{TD}$=probability of donor thermal quenching, then the probability of donor fluorescence is:

$1-p_F-p_{TD}$ and the number of fluorescing donor molecules is:

$(K)(e_D)(1-p_F-p_{TD})$

If the probability of detecting a donor emission in the donor emission window (for example, a bandpass filter window) is $p_{DD}$, then the number of observed donor emissions is:

$(p_{DD})(K)(e_D)(1-p_F-p_{TD})$

Now, the number of excited acceptor fluorophores is the sum of those directly excited and those excited through resonance energy transfer:

$(K)(e_A)+(K)(e_D)(p_F)$

If $p_{TA}$=the probability of thermal quenching of the acceptor, then the probability of acceptor fluorescence is:

$1-p_{TA}$ and the number of fluorescing acceptor molecules is:

$[(K)(e_A)+(K)(e_D)(p_F)][1-p_{TA}]$

If the probability of detecting an acceptor emission in the acceptor emission window is $p_{AA}$, then the number of observed acceptor emissions is:

$(p_{AA})[(K)(e_A)+(K)(e_D)(p_F)][1-p_{TA}]$

Finally, if the probability of observing a donor emission in the acceptor emission window is $p_{DA}$, then the number of observed emissions (both D and A) in the acceptor emission window is:

$(p_{AA})[(K)(e_A)+(K)(e_D)(p_F)][1-p_{TA}]+(p_{DA})(K)(e_D)$
$(1-p_F-p_{TD})$

Since fluorescence measurements are relative and K is present in all terms, if we remove K and rearrange, the observed intensity at the donor window is proportional to (donor excitation)−(energy transfer):

$(e_D)(p_{DD})(1-p_{TD})-(e_D)(p_{DD})(p_F)$     1)

and the observed intensity at the acceptor window is proportional to (acceptor excitation)+(energy transfer)+(donor emission in the acceptor window):

$(e_A)(p_{AA})(1-p_{TA})+(e_D)(p_{DD})(p_F)(1-p_{TA})+(e_D)(p_{DA})$
$(1-p_{TD}-p_F)$     2)

As resonance energy transfer increases, the donor signal decreases and the acceptor signal increases. The percent signal change depends on the background light intensity in each window. With high concentrations of probes, this background light intensity is high. During PCR, when varying target (product) concentrations need to be monitored, it is not possible to match the donor concentration to the target concentration. The excess donor molecules contribute to the background light intensity in both the donor and acceptor windows and partially mask the energy transfer phenomena. Background light in the acceptor window comes from not only donor emission in the acceptor window, but also from direct excitation of the acceptor. This background can be minimized with a low $e_A$ and a low $p_{DA}$.

The fluorescein/rhodamine fluorescence energy transfer pair, commonly used for nucleic acid detection, has high background fluorescence. Both direct acceptor excitation ($e_A$, ca. 10% $e_{MAX}$) and emission of the donor at wavelengths used to detect acceptor emission $p_{DA}$, ca. 20% peak emission) are high. This pair can be used to monitor liybridization if the probe concentration is near to the target concentration and enough time is allowed for complete hybridization. It is not a useful pair of fluorophores for continuous monitoring of PCR because high probe concentrations are required and the template concentration in PCR is continually changing.

Monitoring product concentration during PCR by hybridization has not been possible in the past because an acceptable resonance energy transfer pair had not been found. There have been few attempts to use resonance energy transfer for direct "noncompetitive" detection of hybridization. For example, U.S. Pat. No. 5,565,322 states "the observed energy transfer efficiency in terms of re-emission by the acceptor was relatively low." At probe concentrations that are high enough for significant hybridization to occur in seconds, the background fluorescence is too high.

Figure 6:
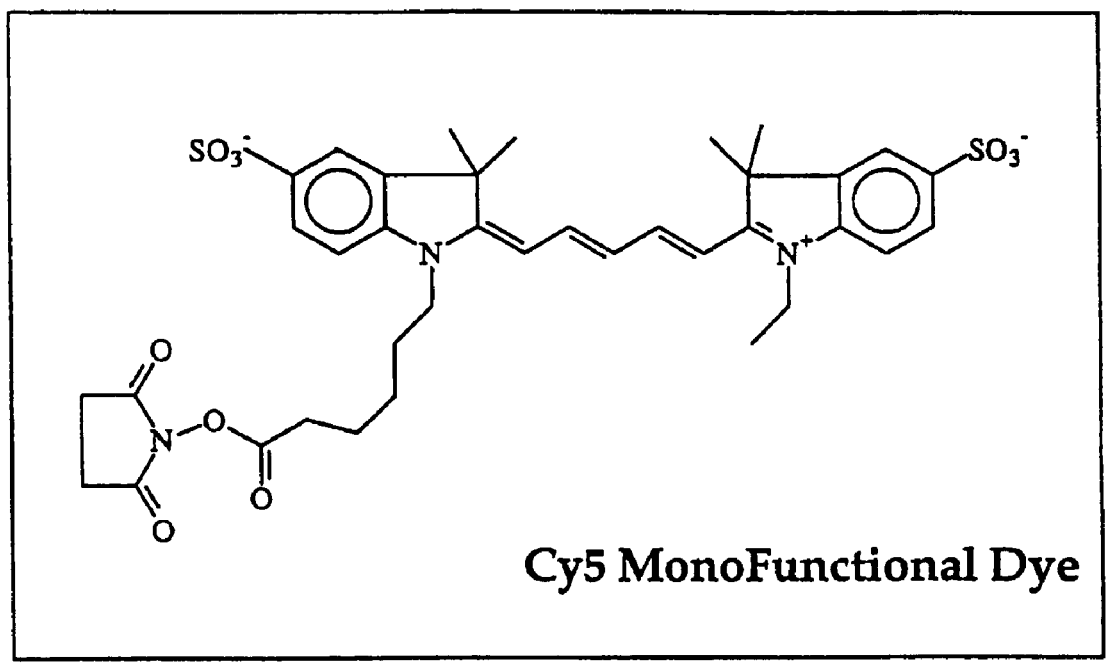
FIG. 6 shows the chemical structure of the monovalent N-hydroxysuccinimide ester of Cy5™.
Figure 7:
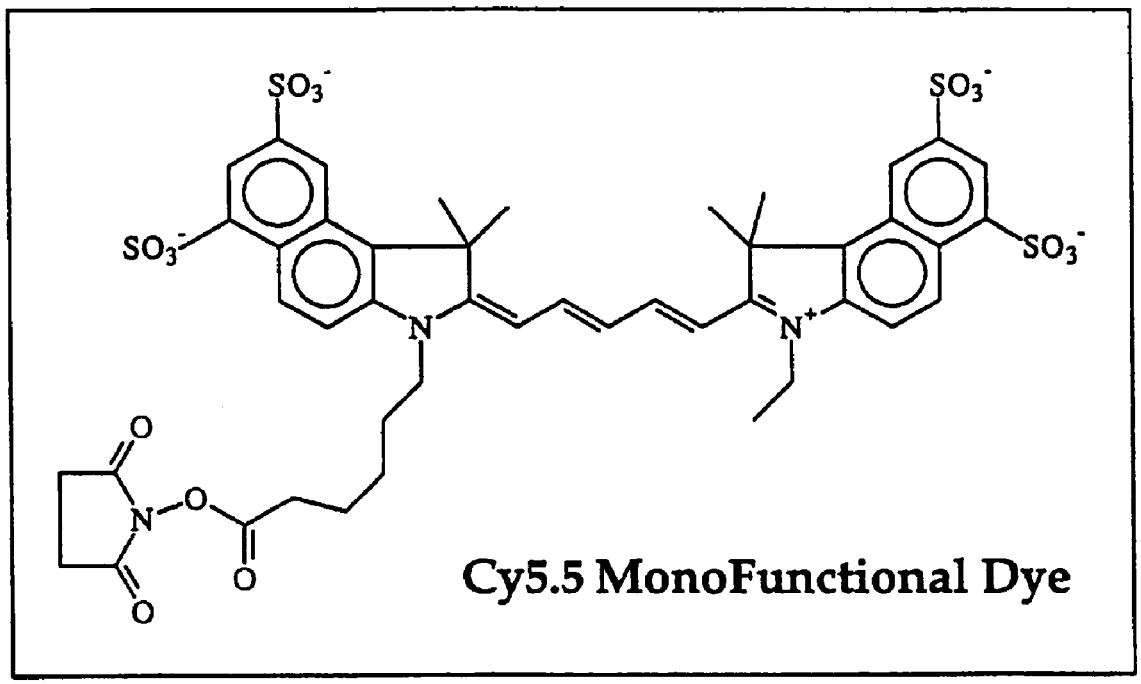
FIG. 7 shows the chemical structure of the monovalent N-hydroxysuccinimide ester of Cy5.5™.
Figure 8:
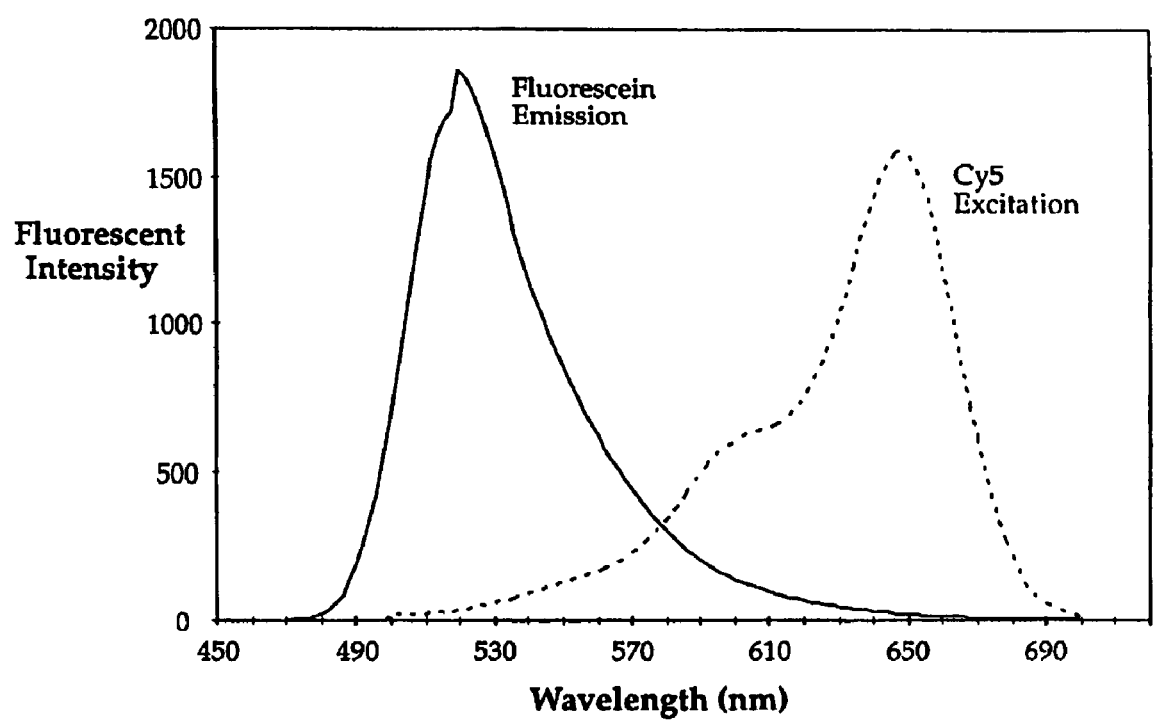
FIG. 8 shows the emission spectrum of fluorescein (solid line) and the excitation spectrum of Cy5 (broken line).

Fluorescein is perhaps the most widely used fluorophore. Its extinction coefficient and quantum efficiency are high and it is extensively used in microscopy, immunoassays, and flow cytometry. It is the donor in a commonly used resonance energy transfer pair with rhodamine. Cy5 is a popular red-emitting fluorophore with a very high extinction coefficient. The structure of the N-hydroxysuccinimide ester of Cy5 is shown in FIG. 6, and the structure of the related dye, Cy5.5, is shown in FIG. 7. These dyes are indodicarbocyanine dyes that are used commonly in flow cytometry and automated fluorescence sequencers and are available from Amersham (Pittsburgh, Pa.). Both fluorescein and Cy5 are commercially available as amidites for direct, automated incorporation into oligonucleotides. However, Cy5 has never been reported as a resonance energy transfer pair with fluorescein. Intuitively, fluorescein emission and Cy5 absorption do not overlap enough for resonance energy transfer to be considered. The emission spectrum of fluorescein and absorption spectrum of Cy5 attached to oligonucleotides are shown in FIG. 8. When the areas under the curves are normalized, the overlap from the technical spectra is 19%. Cy5.5 excitation is shifted to the red by about 25 nm, further decreasing the overlap with fluorescein emission to about 15%. Working in the red/infrared region of the spectrum is advantageous when choosing optical components for instrumentation. Laser diodes can be used for illumination, photodiode detectors have excellent sensitivity, and most materials have minimal autofluorescence in the pertinent spectral region.

Despite low spectral overlap, it has been discovered that fluorescein and either Cy5 or Cy5.5 make an excellent resonance energy transfer pair for hybridization monitoring during PCR.

EXAMPLE 3

A 110 bp beta-globin fragment was amplified from 50 ng human genomic DNA according to the procedure of Example 2 with the internal probes CAAACAGACACCATGGTG-CACCTGACTCCTGAGGA-fluorescein (SEQ ID NO:3) and Cy5-GAAGTCTGCCGTTACTGCCCTGTGGGGCAA G-p (SEQ ID NO: 18) at 0.2 µM each and 0.8 U KlenTaq1 polymerase (a 5'-exonuclease deficient variant of Taq polymerase—U.S. Pat. No. 5,436,149) in a 10 µl reaction. The probes hybridized internal to the primers on the same strand and were immediately adjacent without any intervening bases.

Probes and primers were synthesized by standard phosphoramidite chemistry as known in the art, using a Pharmacia Biotech Gene Assembler Plus (Piscataway, N.J.). The 3'-fluorescein-labeled probe was synthesized on a fluorescein-labeled CPG cassette (Glen Research, Sterling, Va.) with the final trityl-ON to assist with C18 reverse phase HPLC purification. The late eluting peak was collected and the trityl group was removed on a PolyPack (Glen Research). The fluorescein-labeled oligo was eluted with 50% acetonitrile and again purified by C18 reverse phase HPLC. The 5'-Cy5-labeled probe was synthesized with a chemical phosphorylation agent on the 3'-end (Glen Research) and adding a Cy5 amidite (Pharmacia) to the 5'-end during trityl-OFF synthesis. Failure sequences were removed by C18 reverse phase HPLC. Probe purity was checked with polyacrylamide electrophoresis and the absorbance of the dye and the oligo.

HPLC was performed on a 4×250 mm Hypersil ODS column (Hewlett Packard) with a 0.1 M triethanolamine:acetate mobile phase and an acetonitrile gradient at 1 ml/min. The eluate was monitored for both absorbance ($A_{260}$) and fluorescence (490 nm excitation, 520 nm emission for fluorescein and 650 nm excitation, 670 nm emission for Cy5). Tritylated- and fluorescein-labeled oligonucleotides were eluted with a 10-20% acetonitrile gradient, and Cy5-labeled oligonucleotides eluted over a 10-40% acetonitrile gradient.

Figure 9:
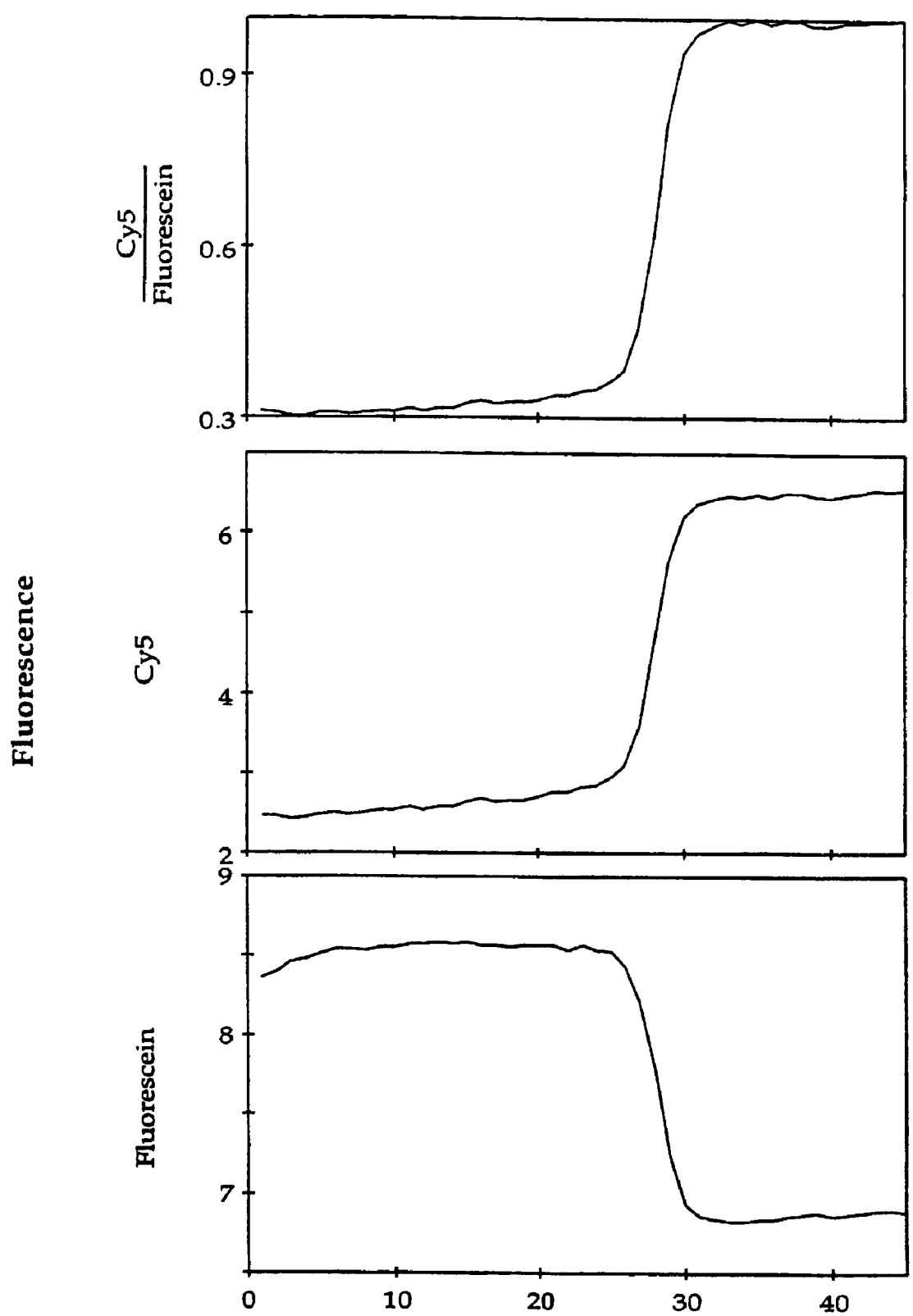
FIG. 9 shows resonance energy transfer occurring between fluorescein- and Cy5-labeled adjacent hybridization probes at each cycle during PCR.

Temperature cycling was 94° C. for 0 sec with a programmed approach rate of 20° C./sec, 60° C. for 20 sec with an approach rate of $2^{0o}$ C./sec, and 75° C. for 0 sec with an approach rate of 1° C./sec in a capillary fluorescence rapid temperature cycler. During temperature cycling, fluorescein and Cy5 fluorescence were acquired each cycle at the end of the annealing/extension segment. Resonance energy transfer was observed as both a decrease in fluorescein fluorescence, and an increase in Cy5 fluorescence beginning around cycle 26 of amplification (FIG. 9). In general, observing the fluorescence ratio of Cy5 to fluorescein fluorescence is preferred.

The unexpectedly good results with the fluorescein/CyS pair can at least partly be rationalized. The overlap integral, $J_{DA}$ depends not only on spectral overlap, but also on the extinction coefficient of the acceptor (Cy5 has an extinction coefficient of 250,000 $M^{-1}cm^{-1}$ at 650 nm), and on the 4th power of the wavelength. Both of these factors will favor a high $J_{DA}$ for CyS, even given low spectral overlap. Recently, phycoerythrin and Cy7 were shown to be an effective tandem probe for immunofluorescence, despite low spectral overlap. In a later example, the utility of fluorescein and Cy5.5 as labels on hybridization probes is demonstrated. Fluorescence resonance energy transfer can be used to monitor nucleic acid hybridization even when the interacting dyes have low spectral overlap. The use of fluorescein with Cy5, Cy5.5 and other red or infrared emitting dyes as resonance energy transfer pairs for monitoring hybridization has not been previously recognized. Fluorescein has a long emission "tail" that goes out to 600 nm, 700 nm and beyond that can be used to excite these far red and infrared dyes. The rate of energy transfer is dependent on the overlap integral, but is also effected by the 6th power of the distance between the fluorophores. If the probes are designed so that the resonance energy transfer dyes are in close proximity, the transfer rate is high. At least with fluorescein/CyS, fluorescein/Cy5.5 and like pairs, resonance energy transfer appears to predominate over collisional quenching and other forms of energy loss when the fluorophores are close together, as in the above example where the fluorophores are attached to adjacent probes with no intervening bases.

The potential usefulness of a resonance energy transfer pair for hybridization probes can be judged by observing the change in the ratio of light intensity in the donor and acceptor windows at minimal and maximal resonance energy transfer. One way to obtain minimal and maximal transfer is to attach both fluorophores to the same oligonucleotide and measure fluorescence ratio before and after digestion with phospodiesterase.

EXAMPLE 4

The dual-labeled fluorescein/Cy5 probe Cy5-CTGCCG-F-TACTGCCCTGTGGGGCAAGGp (SEQ ID NO:19) was synthesized by standard phosphoramidite chemistry, where p is a terminal 3'-phosphate (chemical phosphorylation reagent, Glen Research), F is a fluorescein residue introduced as an amidite with a 2-aminobutyl-1,3-propanediol backbone to maintain the natural 3-carbon internucleotide phosphodiester distance (ClonTech, Palo Alto, Calif.), and Cy5 is added as the amidite (Pharmacia). The ratio of Cy5 to fluorescein fluorescence in 0.1 M Tris, pH 8.0 was obtained before and after exhaustive hydrolysis with phosphodiesterase (Sigma, St. Louis, Mo.). The change in the fluorescence ratio was 220-fold after hydrolysis. A dual-labeled fluorescein/rhodamine probe F-ATGCCCT*CCCCCATGCCATCC TGCGTp (SEQ ID NO:20) was purchased from Perkin Elmer (Foster City, Calif.), where F is fluorescein and * is a rhodamine attached to a modified T residue by an aminolinker arm. The change in the fluorescence ratio (rhodamine to fluorescein) was 22-fold after hydrolysis with phosphodiesterase.

The potential signal from the fluorescein/Cy5 pair was 10-fold that of the fluorescein/rhodamine pair.

EXAMPLE 5

Figure 10:
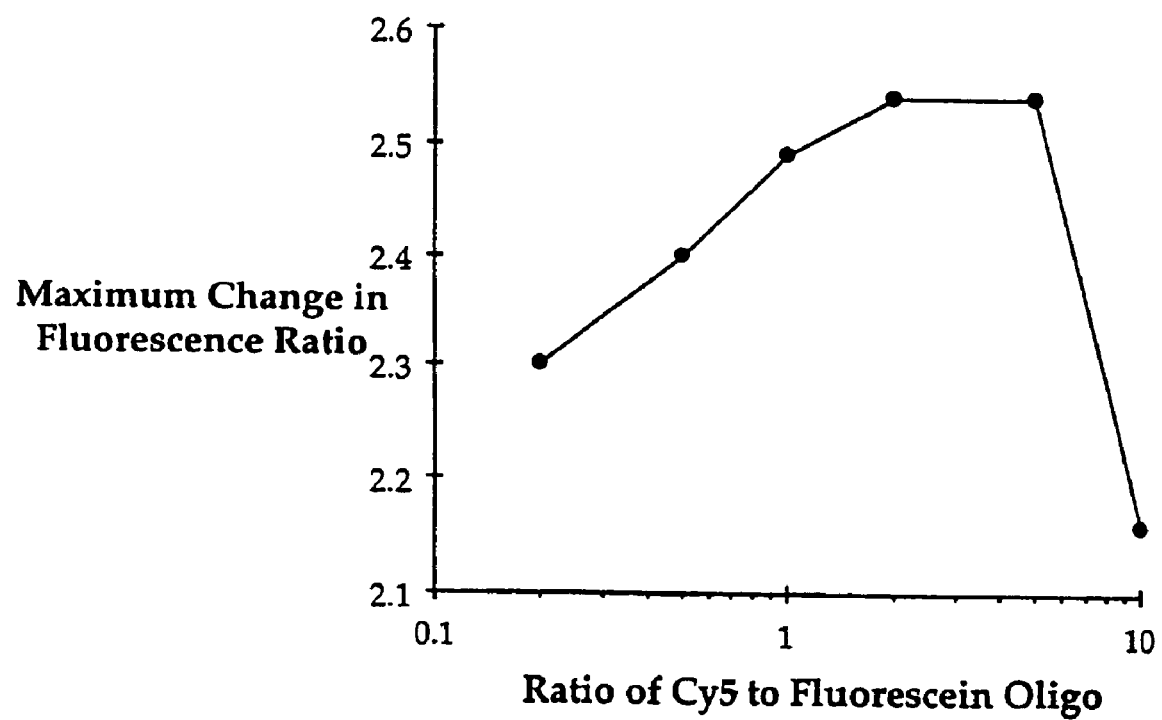
FIG. 10 shows the effect of varying the ratio of the Cy5 probe to the fluorescein probe on the resonance energy transfer signal generated during PCR.
Figure 11:
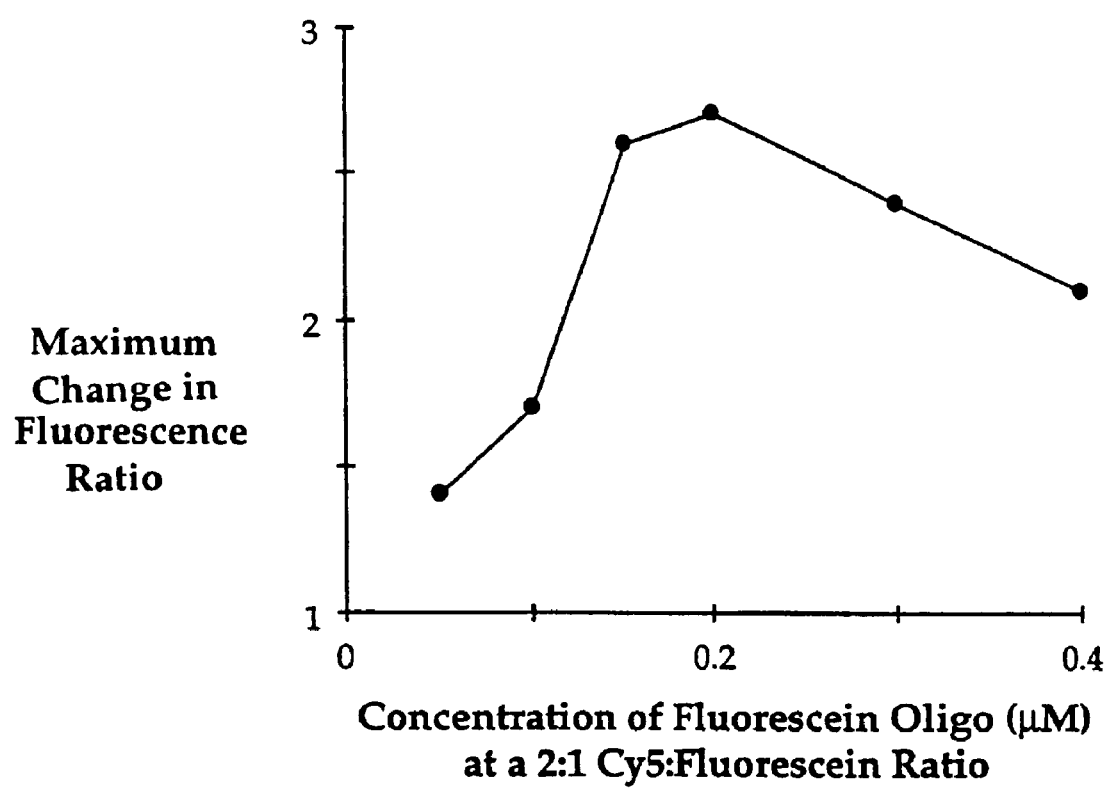
FIG. 11 shows the effect of varying the probe concentration at a given probe ratio on the resonance energy transfer signal generated during PCR.
Figure 12:
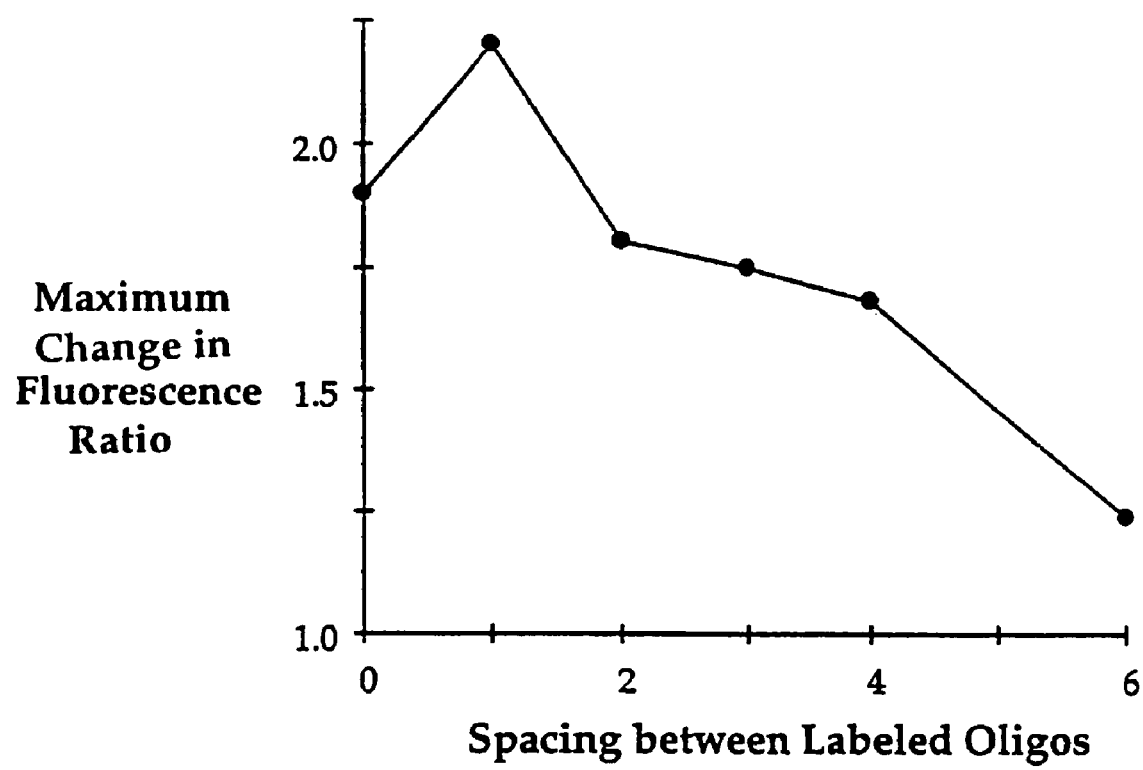
FIG. 12 shows the effect of spacing between the labeled oligonucleotides on the resonance energy transfer signal generated during PCR.

The effect of the ratio, concentration, and spacing of fluorescein and Cy5-labeled adjacent hybridization probes during PCR was studied. Amplification of the beta globin locus and probe pair of Example 3 was used and the maximum change in the fluorescence ratio of Cy5 to fluorescein was observed. The maximal signal occurred when the ratio of Cy5 to fluorescein-labeled probes was 2:1 (FIG. 10). At this 2:1 ratio, the best signal occurred at a fluorescein probe concentration of 0.2 µM and a Cy5-labeled probe concentration of 0.4 µM (FIG. 11). The optimal number of intervening bases between adjacent hybridization probes during PCR was also determined. Several probes of the same length but slightly shifted in their hybridization position were synthesized according to Example 3 so that when they hybridized to the beta globin target, 0, 1, 2, 3, 4, or 6 bases remained between the probes. The highest signal during PCR occurred with one intervening base (FIG. 12). Although some resonance energy transfer was detected at a spacing of 15 and even 25 bases, much better transfer occurred at 0-5 bases.

Heller et al. (U.S. Pat. No. 4,996,143), found that energy transfer efficiency decreased as the number of nucleotides between fluorophores decreased from 4 to 0 units. In contrast, the best energy transfer with the fluorescein/Cy5 pair was seen at 0 to 2 intervening nucleotides.

Hybridization probe method. If 2 probes are synthesized that hybridize adjacently on a target and each is labeled with one fluorophore of a resonance energy transfer pair, the resonance energy transfer increases when hybridization occurs (FIG. 5C). The fluorescein/rhodamine pair is most commonly used for nucleic acid detection.

One aspect of this invention is to provide a sequence-specific homogeneous hybridization method for detection of PCR products. It is not obvious how to achieve this. Using hybridization probes during amplification is counterintuitive. It does not seem that both probe hybridization and polymerase extension can occur. To get sequence specific fluorescence, the probes must be hybridized, but the probes cannot be hybridized if the polymerase is to complete primer extension and exponentially amplify DNA.

One solution to this problem is to use a dual-labeled single probe and utilize the 5'-exonuclease activity of common heat stable DNA polymerases to cleave the probe during extension, thereby separating the 2 fluorophores. In this case, the fluorescence signal arises from separation of the resonance energy transfer pair upon probe hydrolysis (FIG. 5B), rather than approximation of the fluorophores by adjacent hybridization (FIG. 5C). However, dual-labeled probes are difficult to make, requiring manual addition of at least one fluorophore to the oligo and usually require extensive purification. The probes are expensive, and two dual-labeled probes are necessary for competitive quantification of a target or for mutation detection. A further concern is that the observed fluorescence depends on the cumulative amount of probe hydrolyzed, not directly on the amount of product present at any given cycle. This results in a continued increase in fluorescence even after the PCR plateau has been reached. Finally and most importantly, probe hydrolysis does not always occur during polymerase extension, an effect that is not well understood. For example, the dual-labeled fluorescein/Cy5 probe of Example 4 showed very poor hydrolysis during PCR when it was flanked by primers. Indeed, several dual-labeled fluorescein/Cy5 probes, including those with terminal labels, were made and all showed poor hydrolysis and signal generation during amplification.

Homogeneous detection of PCR products with adjacent hybridization probes would solve many of the problems of the 5'-exonuclease system. Synthesis of adjacent hybridization probes is relatively simple because amidites for both fluorescein and Cy5 are available for direct incorporation during automated synthesis and dual labeling of one probe is not required. Because their fluorescence results from hybridization, not hydrolysis, the temperature dependence of probe fluorescence could be used for mutation detection and quantification. However, use of adjacent hybridization probes for homogeneous detection of PCR products has not been reported previously. Surprisingly, both hybridization for signal generation and amplification by polymerase extension through the area blocked by the probes can occur.

EXAMPLE 6

Figure 13:
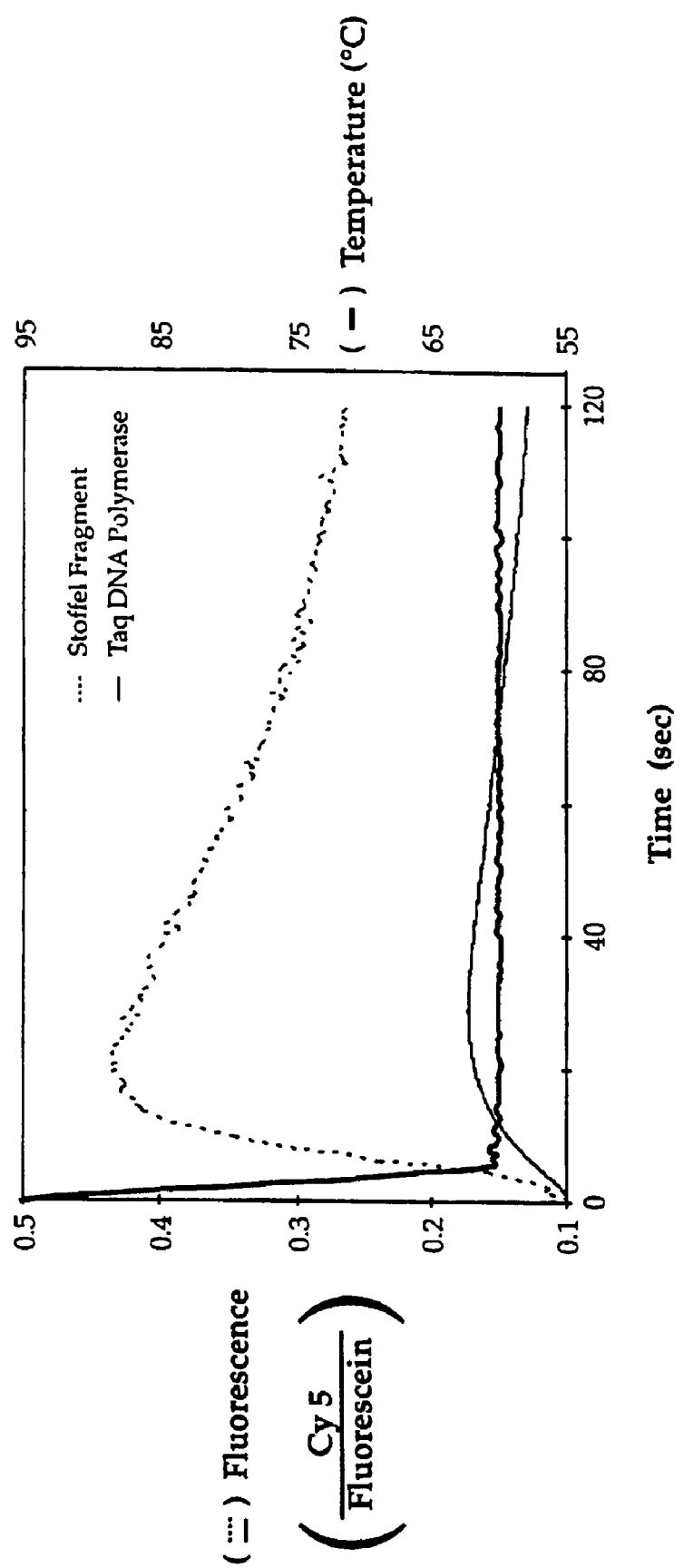
FIG. 13 shows the time course of adjacent probe hybridization by fluorescence energy transfer immediately after 30 cycles of amplification with Taq DNA polymerase (exo$^+$; solid line) and the Stoffel fragment of Taq DNA polymerase (exo$^-$; dotted line) of temperature cycling and the type of polymerase on fluorescence development during PCR with adjacent hybridization probes; temperature is shown with a bold line.

A 110 bp beta-globin fragment was amplified from genomic DNA with adjacent fluorescein- and Cy5-labeled probes as described in Example 3. Either 0.4 U (Taq) or 0.8 U (Stoffel fragment, Perkin Elmer, or KlenTaq1) of enzyme was used in 10 µl reactions. Unless indicated otherwise, temperature cycling was 94° C. for 0 sec with a programmed approach rate of 20° C./sec, 60° C. for 20 sec with an approach rate of 20° C./sec, and 75° C. for 0 sec with an approach rate of 1° C./sec. FIG. 13 shows the development of fluorescence by 2 adjacent hybridization probes immediately after the template was amplified for 30 cycles. After a brief denaturation at 94° C., the temperature was lowered to 60° C. and fluorescence increased for about 20 sec. The magnitude of the signal is greater with an exonuclease deficient polymerase (Stoffel fragment) than with native Taq polymerase that includes a 5'-exonuclease activity. After about 20 sec., the fluorescence drops as the polymerase displaces and/or hydrolyzes the probes. The relative decrease in fluorescence is slightly faster when the polymerase has 5'-exonuclease activity (Taq DNA polymerase) then when it lacks this activity (Stoffel fragment).

Figure 14:
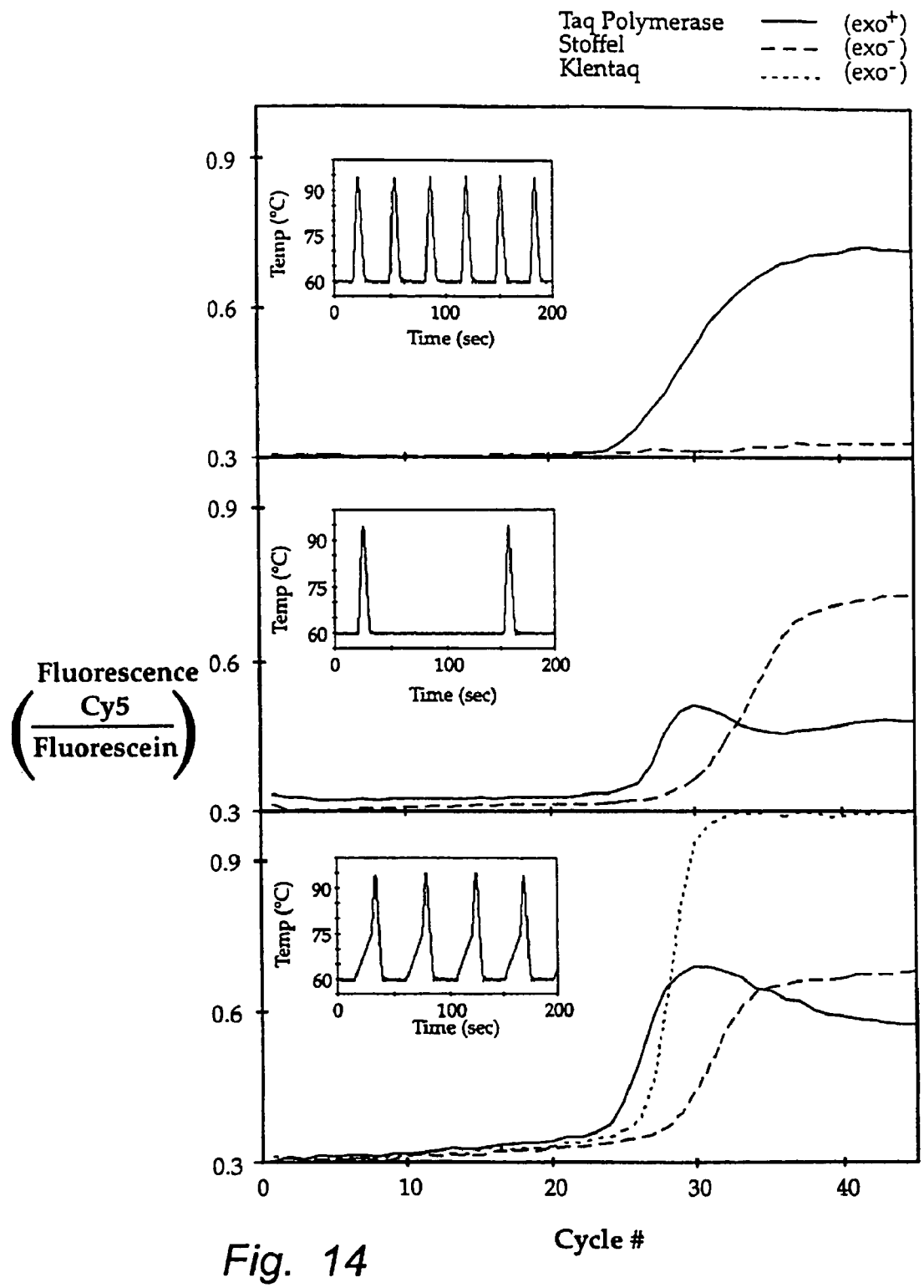
FIG. 14 is a fluorescence ratio v. cycle number plot for amplification with Taq DNA polymerase (exo$^+$; solid line), Stoffel fragment of Taq DNA polymerase (exo$^-$; broken line), and KlenTaq DNA polymerase (exo$^-$; dotted line): top panel—cycling is between 94° C. and 60° C. with a 20 second hold at 60° C.; middle panel—cycling is between 94° C. and 60° C. with a 120 second hold at 60° C.; bottom panel—cycling is between 94° C. and 60° C. with a slow increase from 60° C. to 75° C.

In FIG. 14 (top panel), the temperature is cycled between 94° C. and 60° C. with a 20 sec hold at 60° C. Fluorescence is acquired at the end of the 20 sec when fluorescence is maximal. Good amplification occurs with Taq (exo$^+$), but not with Stoffel fragment (exo$^-$) as verified by both fluorescence development and agarose gels (gels not shown). However, if the time at 60° C. is increased from 20 sec to 120 sec (FIG. 14, middle panel), the exo$^-$ polymerase amplifies well. The slower rate of probe displacement with an exo$^-$ polymerase apparently requires more time at 60° C. for efficient amplification than the exo$^+$ polymerase. The time required by exo$^-$ polymerases can be reduced by slowly increasing the temperature from 60° C. to 75° C. (FIG. 14, bottom panel). The polymerase stalls when it reaches the probe. However, at the probe melting temperatures, the probes melt off the template and the polymerase continues unencumbered to complete polymerization of the strand. Polymerization is completed as long as the temperature is not raised too quickly after probe melting. FIG. 14 (bottom panel) shows one exo$^+$ polymerase (Taq) and two exo$^-$ polymerases (Stoffel fragment and KlenTaq1).

When exonuclease activity is present, some of the probe is hydrolyzed each cycle as evidenced by an the decrease in fluorescence with extensive amplification. This is observed in FIGS. 13 and 14 (middle and bottom panels), but is does not occur with exo⁻ polymerases. Because the fluorescence is stable on extensive amplification, exo⁻ polymerases such as KlenTaq1 are preferred.

The success of using adjacent hybridization probes to monitor PCR depends on several factors. Resonance energy transfer is maximized when there is either 0 to 2 intervening bases between adjacent hybridization probes. To increase the fraction of strands that hybridize to the probes before the primer extends through the area of probe hybridization, the probe melting temperatures should be greater than the primer melting temperatures (preferably >5° C.).

Cycle-by-cycle fluorescence. Conventional endpoint analysis of DNA amplification by gel electrophoresis identifies product size and estimates purity. However, because amplification is at first stochastic, then exponential, and finally stagnant, the utility of endpoint analysis is limited for quantification. One aspect of the present invention includes cycle-by-cycle monitoring for quantification of initial template copy number with hybridization probes. As will be appreciated by those skilled in the art, once-per-cycle monitoring of multiple samples undergoing DNA amplification is a powerful quantitative tool. Cycle-by-cycle monitoring is achieved by acquiring fluorescence during the extension or combined annealing/extension phase of each cycle and relating the fluorescence to product concentration.

EXAMPLE 7

Cycle-by-cycle monitoring of PCR was performed by three different fluorescence techniques. Fluorescence was monitored by (i) the double-strand-specific dye SYBR™ Green I, (ii) a decrease in fluorescein quenching by rhodamine after exonuclease cleavage of a dual-labeled hydrolysis probe and (iii) resonance energy transfer of fluorescein to Cy5 by adjacent hybridization probes. Amplification reagents and conditions were as described in Example 2. The human beta-globin primers RS42/KM29 (536 base pairs) and PC03/PC04 (110 base pairs) are described in C. T. Wittwer et al., Automated polymerase chain reaction in capillary tubes with hot air, 17 Nucl. Acids. Res. 4353-4357 (1989), which is now incorporated herein by reference. Temperature cycling for beta-globin was 95° C. maximum, 61° C. minimum, 15 sec at 72° C. and an average rate between temperatures of 5.2° C./sec. The beta-actin primers and fluorescein/rhodamine dual probe were obtained from Perkin Elmer (no. N808-0230). Temperature cycling for beta-actin was 94° C. maximum, 60° C. for 15 sec with an average rate between temperatures of 6.2° C./sec. The single labeled probes 5'-CAAACAGACACCATGGTGCACCTGACTC-CTGAGGA-fluorescein-3' (SEQ ID NO:3) and 5'-Cy5-AAGTCTGCCGTTACTGCCCTGTGGGGCAAGp (SEQ ID NO:4) were synthesized as in Example 3. These adjacent probes hybridize internal to the PC03/PC04 beta-globin primer pair on the same DNA strand and are separated by one base pair. Temperature cycling was 94° C. maximum, 59° C. for 20 sec with an average rate between temperatures of 7.0° C./sec. Hybridization probes (beta-actin and beta-globin) were used at 0.2 μM each.

Figure 15:
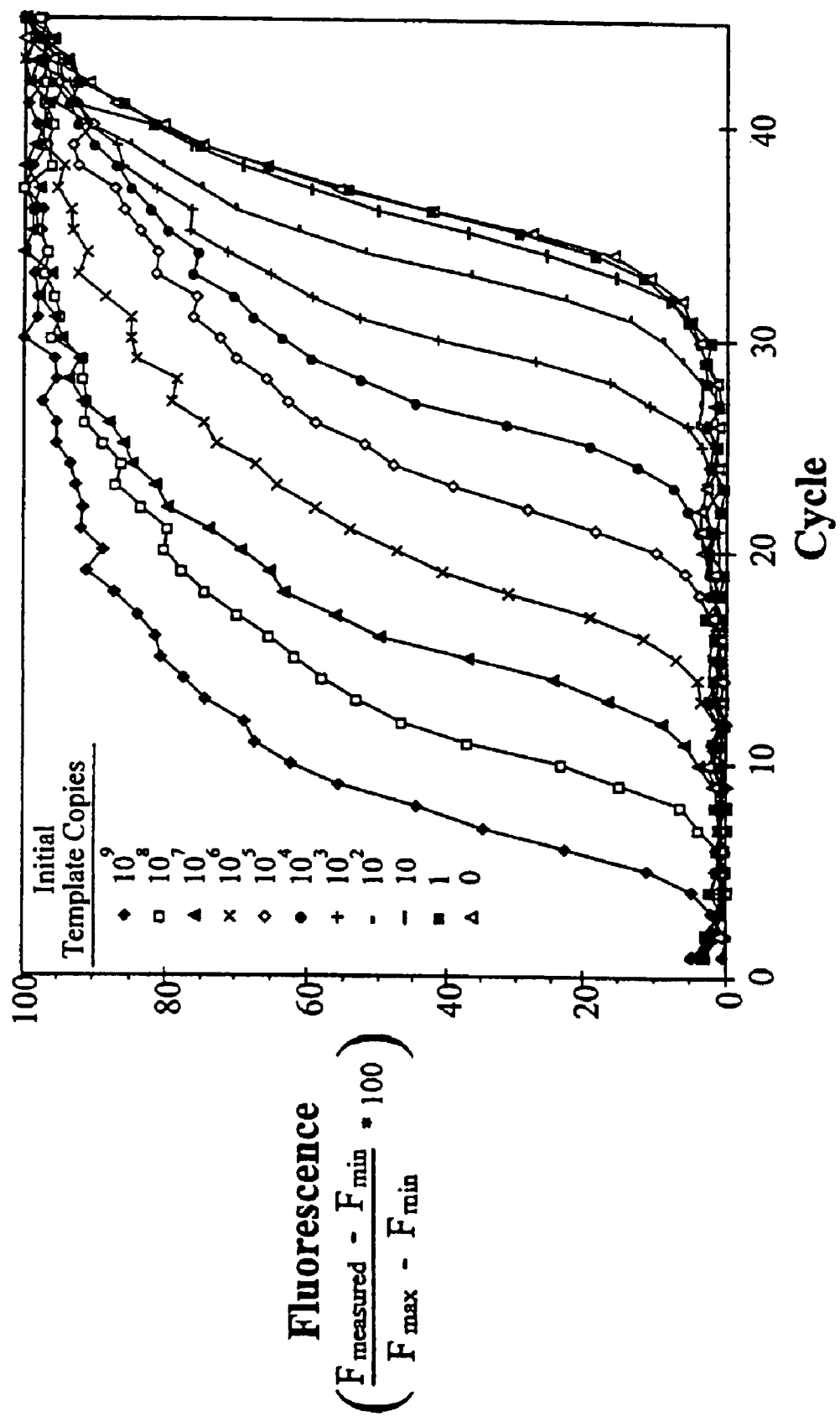
FIG. 15 is a fluorescence v. cycle number plot for a number of different initial template copy reactions monitored with Sybr™ Green I: 0, (Δ); 1, (■); 10, (—); $10^2$, (-); $10^3$, (+); $10^4$, (●); $10^5$, (◇); $10^6$, (×); $10^7$, (▲); $10^8$, (□); $10^9$, (◆).

When multiple samples are monitored once each cycle with SYBR™ Green I, a 10⁷-10⁸ range of initial template concentration can be discerned as represented in FIG. 15. This amplification is of a 536 base pair fragment of the beta-globin gene, with SYBR™ Green I as the double-strand specific dye. When the data were normalized as the percent of maximal fluorescence of each sample, one hundred initial copies were clearly separated from ten copies. However, the difference between one and ten copies was marginal, and no difference was observed between zero and one average copies per sample.

Figure 16:
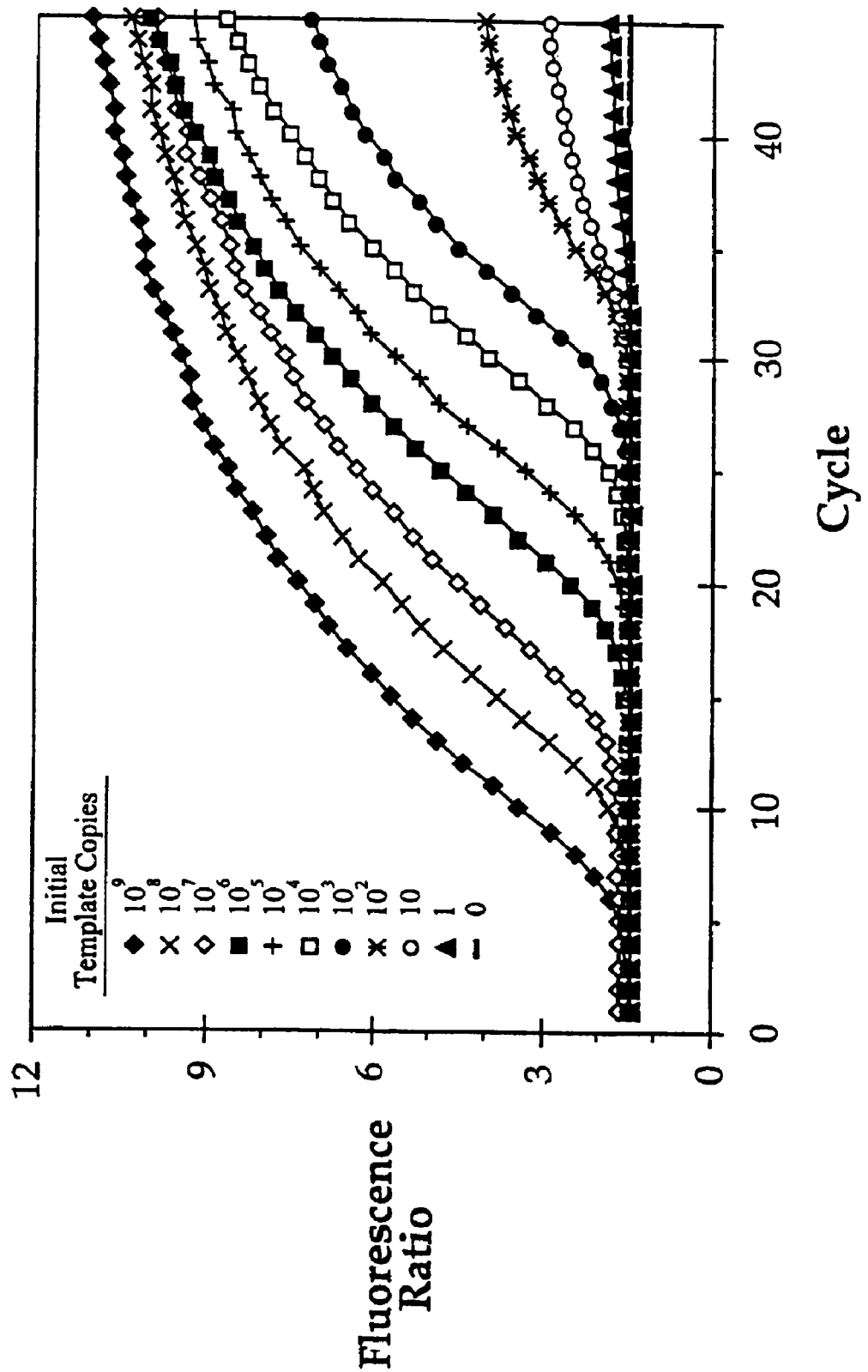
FIG. 16 is a fluorescence ratio v. cycle number plot for a number of different initial template copy reactions monitored with a dual-labeled hydrolysis probe: 0, (-); 1, (▲); 10, (○); $10^2$, (*); $10^3$, (●); $10^4$, (□); $10^5$, (+); $10^6$, (■); $10^7$, (◇); $10^8$, (×); $10^9$, (◆).

In contrast, sequence-specific probes have a similar dynamic range but, appear to discriminate even a single initial template copy from negative controls. Signal generation with 5'-exonuclease probes (beta-actin fragment, FIG. 16) is dependent not only on DNA synthesis, but requires hybridization and hydrolysis between the fluorophores of the dual-labeled probe. This hydrolysis reduces quenching and the fluorescence ratio of fluorescein to rhodamine emission increases. Whereas the fluorescence from double strand dyes levels off with excess cycling (FIG. 15), the signal from exonuclease probes continues to increase with each cycle (FIG. 16). Even though no net product is being synthesized, probe hybridization and hydrolysis continue to occur. As the template copy number decreases below 10³, signal intensity decreases, but low copy numbers can still be quantified because the negative control signal is stable.

Figure 17:
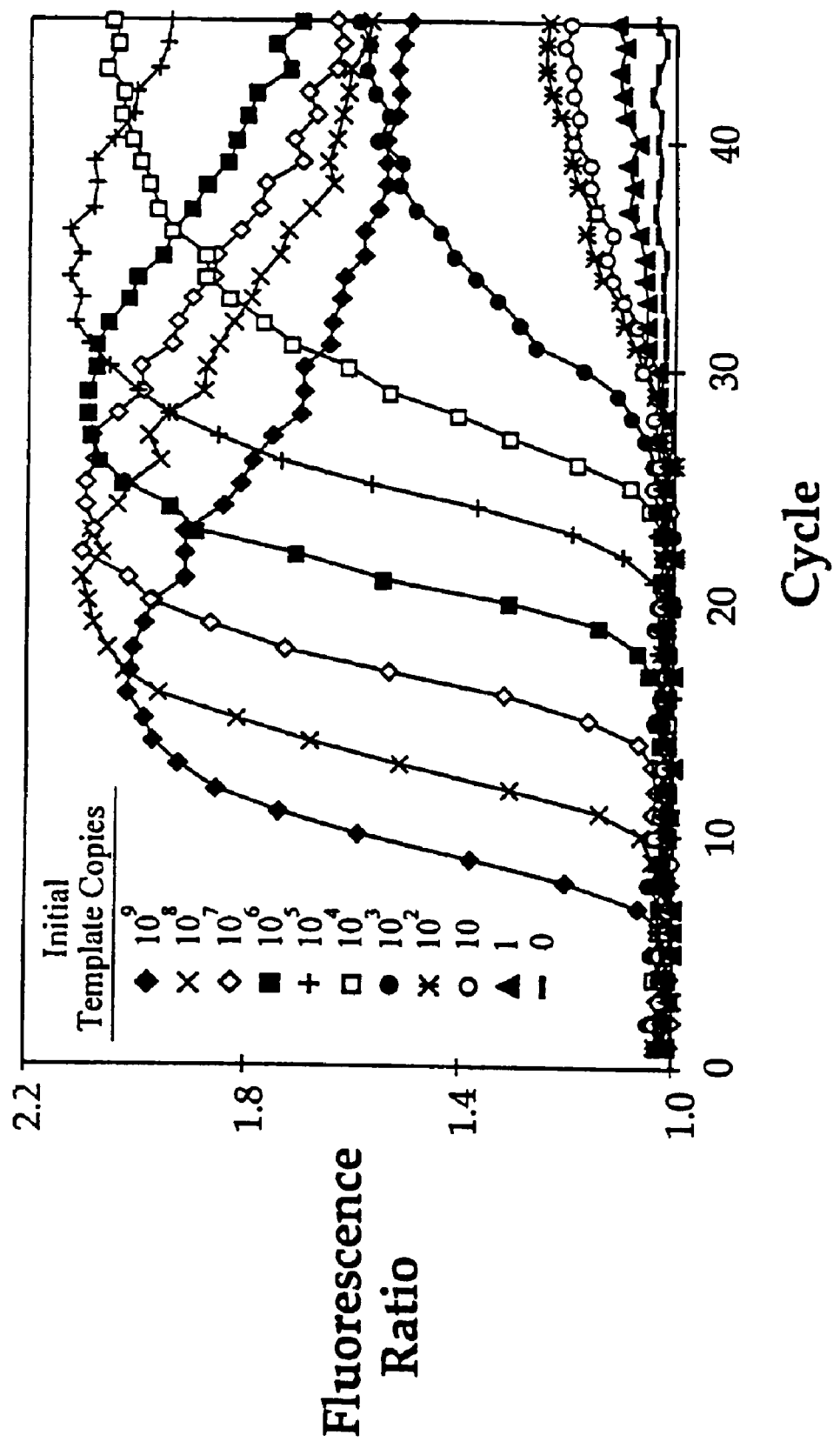
FIG. 17 is a fluorescence ratio v. cycle number plot for a number of different initial template copy reactions monitored with adjacent hybridization probes: 0, (-); 1, (▲); 10, (○); $10^2$, (*); $10^3$, (●); $10^4$, (□); $10^5$, (+); $10^6$, (■); $10^7$, (◇); $10^8$, (×); $10^9$, (◆).

In FIG. 17, amplification is monitored using adjacent hybridization probes and is expressed as a ratio of Cy5 to fluorescein fluorescence. The change in fluorescence ratio is largely due to an increase in Cy5 fluorescence from resonance energy transfer (FIG. 9). In contrast to dual-labeled hydrolysis probes, the fluorescence signal of hybridization probes decreases at high cycle numbers if the polymerase contains an exonuclease activity (see also FIG. 14).

The present invention's feasibility using two different methods for resonance energy transfer detection of hybridization during PCR will now be demonstrated. The first method uses two adjacent hybridization probes, one labeled 3' with fluorescein and the other labeled 5' with Cy5. As product accumulates during PCR, the probes hybridize next to each other during the annealing segment of each cycle. The second method uses a primer labeled with Cy5 and a single hybridization probe. The labeled primer is incorporated into the PCR product during amplification and only a single hybridization is necessary.

EXAMPLE 8

Cycle-by-cycle monitoring of PCR was performed by resonance energy transfer between a Cy5-labeled primer and a fluorescein-labeled hybridization probe. This was compared to monitoring with adjacent Cy5/fluorescein hybridization probes. The Cy5-labeled primer was CAACTTCATCCACGT*TCACC (SEQ ID NO:21) where T* is a modified T base with Cy5 attached and the corresponding probe was GTCTGCCGTTACTGCCCT-GTGGGGCAA-fluorescein (SEQ ID NO:22). The adjacent hybridization probes were CCTCAAACAGACACCATG-GTGCACCTGACTCC-fluorescein (SEQ ID NO:23) and Cy5-GAAGTCTGCCGTTACTGCCCTGTGGGGCAAp (SEQ ID NO:24). The hybridization probes were synthesized according to Example 3 and used at 0.2 μM. The Cy5-labeled primer was synthesized in two steps. Automated synthesis was used to incorporate an amino-modifier C6dT (Glen Research) at the desired T position. Then, the monovalent N-hydroxysuccinimide ester of Cy5 (FIG. 6) was manually conjugated to the amino linker according to the manufacturer's instructions (Amersham). HPLC purification was as described in Example 3.

Figure 18:
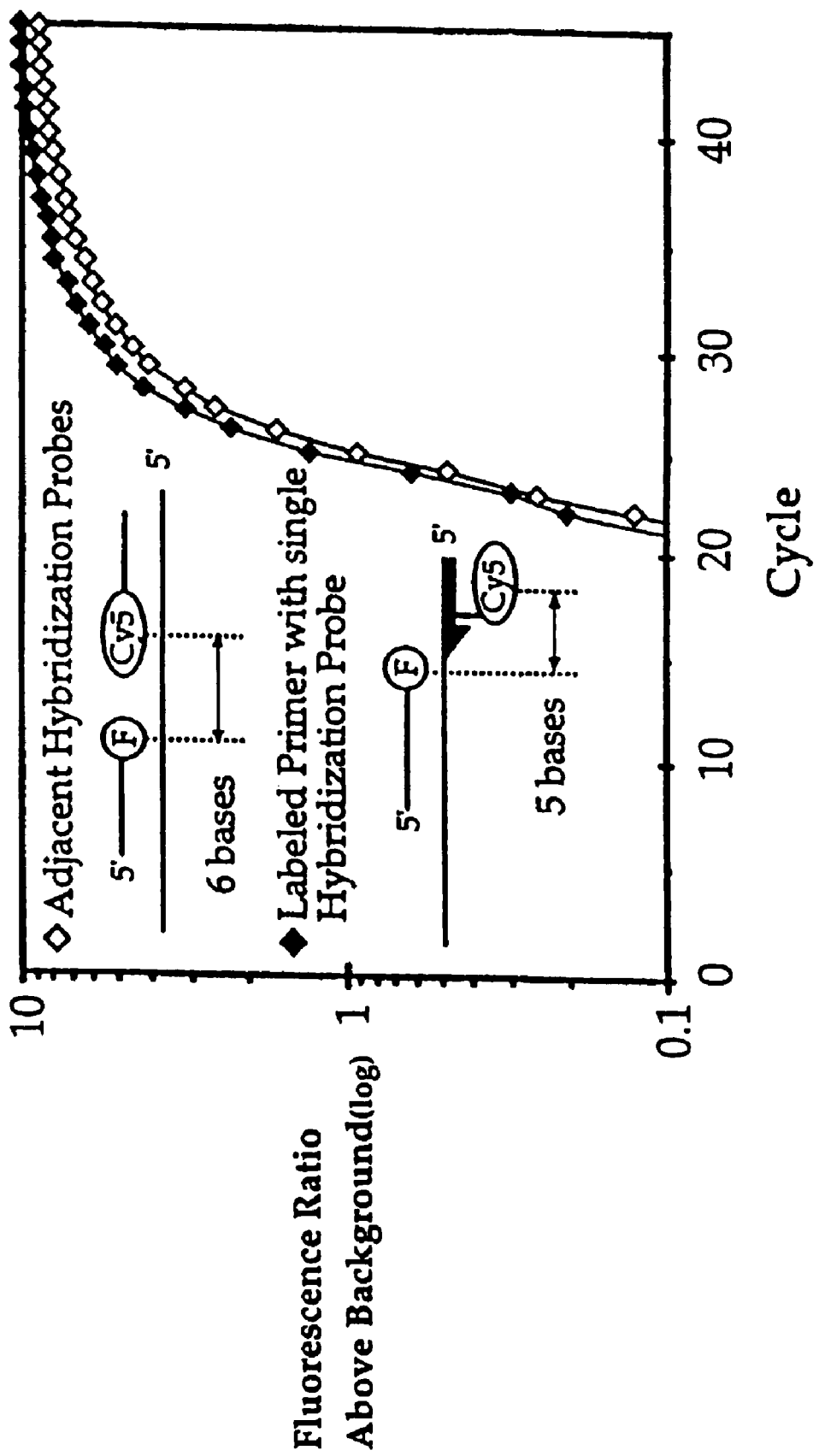
FIG. 18 is a fluorescence ratio v. cycle number plot distinguishing two hybridization probe designs monitored by resonance energy transfer: (◇) two hybridization probes labeled respectively with fluorescein and Cy5; and (◆) a primer labeled with Cy5 and a probe labeled with fluorescein.

The Cy5-labeled primer (0.5 μM) was used instead of PCO4 to amplify the 110 base pair beta-globin fragment from human genomic DNA as in Example 3, except that 0.4 U of Taq polymerase was used per 10 μl. The adjacent hybridization probes also monitored amplification of the same beta-globin fragment. Temperature cycling was done at 94° C. for 0 sec and 60° C. for 20 sec. The fluorescence was monitored once each cycle at the end of the annealing/extension segment. In both methods, fluorescence energy transfer to Cy5 increases with hybridization and is plotted as a ratio of Cy5 to fluorescein fluorescence (FIG. 18).

In additional experiments, the number of bases separating the Cy5-label and the fluorescein label were varied. The best fluorescence resonance energy transfer was observed with about 4-6 bases between the fluorophores, although a signal was detectable up to at least 15 bases.

In contrast to hydrolysis probes, the fluorescence signal from hybridization probes is not cumulative and develops anew during each annealing phase. The fluorescence is a direct measure of product concentration because the hybridization is a pseudo-first order reaction. Because the concentration of probe is much greater than the product, the fraction of product hybridized to probe is independent of product concentration. These characteristics indicate that using a single hybridization probe along with a labeled primer will provide a superior monitor of product accumulation for quantification. The inherent variance of different fluorescence techniques during cycle-by-cycle monitoring is also important for quantification.

EXAMPLE 9

DNA amplification was performed according to Example 2 for each of three different fluorescence monitoring methods. SYBR™ Green I was used at a 1:10,000 dilution in the amplification of a 205 base pair human beta-globin fragment from primers KM29 and PC04. The hydrolysis probe and conditions are those specified in Example 7. The hybridization probe, TCTGCCGTTACTGCCCTGTGGGGCAAG-fluorescein (SEQ ID NO:5) was used with KM29 and the Cy5-labeled primer CAACTTCATCCACGTT*CACC (SEQ ID NO:6) where T* was a Cy5-labeled T base synthesized as in example 8. All amplifications were performed in ten replicates with 15,000 template copies (50 ng of human genomic DNA/10 µl). The temperature cycles were 31 sec long (94° C. maximum, 60° C. for 20 sec, average rate between temperatures 6.2° C./sec). Fluorescence was acquired for each sample between seconds 15 and 20 of the annealing/extension phase.

FIG. 19 allows comparison of three fluorescence monitoring techniques for PCR. The fluorescence probes are the dsDNA dye SYBR™ Green I (FIG. 19A), a dual-labeled fluorescein/rhodamine hydrolysis probe (FIG. 19B), and a fluorescein-labeled hybridization probe with a Cy5-labeled primer (FIG. 19C). All probes had nearly the same sensitivity with detectable fluorescence occurring around cycle 20. With extended amplification, the signal continued to increase with the hydrolysis probe, was level with SYBR™ Green I, and slightly decreased with the hybridization probe. The precision of the three fluorescence monitoring techniques are compared in FIG. 19D. The mean± standard deviations are plotted for each point. The data are plotted as the coefficient of variation (standard deviation/mean) of the fluorescence ratio above baseline (taken as the average of cycles 11-15).

Figure 19A:
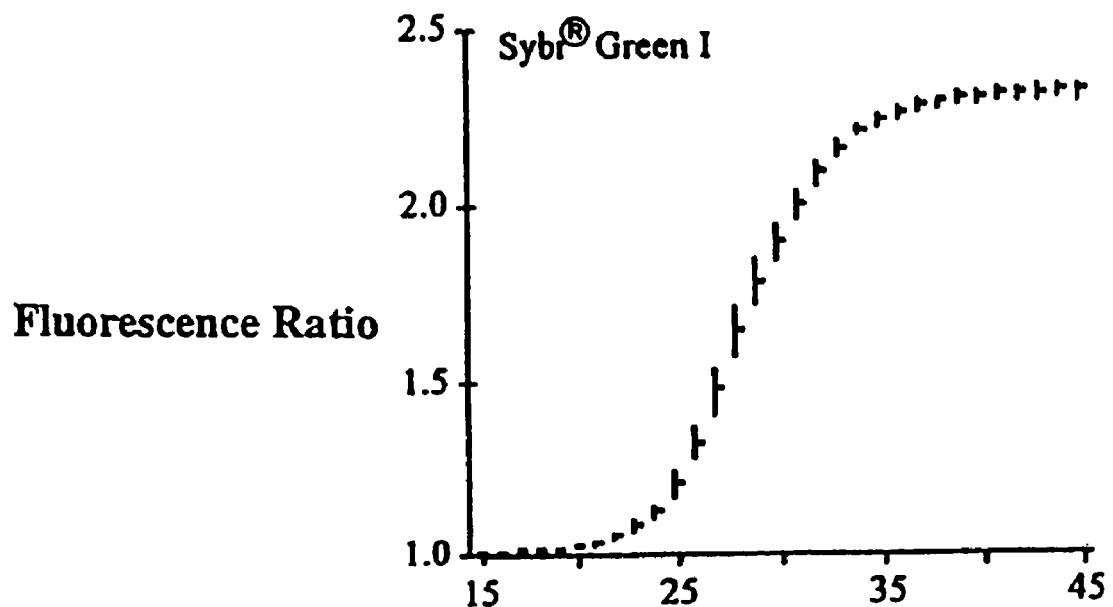
FIGS. 19A-C provide a comparison of three fluorescence monitoring techniques for PCR, including the double-strand specific DNA dye SYBR Green I (A), a dual-labeled fluorescein/rhodamine hydrolysis probe (B), and a fluorescein-labeled hybridization probe with a Cy5-labeled primer (C)
Figure 19B:
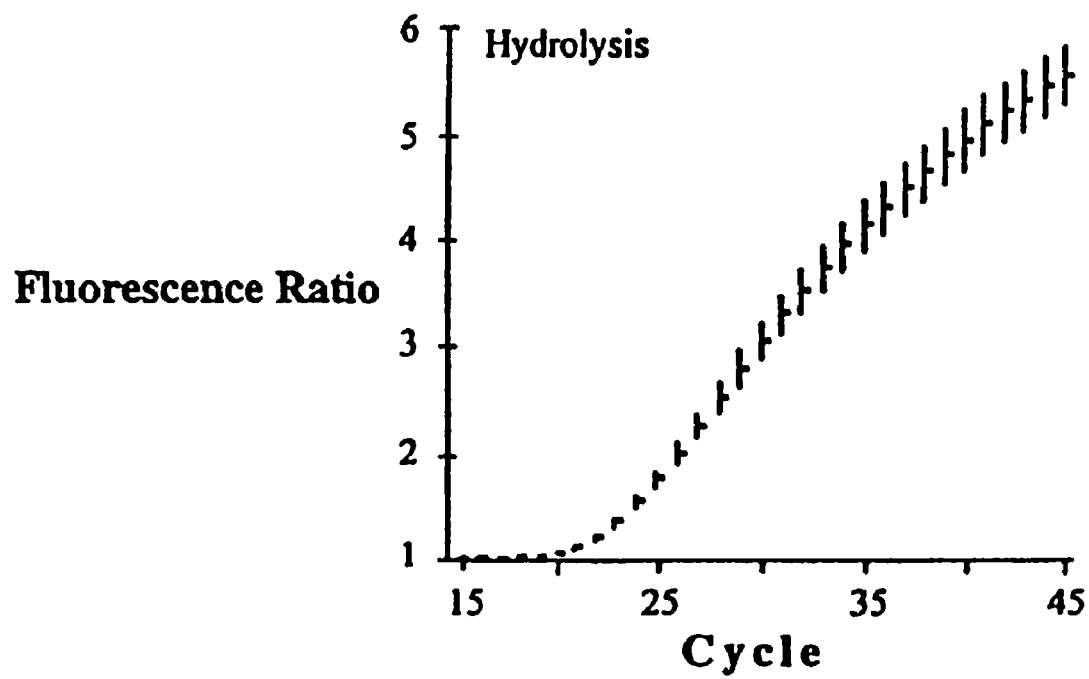
Figure 19C:
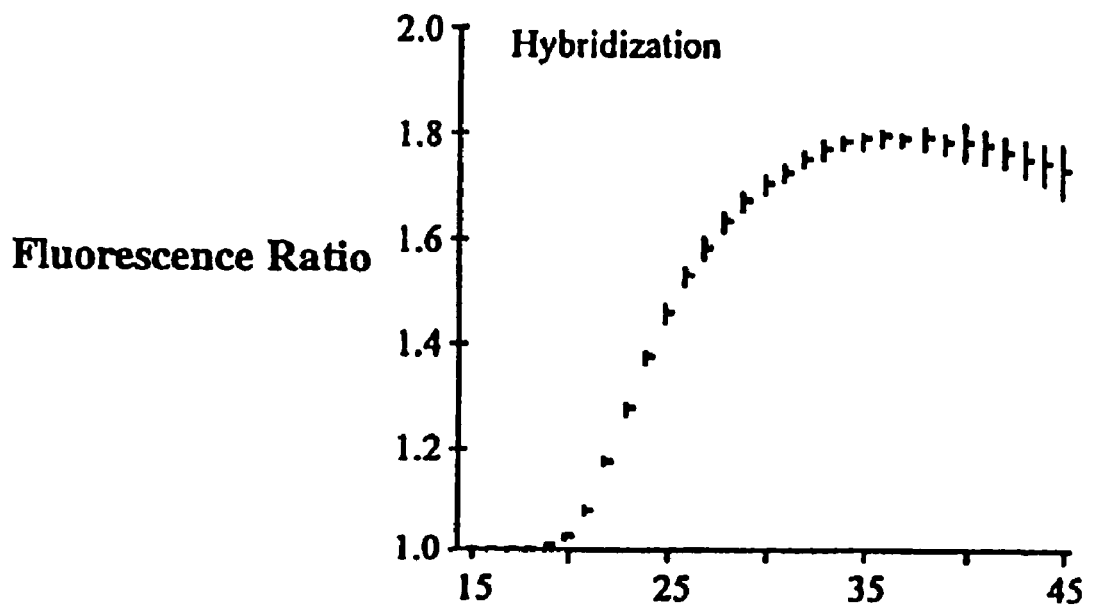
Figure 19D:
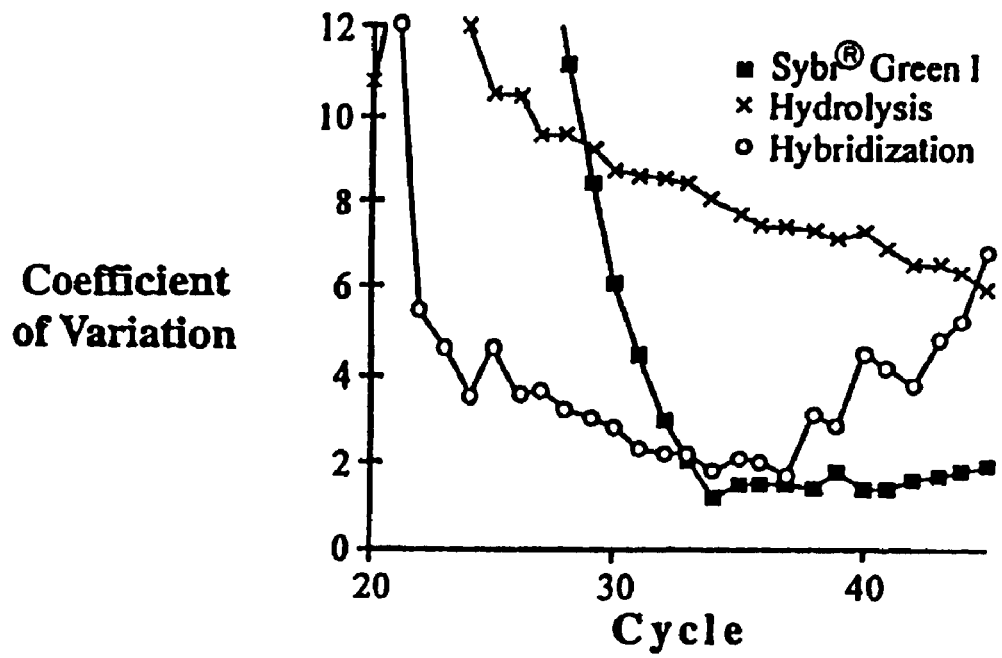
FIG. 19D shows the coefficient of variation for the three monitoring techniques represented in FIGS. 19A-C.

Although the change in fluorescence ratio from the hydrolysis probe is greater than that from the hybridization probe (FIGS. 19B and 19C), the coefficient of variation of fluorescence from the hydrolysis probes is greater (FIG. 19D). That is, the fluorescence resulting from the hybridization probe method is more precise than using a hydrolysis probe, even though the absolute signal levels are lower. This is an unexpected advantage of hybridization probes over the more usual dual-labeled hydrolysis probes.

Quantification of initial template copy number. Quantitative PCR has become an important technique in both biomedical research and in the clinical laboratory. The process of quantification often includes running a standard curve of samples containing known copy numbers of the target sequence. The copy number of an unknown sample is determined by extrapolation between the known values. When a complete amplification curve is monitored cycle-by-cycle using fluorescence, radioactivity or any other method that gives a signal proportional to the amount of DNA present, many data points are available for analysis and it is not obvious which value to choose to represent a standard or unknown. Prior art is to choose a "threshold value" of the signal and then use the cycle number when the standard or unknown crosses that threshold as the representative value (see Higuchi & Watson, EPA 0 640 828 A1). This approach uses a very small amount of the available data in an amplification curve. In addition, the assignment of the threshold value is highly subjective and is subject to conscious or unconscious bias. More of the available data could be used objectively by applying non-linear curve fitting techniques to the data in an amplification curve. Preferably, equations could be found that describe the shape of the amplification curves by modeling factors of the underlying process.

A number of different equations could be used to fit the data produced during amplification. DNA amplifications typically have a log linear segment and the data in this segment can be fit to an equation that describes an exponential increase like that expected in a DNA amplification. The log-linear portion of a DNA amplification can be described by the equation:

$$y = A*[DNA]*(1+E)^n$$

wherein A is a scaling factor that converts units of signal to units of DNA; [DNA] is the starting concentration of DNA in the reaction;

E is the efficiency of the reaction; and n is the cycle number.

Figure 20:
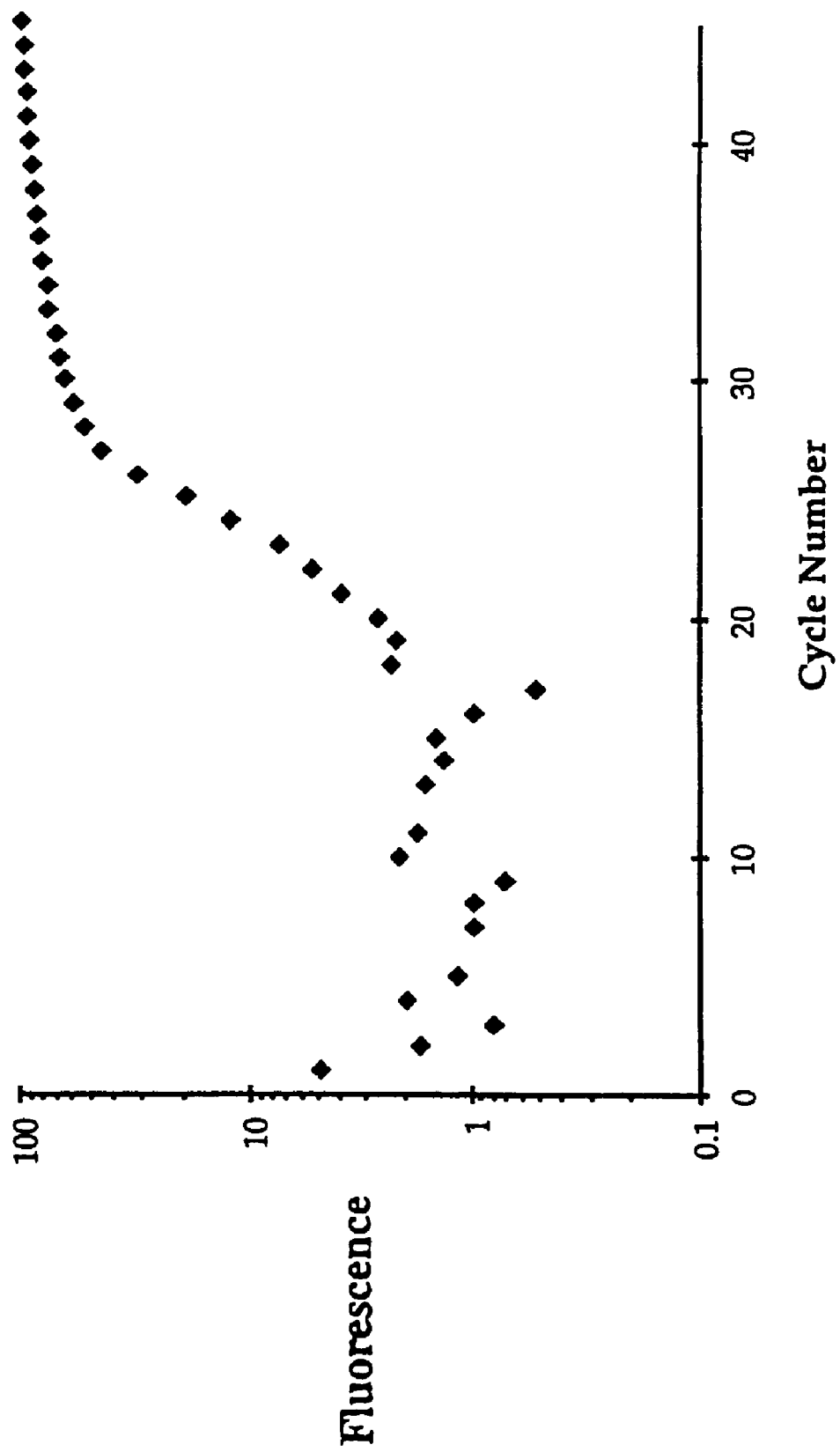
FIG. 20 shows a typical log fluorescence vs cycle number plot of a standard amplification monitored with SYBR Green I.
Figure 21:
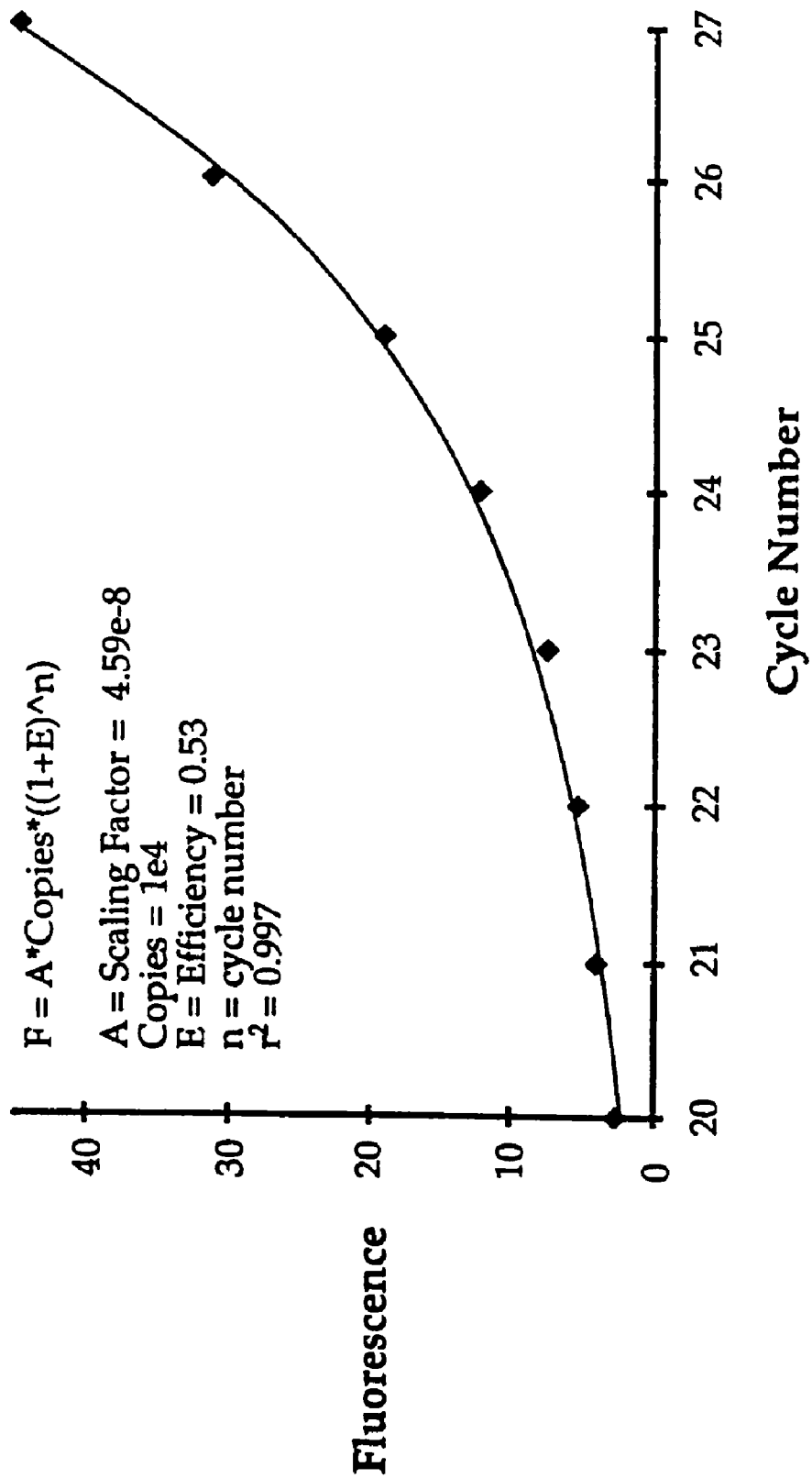
FIG. 21 shows an exponential curve fit to cycles 20-27 of the data from FIG. 20.
Figure 22:
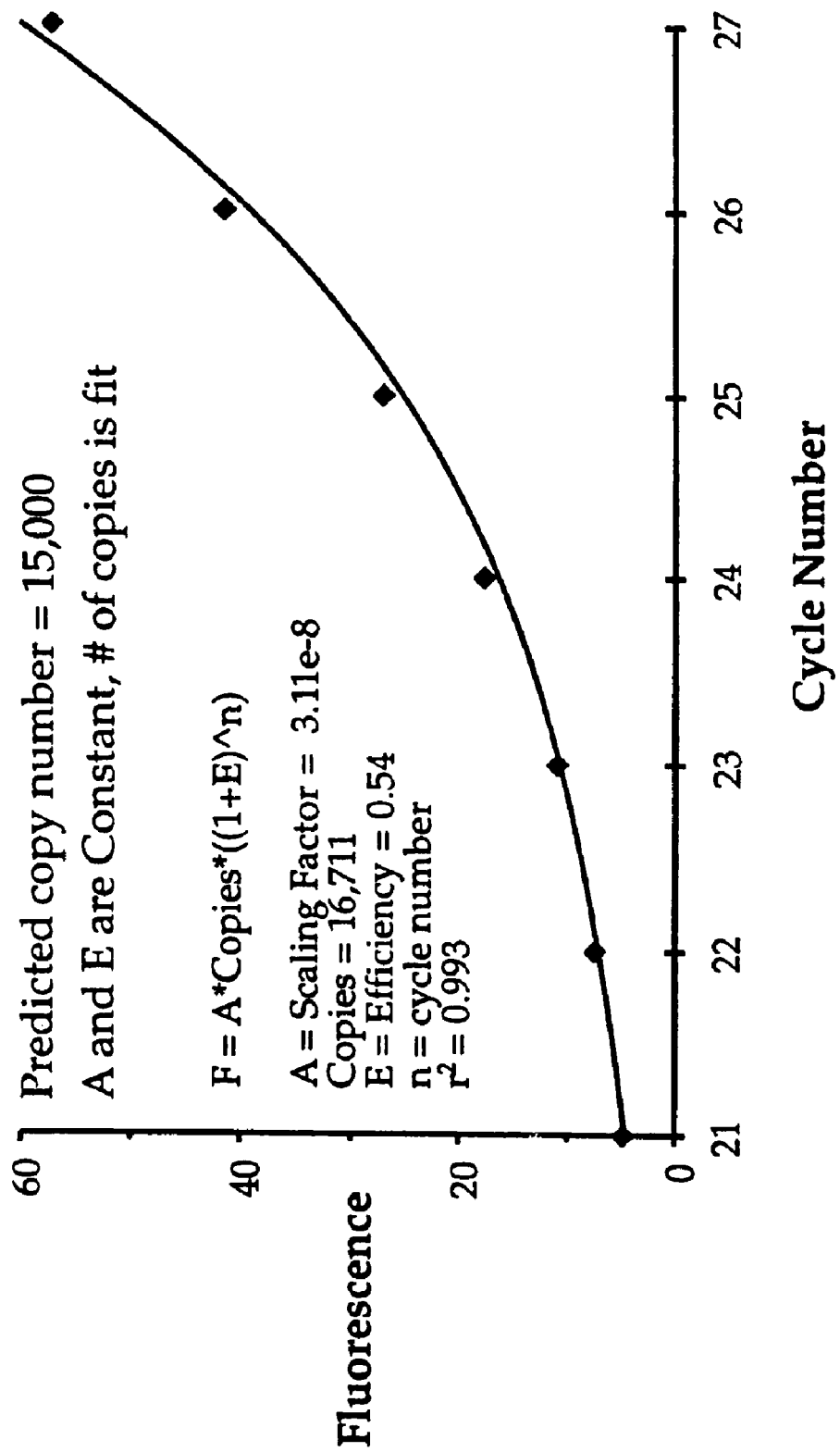
FIG. 22 shows an exponential fit to an unknown to determine initial copy number from amplification data.

A quantification process would involve: (1) fitting the known standards to this equation allowing the parameters A and E to float, and (2) fitting the unknown samples to the equation using the values of A and E from the standards and allowing [DNA] to float. This technique uses much more of the data and uses the portion of the data, the log-linear portion, that is likely to be most informative. FIGS. 20, 21 and 22 show an example of this approach. Ten-fold dilutions of a purified PCR product were amplified as a standard curve and an "unknown" human genomic DNA standard was used. FIG. 20 shows that the log-linear portion is easily identified either by the user or by software. FIG. 21 shows a fit of the equation $y=A*[DNA]*(1+E)^n$ to the $10^4$ copy standard. FIG. 22 uses average values from several standards for A and E and fits [DNA]. The fit value of 16,700 is very close to the theoretical value for a single copy gene in genomic DNA (15,000 copies).

Figure 23:
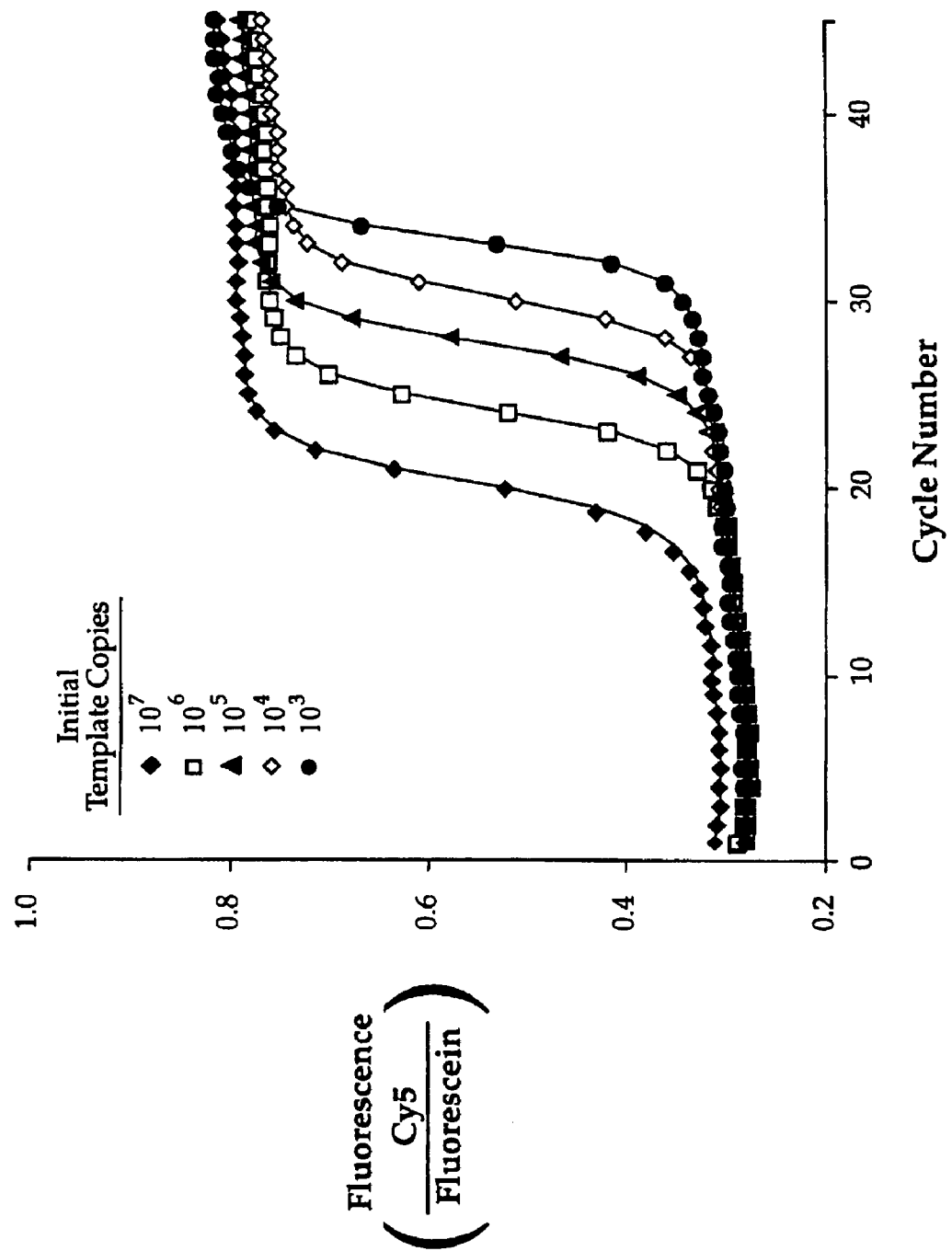
FIG. 23 shows a typical fluorescence v. cycle number plot of five standards monitored each cycle with adjacent hybridization probes, wherein initial copy numbers are represented as follows: $10^3$, (●); $10^4$, (◇); $10^5$, (▲); $10^6$, (□); $10^7$, (◆).

Using all the data in an amplification curve would include the background level and the plateau value. While at high copy number the plateau is uninformative, at low copy number it is often proportional to starting copy number. The background level could be useful in determining the first point that shows a significant increase in signal. At this time all the factors involved in the shape of the DNA amplification curve are not known, so one approach is to describe the shape of the curve. FIG. 23 shows amplification curves using fluorescent hybridization probes to detect a five order of magnitude range of DNA template concentrations. Each curve is fit to the equation:

$$y=((as*x+ab)-(ds*x+db))/(1+(x/c)\hat{}b)+(ds*x+db)$$

wherein "as" is the background of the slope line, "ab" is the y intercept of the background line, "ds" is the slope of the plateau line, "db" is the y intercept of the slope line, "c" is cycle number where the reaction is halfway from background to plateau ($A_{50}$), and "b" is the slope of the log-linear portion of the amplification.

Figure 24:
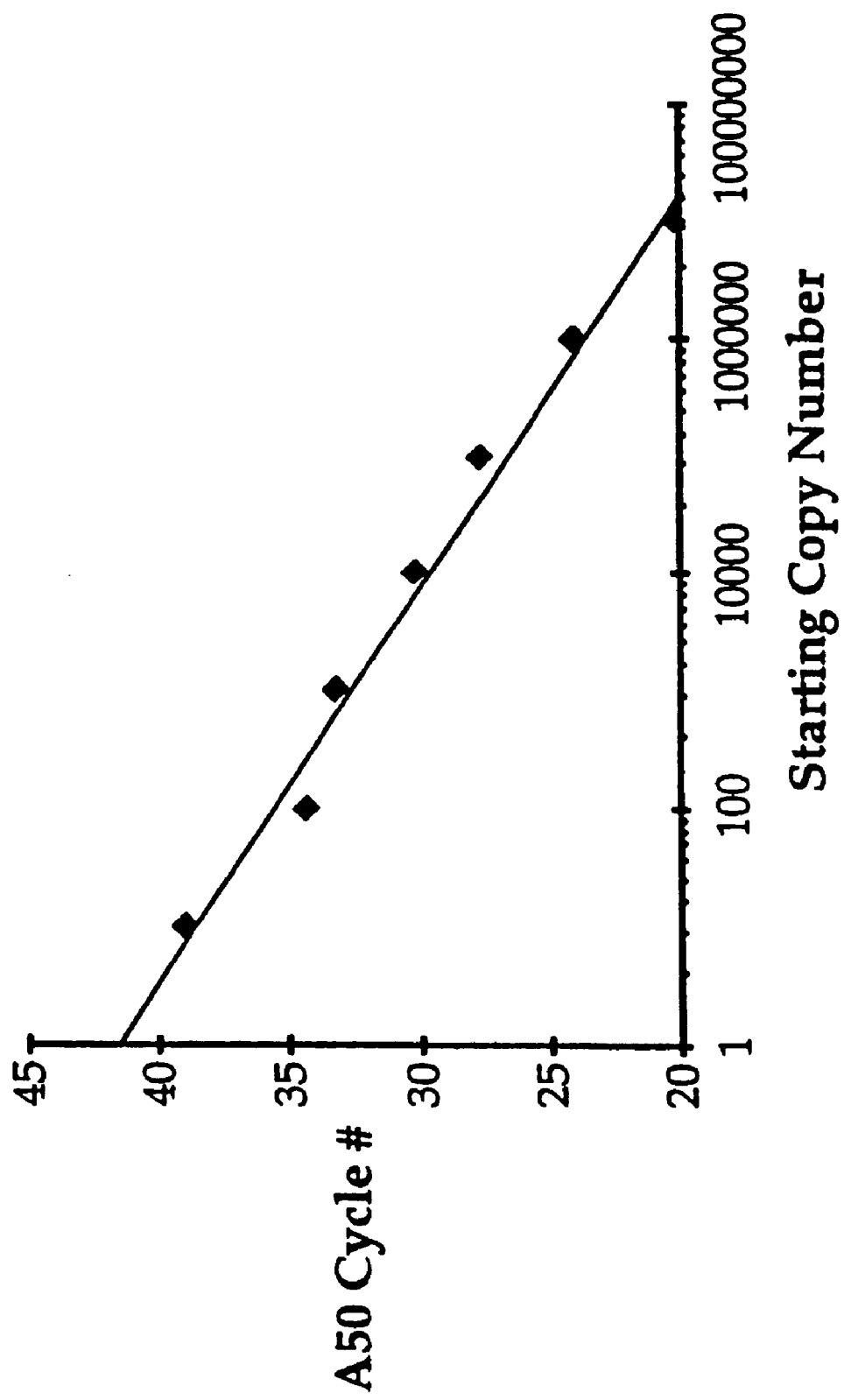
FIG. 24 shows a curve fit to the standard data of FIG. 23.
Figure 25:
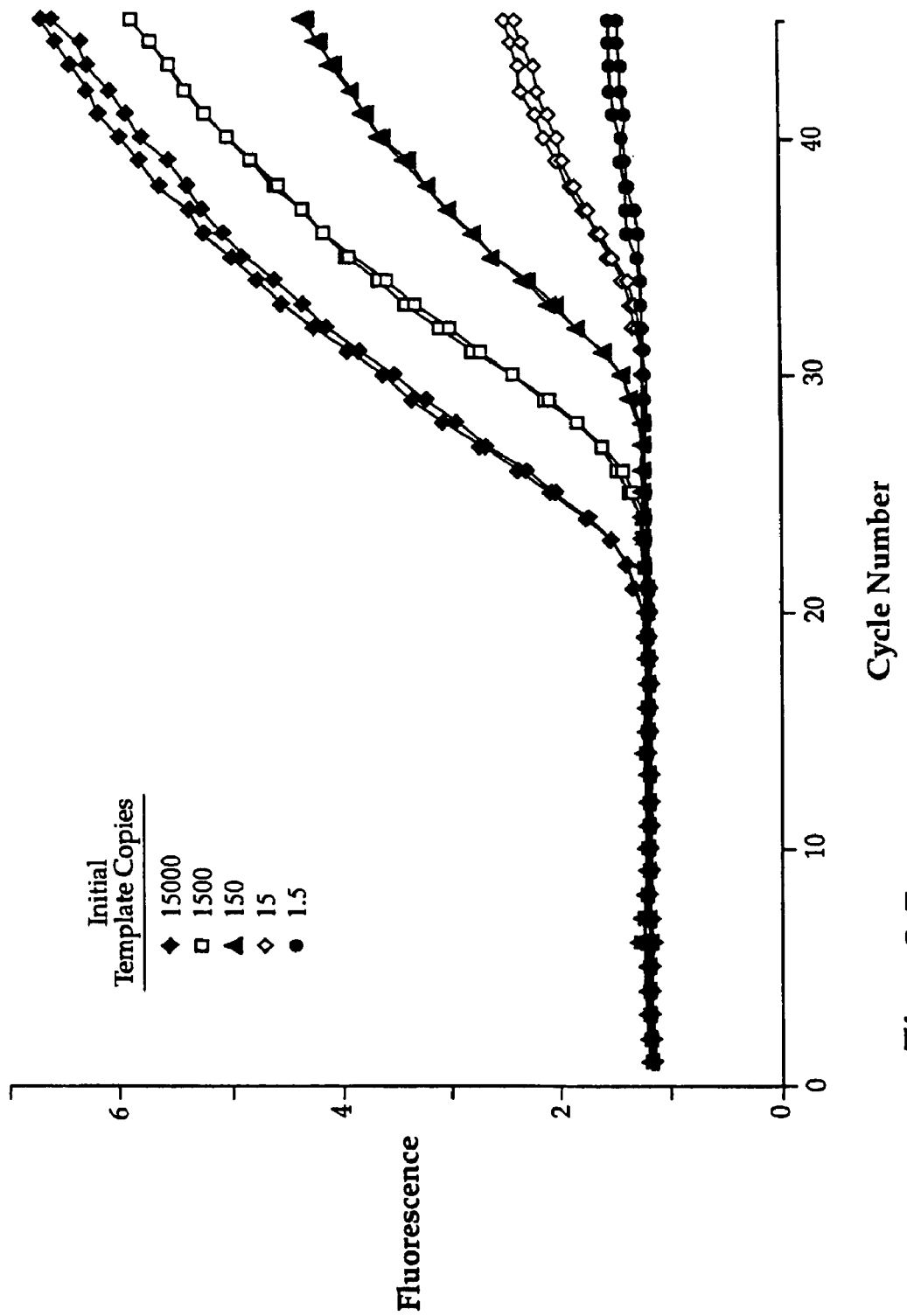
FIG. 25 shows a typical fluorescence vs cycle number plot of five standards monitored each cycle with a hydrolysis probe, wherein initial copy numbers are represented as follows: 1.5, (●); 15, (◇); 150, (▲); 1500, (□); 15,000, (◆).
Figure 26:
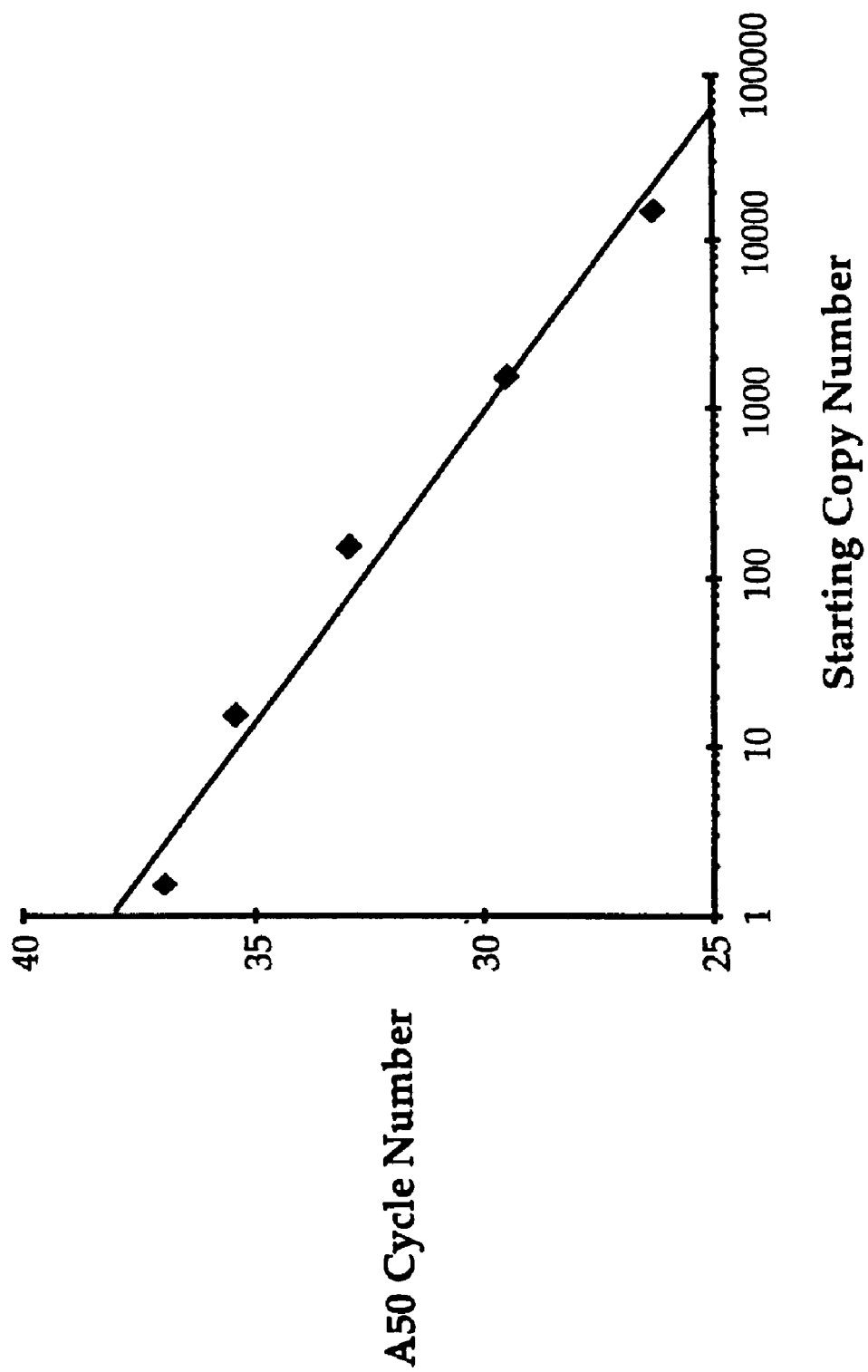
FIG. 26 shows a curve fit to the standard data of FIG. 25.

This equation gives good fits to this amplification data, and FIG. 24 shows that the value of the $A_{50}$ correlates well with the log of the starting copy number across seven orders of magnitude. FIG. 25 shows the same equation fit to data from amplifications that used a hydrolysis probe to detect DNA template over a 5 order of magnitude range. This equation gives good fits to this amplification data, and FIG. 26 shows that the value of the $A_{50}$ correlates well with the log of the starting copy number. This demonstrates the flexibility of the full curve fit approach as the equation has given good fits to both the sharp plateaus of the hybridization probe amplification curves and the steadily increasing "plateaus" of the hydrolysis probe curves.

Figure 27:
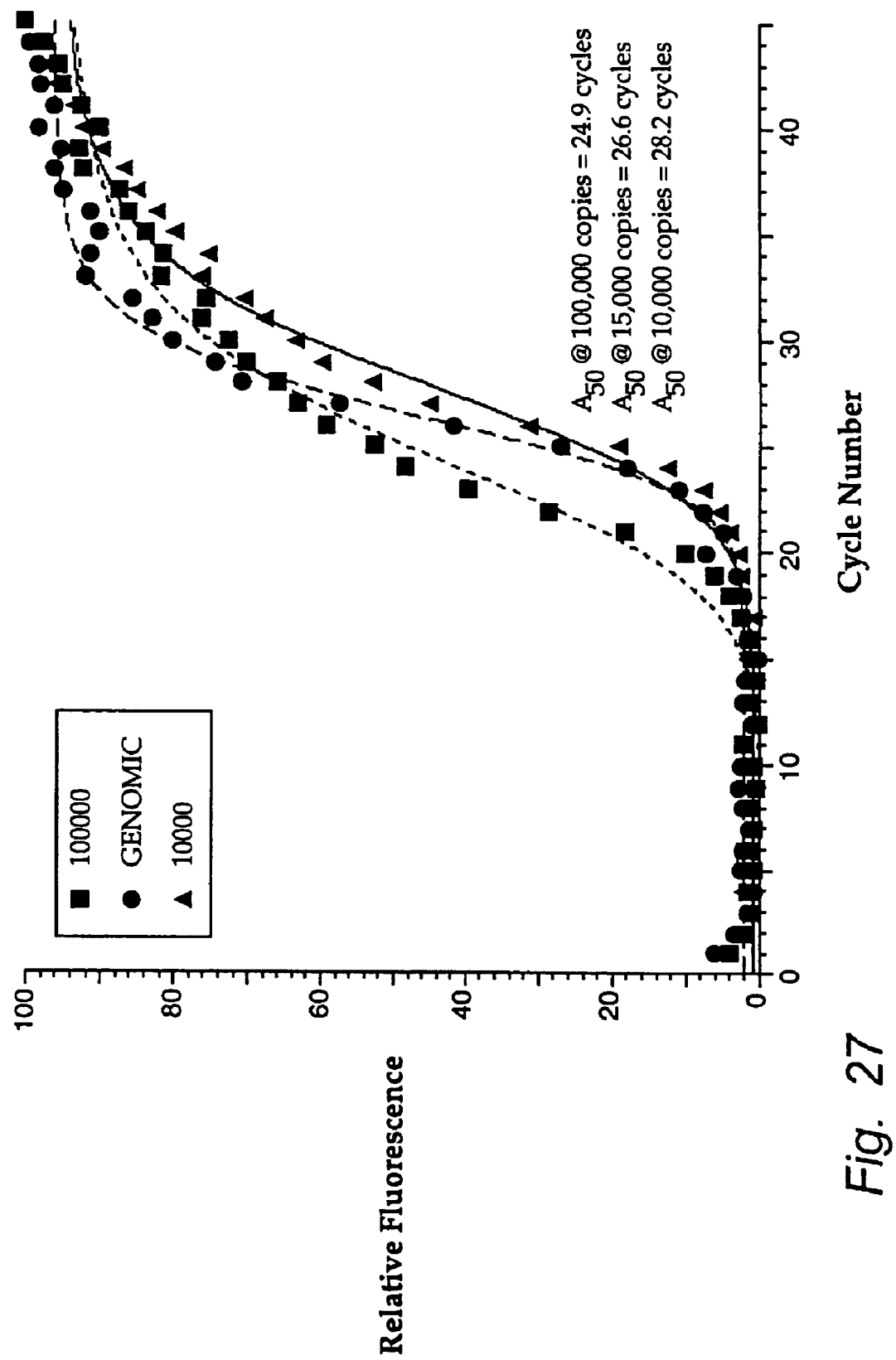
FIG. 27 shows a typical log fluorescence vs cycle number plot of three standard amplifications monitored with SYBR Green I, wherein: (■); (●); (▲).
Figure 28:
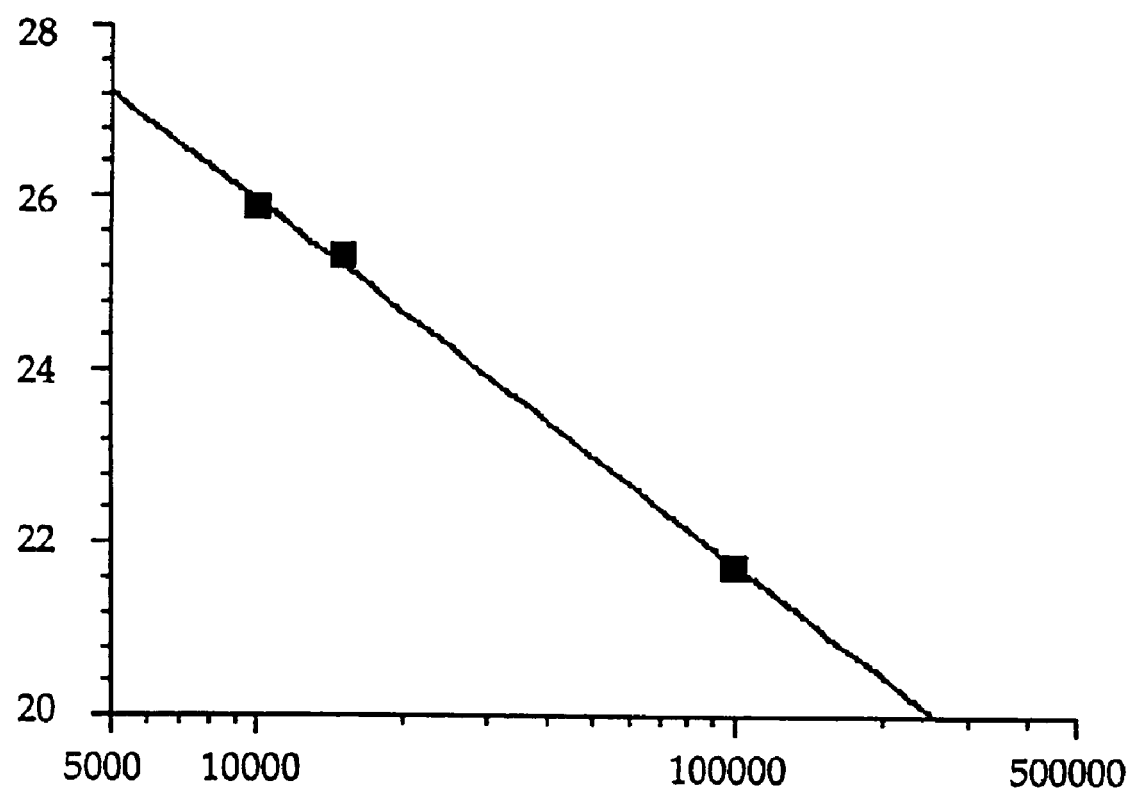
FIG. 28 shows different curve fit to the standard data of FIG. 27.

Total curve fits are not limited to this equation. FIG. 27 shows an amplification of three concentrations of DNA template fit to the equation: $y=(((as*x+ab)-(dmax*x/dd+x))/(1+(x/c)\hat{}b))+(dmax*x/dd+x)$, which is similar to the first 6 parameter equations except that the plateau is defined by a hyperbolic curve rather than by a line. FIG. 28 shows that the $A_{50}$ for this equation correlates well to the starting copy number.

While the $A_{50}$ has been used in these examples and level between the background and the plateau could be chosen if a particular technique is more robust lower or higher in the amplification profile. For example a series of amplification standard curves are evaluated for the best correlation between the starting copy number and the $A_{50}$, the $A_{40}$, the $A_{30}$, the $A_{20}$, and the $A_{10}$. The level of amplification that best correlates with the known starting copy number is determined. This will be different for different detections systems. FIG. 19 shows that coefficient of variation for various detection systems. The level of amplification that is the best predictor is likely to be the level with the lowest coefficient of variation.

As the DNA amplification reaction itself is better understood, other equations that have parameters that reflect physical processes could be used. The plateau of the DNA amplification curve has different causes in different reactions. It is often due to the inability of the primers to compete with product reannealing in the latter cycles. This effect could be captured with a parameter that is dependent on the square of the concentration of product in the reaction (as reannealing rate is proportional to the square of the product concentration). Another cause of the plateau can be the depletion of the primers. Primer limited reactions have a characteristic shape, they have a very sharp plateau that can be recognized. Primer limited reaction fits will include parameters that define this sharp top. Enzyme limited reactions have a very rounded plateau that can be fit accordingly. Weighting factors can be devised that reflect the known coefficients of variation for the given system to more heavily weight the more reliable data points. By fitting more of the points in an amplification profile, more accurate and robust estimates of starting copy number can be obtained. One or more of the parameters of these fits can be used to estimate the starting copy number of unknown samples.

Figure 29:
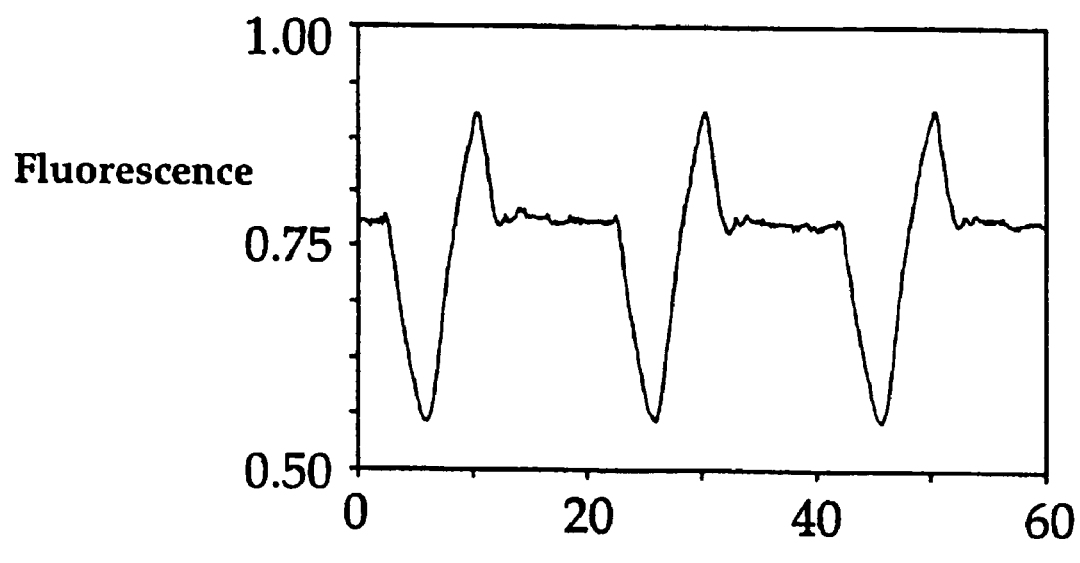
FIGS. 29A&B show plots of (A) time v. fluorescence and (B) time v. temperature demonstrating the inverse relationship between temperature and fluorescence.
Figure 29:
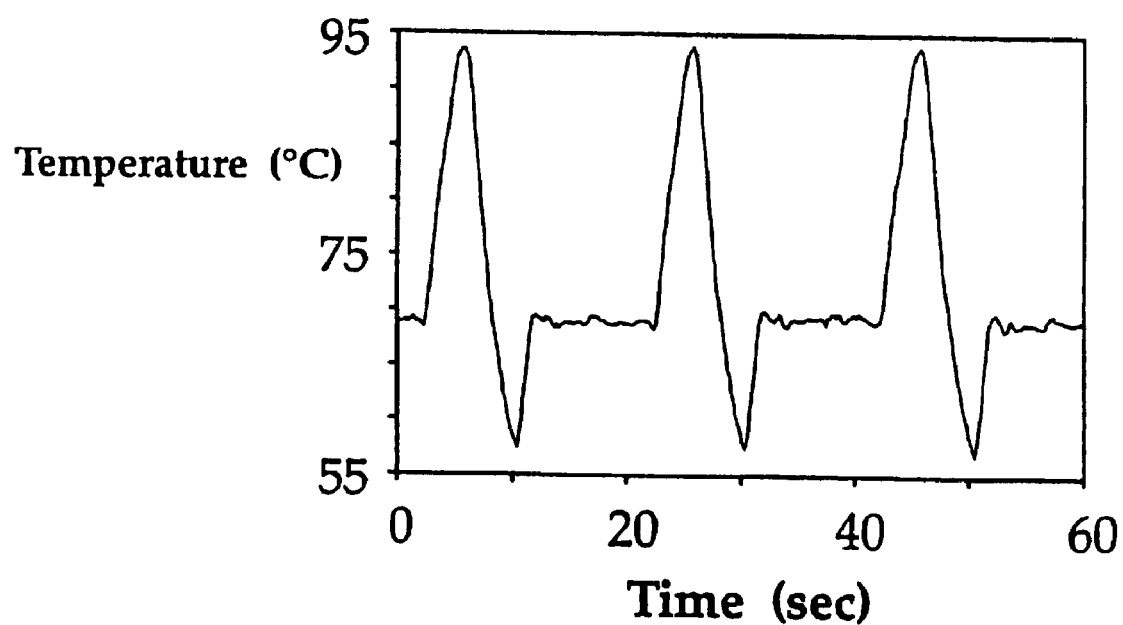

Continuous fluorescence monitoring of PCR. The present invention's feature of continuous monitoring, that is, monitoring many times within each PCR cycle, will now be discussed. While fluorescence monitoring during PCR can be done once each cycle at a constant temperature, the present invention provides the important advantage of providing continuous monitoring throughout the PCR cycle. Temperature is important because fluorescence changes as the temperature changes. FIGS. 29A&B demonstrate the inverse relationship between temperature and fluorescence for SYB™ Green I. This is a confounding effect during temperature cycling that is usually eliminated by considering fluorescence once per cycle at a constant extension temperature. However, in accordance with the present invention, monitoring fluorescence during temperature changes is very informative. Prior to the present invention, continuous fluorescence monitoring within each cycle, as opposed to once each cycle, has not been carried out. In accordance with the present invention, time, temperature and fluorescence is acquired every sec, every 200 msec, every 100 msec or even at a greater frequency. Such data can reveal fine details of product denaturation, reannealing and extension, and probe annealing and melting during rapid cycling not available in previously available methods.

EXAMPLE 10

Figure 30:
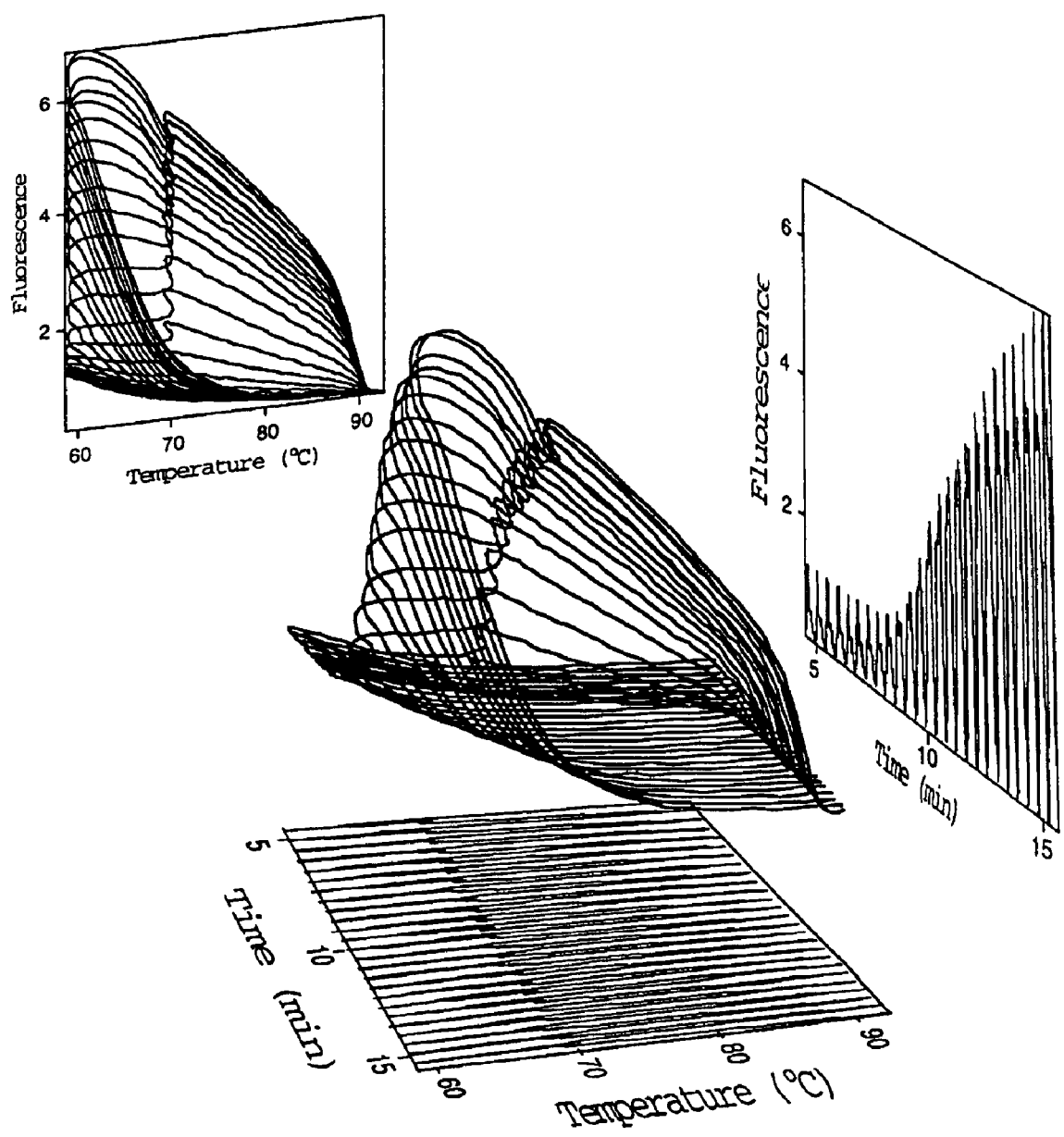
FIG. 30 is a chart showing 2D plots of temperature v. time, fluorescence v. time, and fluorescence v. temperature, also shown as a 3D plot, for the amplification of a 180 base pair fragment of the hepatitis B genome in the presence of SYBR Green I.

A 180-base-pair fragment of the hepatitis B surface antigen gene was amplified from $10^6$ copies of purified PCR product using primers 5'-CGTGGTGGACTTCTCTCAAT-3' (SEQ ID NO:1), and 5'-AGAAGATGAGGCATAGCAGC-3' (SEQ ID NO:2)(Genbank sequence HVHEPB). The amplification conditions of Example 2 were followed except that the reaction contained a 1:20,000 dilution of SYBR™ Green I and 2 mM $MgCl_2$. Each temperature cycle was 27 sec long (92° C. maximum, 59° C. minimum, 5 sec at 70° C., average rate between temperatures 3.0° C./sec). Time, temperature, and 2 channels of fluorescence were acquired every 200 msec and continuously displayed as fluorescence v. cycle number and fluorescence v. temperature plots. FIG. 30 shows a 3D trace of temperature, time and fluorescence for cycles 10 through 34. This 3D curve is also projected in FIG. 30 as 2D plots of temperature v. time, fluorescence v. time, and fluorescence v. temperature. The temperature v. time projection of FIG. 30 repeats each cycle and provides essentially the same information as set forth in FIG. 3. Because fluorescence varies inversely with temperature, the fluorescence v. time projection shown in FIG. 30 at early cycles is a scaled mirror image of the temperature v. time plot (see FIG. 29). As product accumulates, the fluorescence increases at all temperatures with double stranded product. However at denaturation temperatures, fluorescence returns to baseline since only single stranded DNA is present. The fluorescence v. temperature projection of double stranded dyes shown in FIG. 30 eliminates the time axis and shows the temperature dependence of strand status during DNA amplification.

EXAMPLE 11

Figure 31:
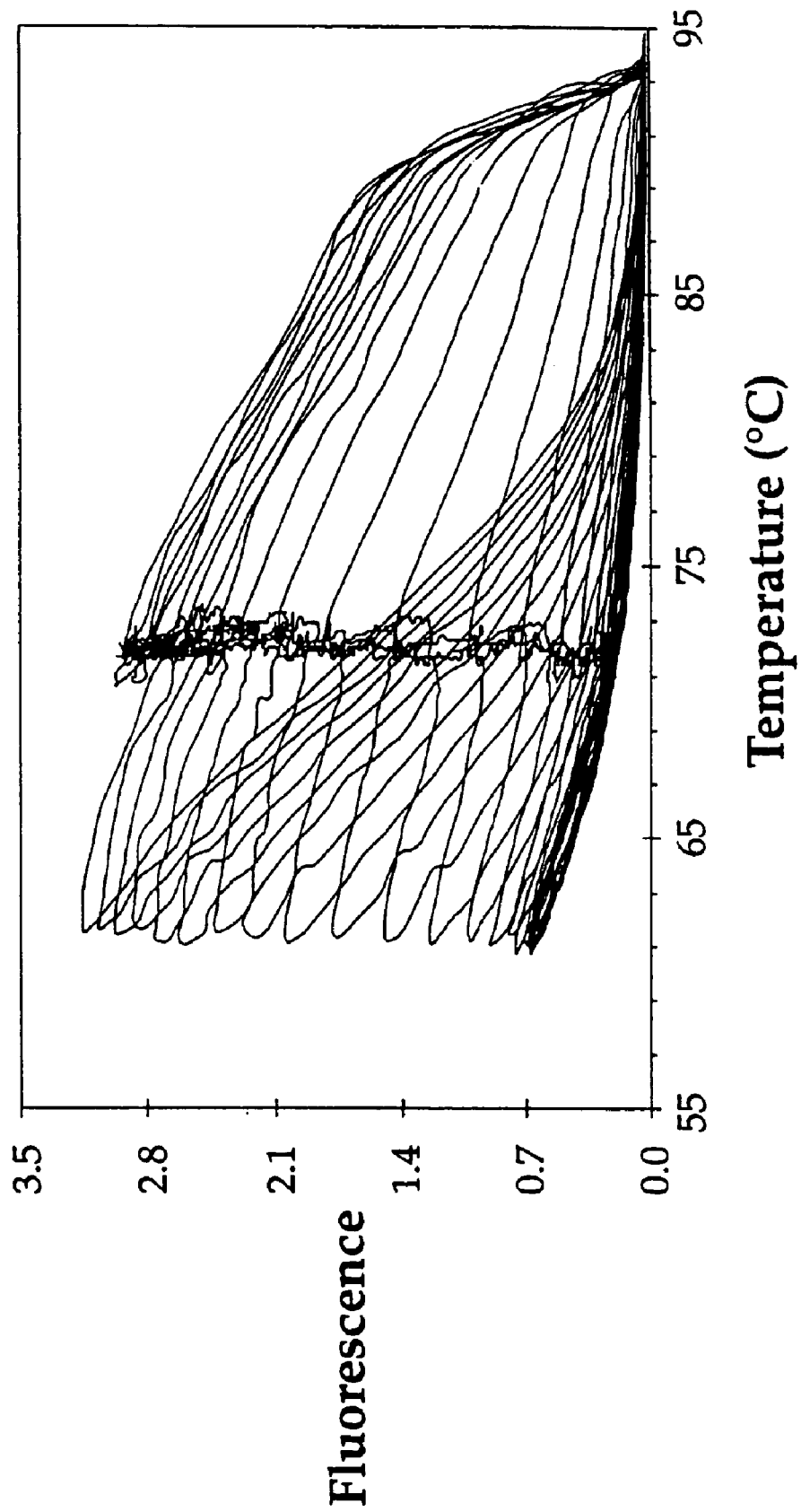
FIG. 31 is a fluorescence v. temperature projection for the amplification of a 536 base pair fragment of the human beta-globin gene in the presence of SYBR Green I.

A 536 base pair fragment of the human beta-globin gene was amplified from 25 ng of genomic DNA and a 1:10,000 dilution of SYBR™ Green I in a volume of 5 µl. Each temperature cycle was 28 sec long (95° C. maximum, 61° C. minimum, 15 sec at 72° C. with an average rate between temperatures of 5.2° C./sec). Other conditions are the same as those described in FIG. 30. Cycles 15-40 are displayed. The temperature dependence of product strand status during PCR is revealed by fluorescence v. temperature plots using as shown in FIG. 31. Early cycles represented appear identical, with a nonlinear increase in fluorescence at lower temperatures. As amplification proceeds, temperature cycles appear as rising loops between annealing and denaturation temperatures. As the sample is heated, fluorescence is high until denaturation occurs. As the sample cools, fluorescence increases, reflecting product reannealing. When the temperature is constant during extension, increasing fluorescence correlates with additional DNA synthesis.

As will be appreciated by an understanding of this disclosure, continuous monitoring within a cycle can provide insight into DNA amplification mechanics not previously available in the art. Using the present invention, many aspects of DNA amplification that have heretofore been little understood are discernable. For example, rapid cycle amplification claims to denature the product in less than one second, while the prior art uses ten seconds to one minute of denaturation. Observing product melting by real time fluorescence monitoring with double strand dyes in accordance with the present invention (FIGS. 30 and 31) shows that use of the shorter denaturation times is effective. As another example, many causes of the known "plateau effect" have been proposed, but few data are available to distinguish between alternatives. As shown in FIG. 31, product reannealing is very rapid. In fact, during later cycles of amplification, a majority of product is reannealed each cycle during cooling before the primer annealing temperature is reached. This occurs with cooling rates of 5-10° C./sec in rapid cycle instrumentation. The product reannealing with slower, prior art temperature cyclers will be more extensive and this undesirable effect will be greater. Product reannealing appears to be a major, and perhaps the sole, cause of the "plateau effect."

Now consider continuous monitoring of sequence specific probes. As will be appreciated by an understanding of this disclosure, continuous monitoring within a cycle can identify the nature of probe fluorescence.

EXAMPLE 12

Figure 32:
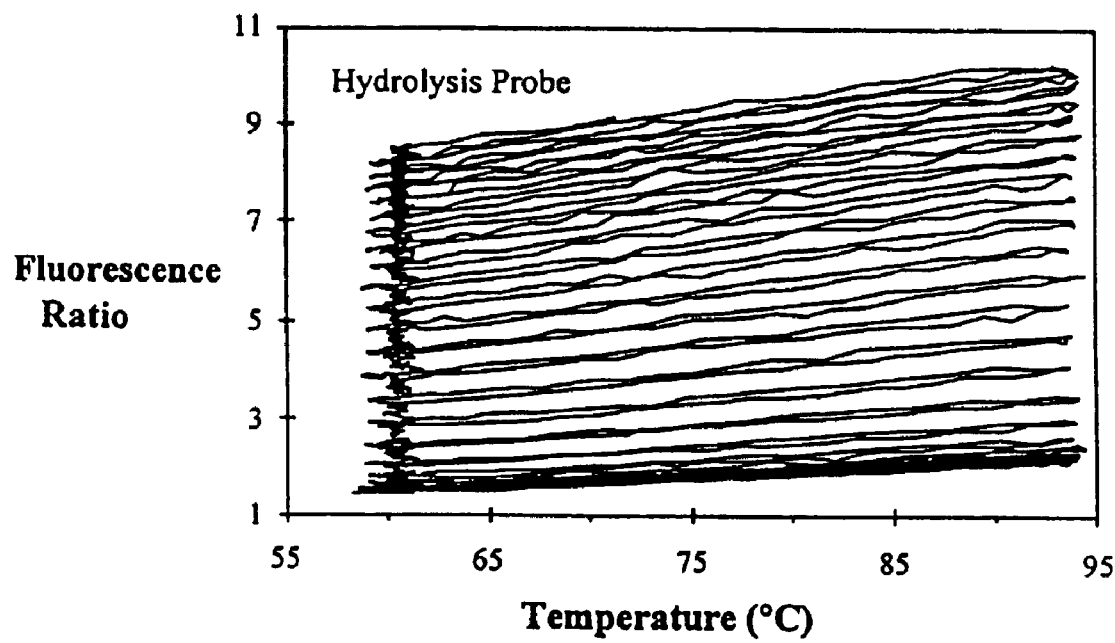
FIGS. 32A&B provide a plot showing (A) a linear change in fluorescence ratio with temperature for hydrolysis probes, and (B) a radical change with temperature for hybridization probes.
Figure 32:
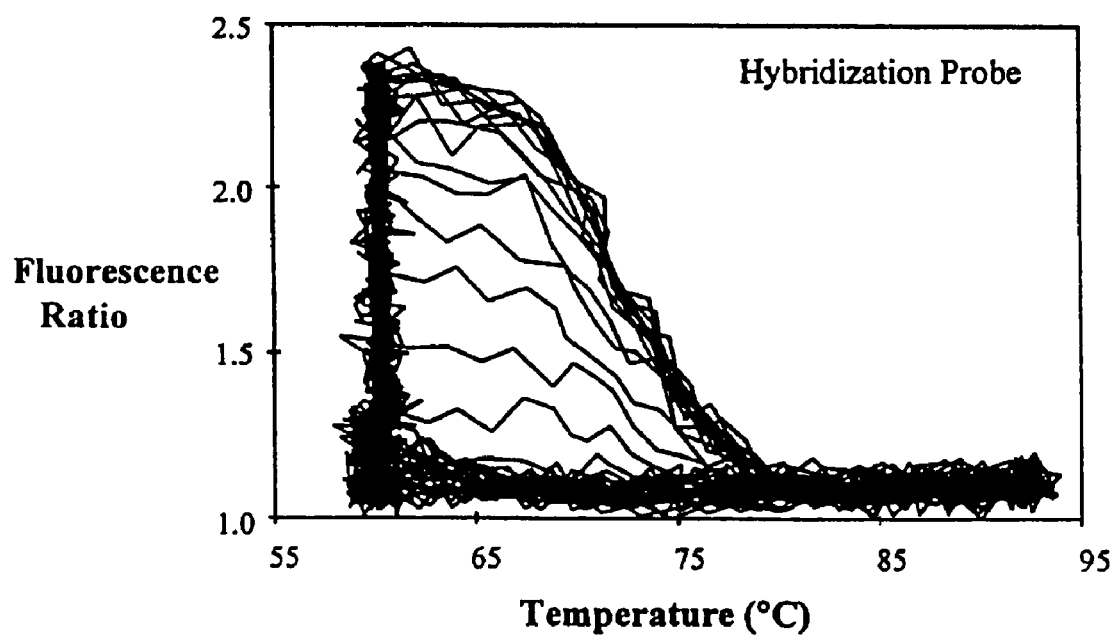

Continuous monitoring of amplification every 200 msec was performed with a dual-labeled hydrolysis probe (beta-actin) and adjacent hybridization probes (beta-globin) as in Example 7. In FIG. 32A, cycles 20-45 of a reaction monitored with the hydrolysis probe is shown. Hydrolysis probes show a linear change in fluorescence ratio with temperature and a parallel increase in fluorescence as more probe is hydrolyzed. In contrast, the fluorescence ratio from hybridization probes varies radically with temperature (FIG. 32B, cycles 20-40). During the annealing/extension phase, the probes hybridize to single stranded product and the fluorescence ratio (Cy5/fluorescein) increases. During heating to product denaturation temperatures, the probes dissociate around 70° C., returning the fluorescence ratio to background levels.

EXAMPLE 13

Figure 33:
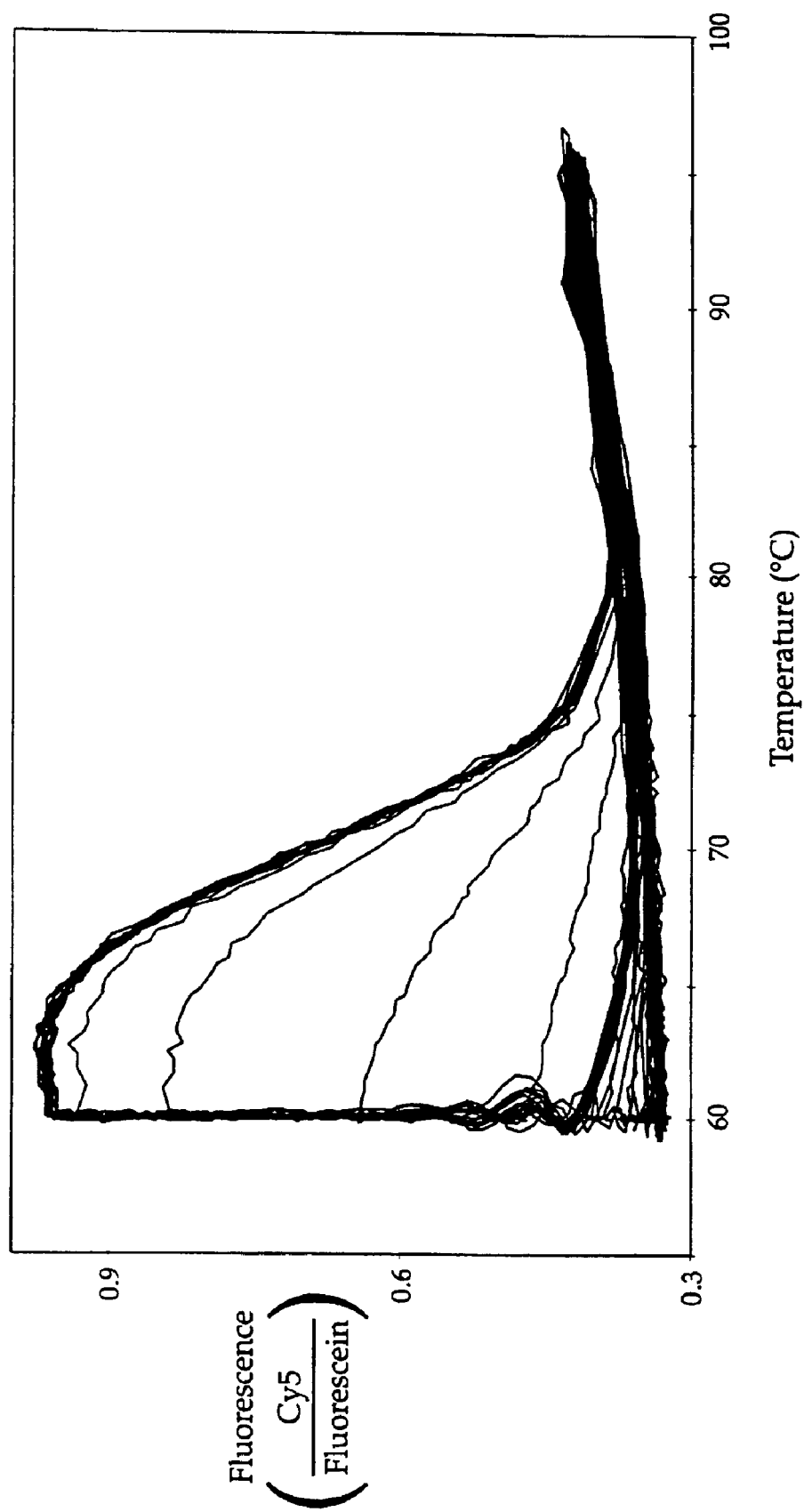
FIG. 33 shows a fluorescence ratio v. temperature plot of amplification with an exo⁻ polymerase in the presence of adjacent hybridization probes.
Figure 34:
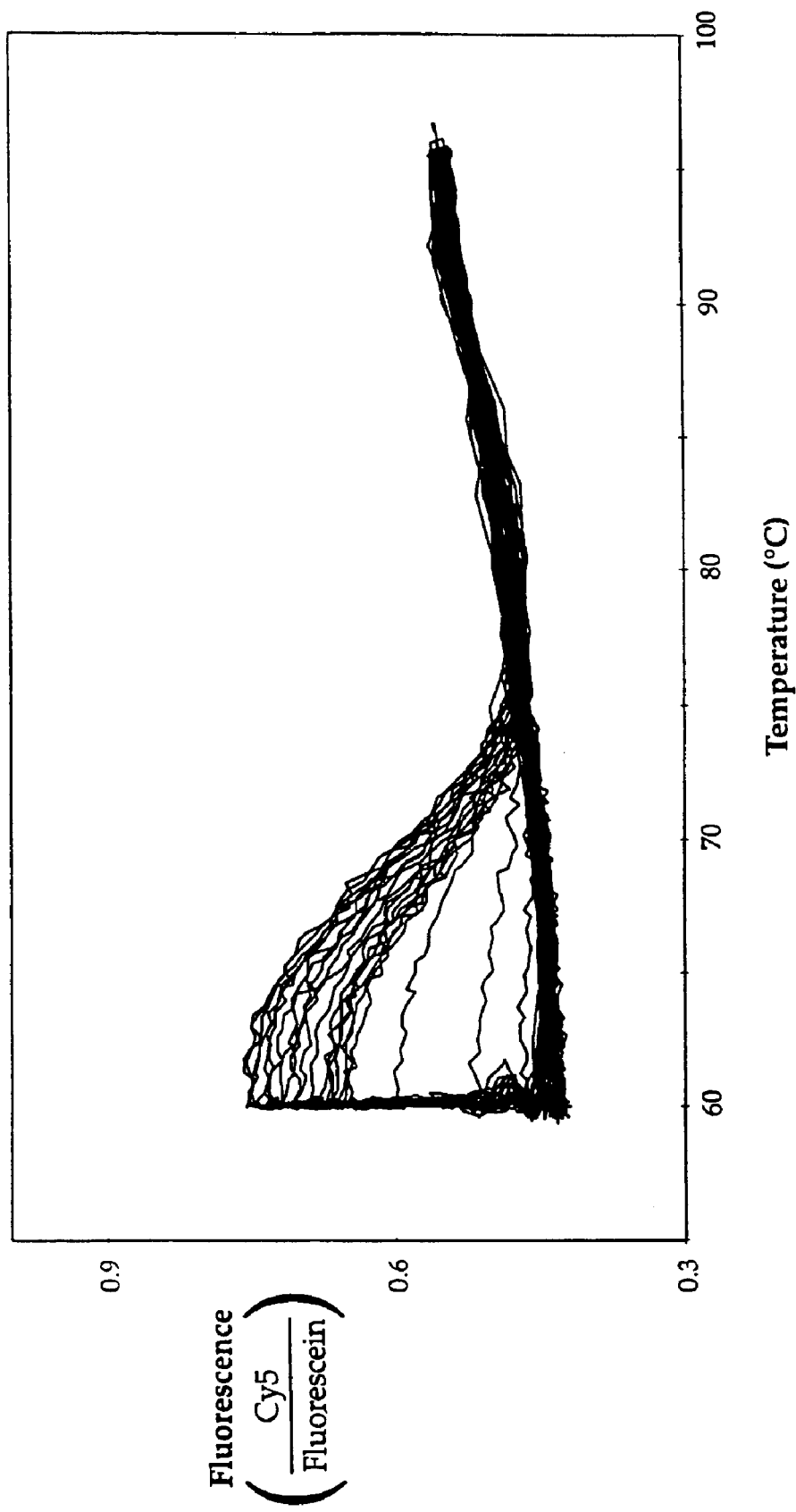
FIG. 34 shows a fluorescence ratio v. temperature plot of amplification with an exo⁺ polymerase in the presence of adjacent hybridization probes.
Figure 35:
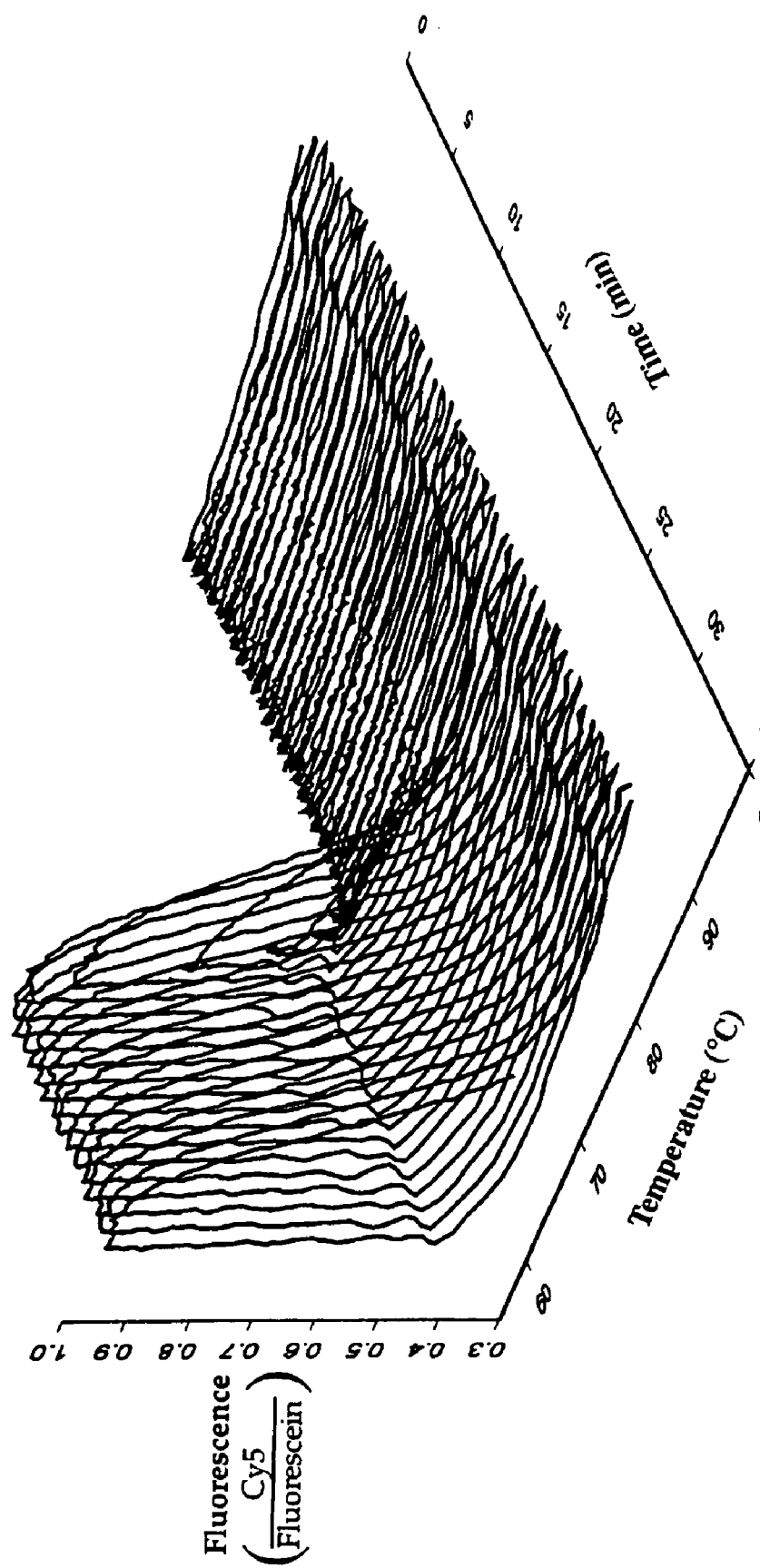
FIG. 35 shows a 3-dimensional plot of temperature, time and fluorescence during amplification with an exo⁻ polymerase in the presence of adjacent hybridization probes.
Figure 36:
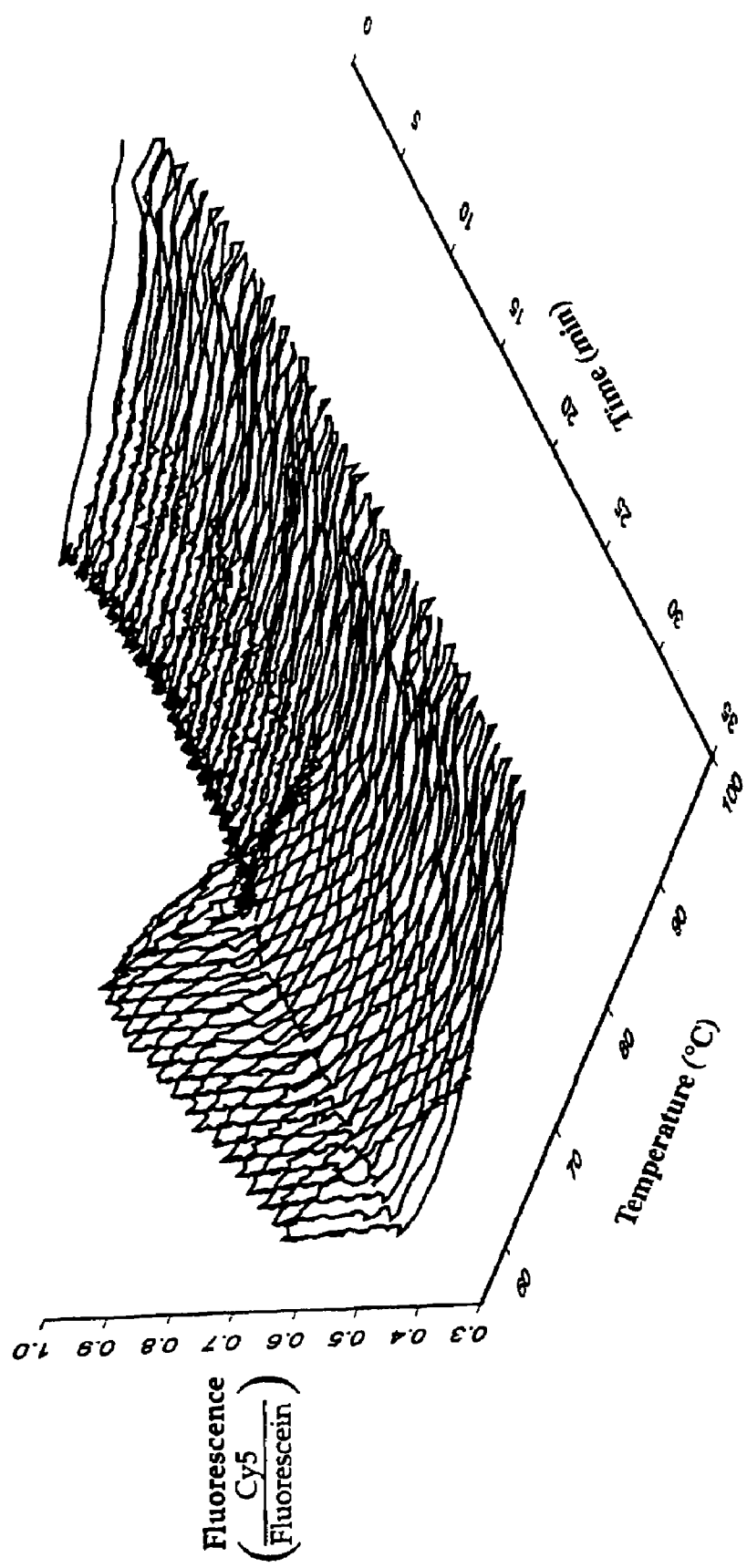
FIG. 36 shows a 3-dimensional plot of temperature, time, and fluorescence during amplification with an exo⁺ polyerase in the presence of adjacent hybridization probes.

A 110 base pair beta-globin fragment was amplified from 50 ng of genomic DNA in a volume of 10 µl. The amplification conditions and adjacent hybridization probes of Example 3 were followed with either 0.4 U of Taq polymerase or 0.8 U of KlenTaq1. Fluorescence was monitored each 100 msec. Fluorescence v. temperature plots using KlenTaq1 (FIG. 33) and Taq (FIG. 34) demonstrate melting of the probes at about 70° C. The maximal signal with KlenTaq1 is greater than that with Taq, because of the exonuclease activity of the latter. At later cycles with Taq, the fluorescence each cycle begins to decrease as the concentration of intact probe decreases. Three dimensional plot of temperature, time, and fluorescence are shown in FIG. 35 (KlenTaq1) and FIG. 36 (Taq).

The present invention's combination of (1) continuous fluorescence monitoring within each temperature cycle and (2) analysis of the temperature and time dependence of hybridization provides advantages not otherwise obtainable. FIG. 2 shows that information that was previously unobtainable can be extracted by continuous monitoring throughout the cycle. Continuous fluorescence monitoring during the product melting phase of the cycle provides useful information on the purity, identity, and quantity of DNA present during that cycle.

As a PCR reaction is heated from the extension temperature to the denaturation temperature, any DNA in the sample is melted to single strands. This denaturation can be observed as a drop in the fluorescence of SYBR™ Green I. For small PCR products, the melting transition occurs over a narrow temperature range and the midpoint of that melting range is referred to as the Tm. Similar to sizing by gel electrophoresis, melting peak analysis measures a fundamental characteristic of DNA and can be used to identify amplified products. Unlike gel electrophoresis, melting curve analysis can distinguish products of the same length but different GC/AT ratio. In addition, two products with the same length and GC content, but differing in their GC distribution (for example, equally distributed vs. a GC clamp on one end) would have very different melting curves. The temperature at which PCR products melt varies over a large range. Using empirical formulas known in the art, the effect of GC content on the melting temperature (Tm) of DNA predicts that a 0% GC duplex would melt 41° C. lower than a 100% GC duplex. Given the same GC content, a 40 base pair primer dimer would melt 12° C. below a 1000 bp product. Hence, the range of Tm for potential PCR products spans at least 50° C. This wide range allows most PCR products to be differentiated by melting curves. Thus, the combination of fluorescence monitoring of PCR with melting curve analysis provides simultaneous amplification, detection, and differentiation of PCR products.

EXAMPLE 14

DNA melting curves for three different PCR products were acquired on a microvolume fluorimeter integrated with a 24-sample thermal cycler with optics for SYBR™ Green I fluorescence (LightCycler LC24, Idaho Technology, Idaho Falls, Id.). The primers for the 180 base pair hepatitis B surface antigen gene amplification were 5'-CGTGGTG-GACTTCTCTCAAT-3' (SEQ ID NO:1) and 5'-AGAAGAT-GAGGCATAGCAGC-3'(SEQ ID NO:2). The primers for the 292 base pair prostate specific antigen (PSA) gene amplification were 5'-CTGTCCGTGACGTGGATT-3' (SEQ ID NO:7) and 5'-AAGTCCTCCGAGTATAGC-3'(SEQ ID NO:8). The 536 base pair human beta-globin gene amplification was done as in Example 7. PCR was performed as described in Example 2. Amplification products were purified by phenol/chloroform extraction and ethanol precipitation, followed by repeated washing through a Centricon 30 microconcentrator (available from Amicon of Danvers, Mass.). Template concentrations were determined by absorbency at 260 nm and had A(260)/A(280) ratios greater than 1.7.

Figure 37:
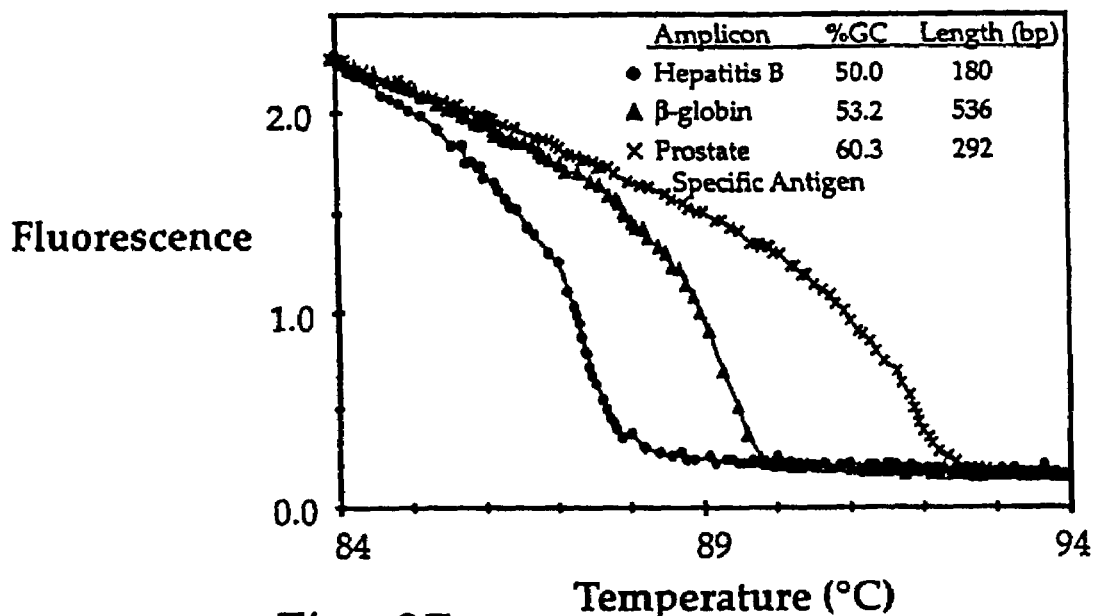
FIG. 37 shows melting curves for PCR-amplified products of hepatitis B virus (●; 50% GC, 180 bp); beta-globin (▲; 53.2% GC, 536 bp); and prostate specific antigen (X; 60.3% GC, 292 bp).

Fifty ng of purified DNA in 50 mM Tris, pH 8.5, 2 mM $MgCl_2$, and 250 µg/ml bovine serum albumin and a 5 µl volume were pipetted into the open plastic reservoir of composite glass/plastic reaction tubes, centrifuged at low speed to place the sample at the tip of the glass capillary, and sealed inside with a plastic plug. Fluorescence data for melting curves was acquired by integrating the signal over 0.25-2.0 seconds during a linear temperature transition to 95° C. at 0.1-10.0° C./second. The fluorescence was continuously acquired and displayed at fluorescence v. temperature plots in the LabView programming environment (National Instrument, Austin, Tex.). FIG. 37 shows the melting curves of the three purified PCR products.

Figure 38:
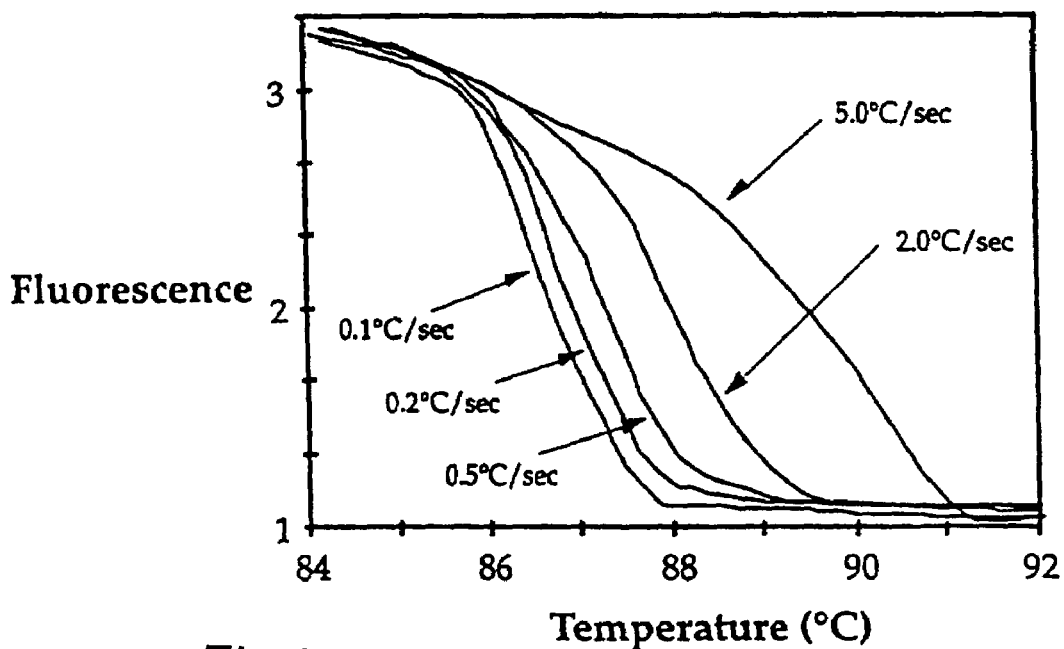
FIG. 38 shows melting curves for PCR-amplified product of hepatitis B virus at heating rates of 0.1° C. to 5.0° C.

The Tm's of three products in FIG. 37 span only 6 degrees and two of the curves are separated by only 2 degrees. This small separation is ample to allow easy differentiation of the products. The importance of GC percentage over length on Tm is illustrated by the 292 bp PSA product melting at a higher temperature than the longer 536 bp beta-globin fragment. Melting curves are often obtained at rates of 0.5° C./minute to ensure equilibrium. Moreover, as the heating rate decreases, the melting curve shifts to lower temperatures and becomes sharper (FIG. 38, hepatitis B fragment). Note however, that the melting curves of FIG. 37 were obtained during a heating rate of 0.2° C./sec (12° C./minute) and can differentiate products differing in Tm by 2° C. or less.

Figure 39:
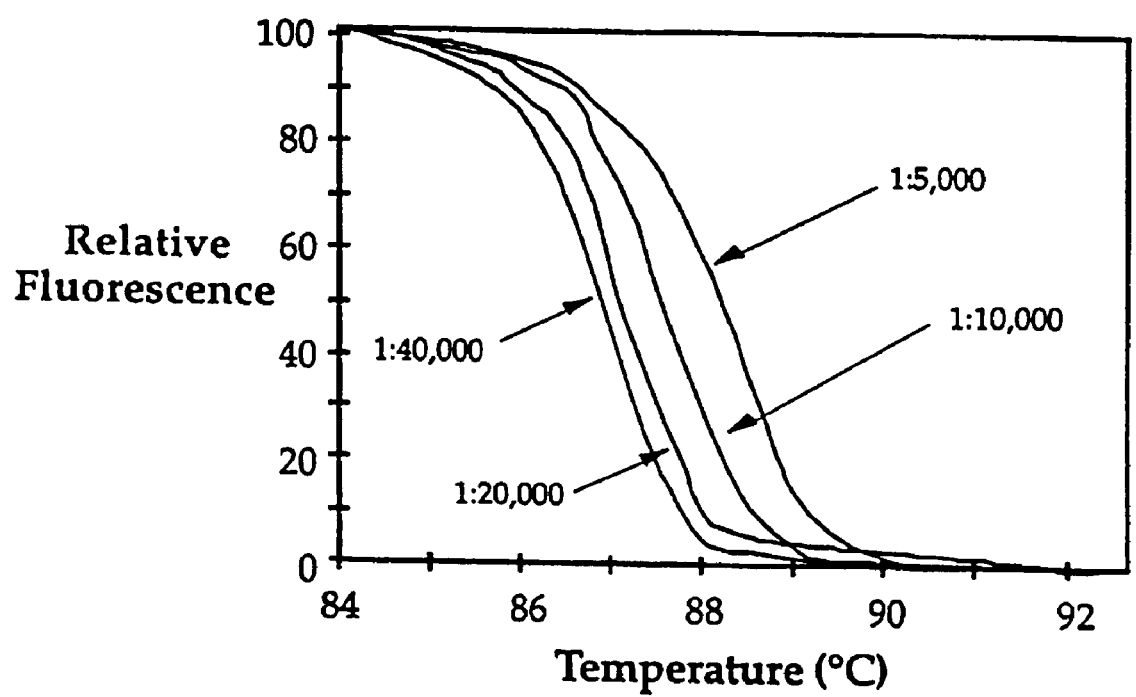
FIG. 39 shows melting curves for PCR-amplified product of hepatitis B virus at various SYBR™ Green I concentrations.

The apparent Tm of PCR products is also dependent on double-strand-specific DNA dye concentration (FIG. 39, hepatitis B fragment). Higher concentrations of dye increase the stability of the DNA duplex and the observed Tm.

For monitoring of melting curves with SYBR™ Green I, the preferred conditions are 1:7,000-1:30,000 fold dilution of SYBR Green I with heating rates of 0.1-0.5° C./second. These conditions allow easy differentiation of products that differ in Tm by 2° C.

More precise temperature control and software for melting peak analysis will reduce the detectable difference in Tm to a fraction of a degree. This will allow the differentiation of most PCR products. Not all products can be differentiated by Tm however, just as it is possible to misread electrophoresis results because of comigration of two or more products, it is possible that some of the product melting in the expected range may not be the intended product. However, if no DNA melts in the range of the expected product, it can conclusively be said that none of the expected product is present.

Another form of product differentiation available with melting curve analysis is the distinctive patterns of domain melting seen in longer PCR products. While short products (<300 bp) usually melt in one transition, longer products can have internal melting domains that give melting curves of a complex, distinctive shape. These complex melting curves can be used as a fingerprint for product identification.

Melting curve analysis can be used to differentiate intended product from nonspecific products such as primer dimers. Primer dimers melt over a wide range of low temperatures; very different from the sharp melting curves of specific PCR amplification products. Larger heterogeneous products which resulted from running many cycles at low annealing stringency have lower and broader melting curves when compared with pure PCR product.

EXAMPLE 15

Amplification of the 536 beta-globin gene fragment was performed as in Example 7 with a 1:30,000 dilution of SYBR™ Green I except that the conditions were varied. In reaction A (FIG. 40), no template was added and the reaction was cycled at 94° C. for 0 sec, 60° C. for 0 sec, and 72° C. for 10 sec for 30 cycles to produce small nonspecific amplification products. In B, amplification of $10^6$ initial copies of purified template at low stringency (94° C. for 0 sec, 50° C. for 0 sec, and 72° C. for 10 sec) for 55 cycles showed a broad size range of amplification products on gel electrophoresis and melts across a wide temperature range. In C, $10^6$ initial copies of purified template were cycled at 94° C. for 0 sec, 60° C. for 0 sec, and 72° C. for 10 sec for 30 times and shows a single bright band and melts in a sharp transition. The temperature transition rate was 0.2° C./sec. A Hind III digest of λ phage DNA (M) is used as a marker.

Figure 40A:
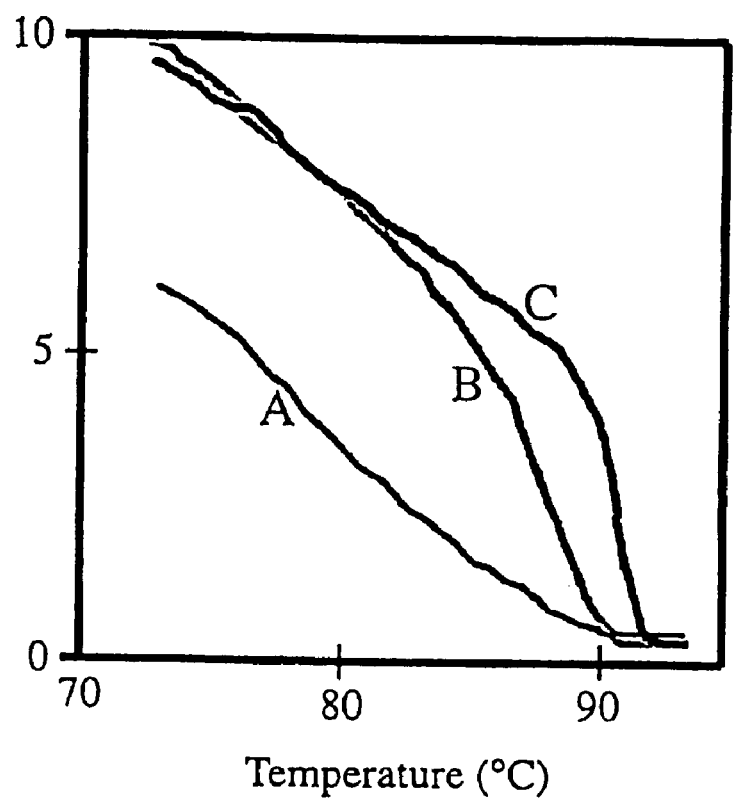
FIGS. 40A&B show (A) melting curves and (B) electrophoretically fractionated bands of products of a beta-globin fragment amplified with (a) no added template, (b) $10^6$ copies of added template under low stringency conditions, and (c) $10^6$ copies of added template under higher stringency conditions.
Figure 40B:
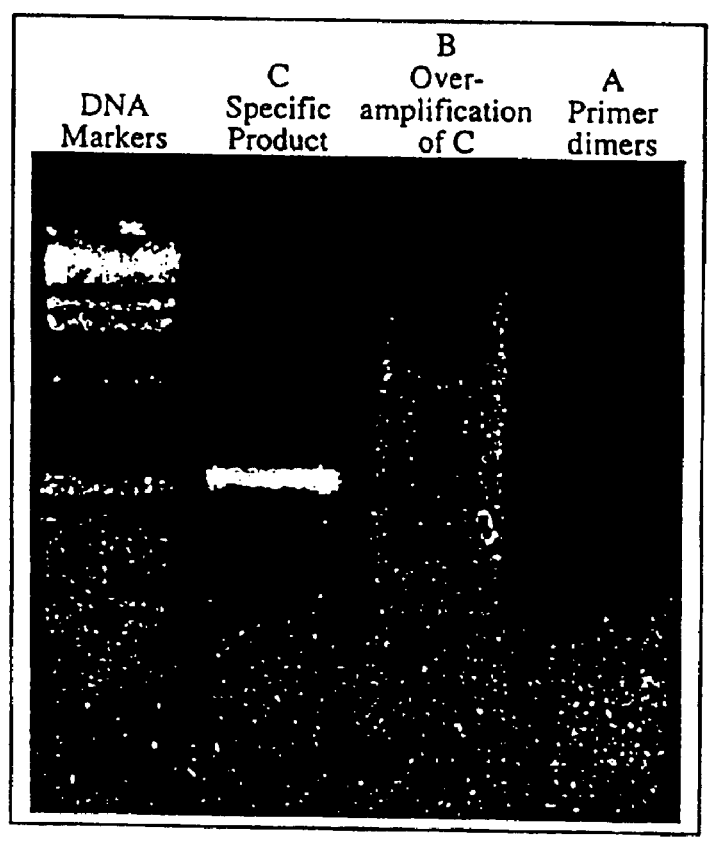

FIG. 40 shows how melting curves accurately reflect the specificity of a PCR reaction. The sharp, high temperature melting curve C corresponds to a single band on a gel. The low temperature, broad melting, curve A comes from analysis of a no template control that shows only primer dimers. Overamplification of the product in C gives the intermediate melting curve B, still clearly differentiable from the specific product.

The melting curves seen, for example, in FIG. 37, can be better quantified by first taking the derivative of fluorescence (F) with respect to temperature (T). This derivative is plotted as $-dF/dT$ v. T and converts the melting curves to melting peaks.

EXAMPLE 16

Figure 41A:
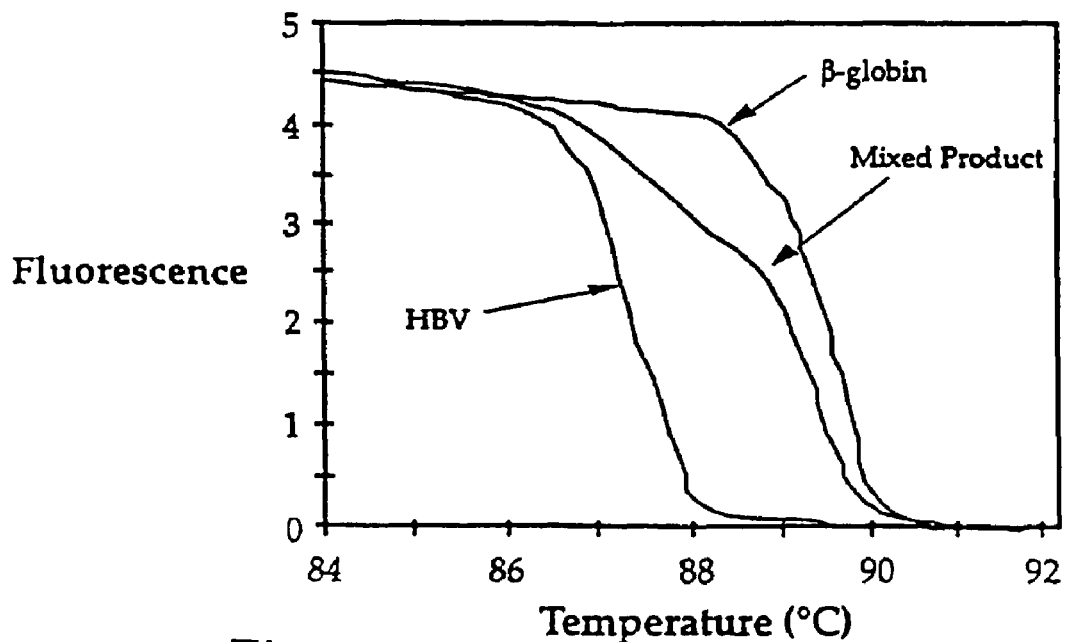
FIGS. 41A&B show (A) melting curves and (B) melting peaks of hepatitis B virus fragment (HBV), β-globin, and a mixture thereof.
Figure 41B:
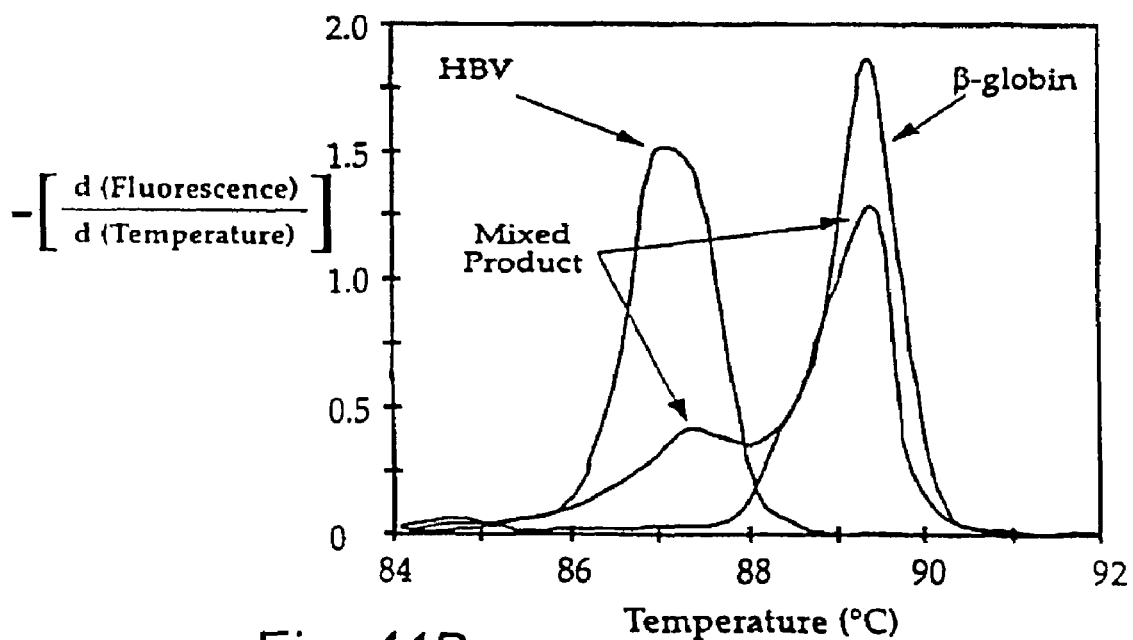

The purified hepatitis B and beta-globin gene fragments of Example 14 were melted individually and together with a temperature transition rate of 0.2° C./sec and other conditions as specified in Example 14 (FIG. 41). The somewhat subjective determination of Tm from the melting curves (top) is easily called by eye from the melting peaks (bottom). The area under the melting peaks can also be quantified by integration of the area under the curves. The fluorescence baseline was first subtracted from the $-dF/dT$ v. T plot assuming that the magnitude of the baseline varies as the area under the curve. Then the peaks were fit by nonlinear least squares regression to gaussians with the mean, standard deviation, and height of the peak as the fit parameters. The area under each gaussian was taken as the peak area. All calculations were performed in the LabView programming environment (National Instruments, Austin, Tex.). FIG. 41 shows an example of this conversion of melting curves to melting peaks. The code for these calculations is included as appendix A.

The ability to distinguish specific product from primer dimer and other reaction artifacts improves the use of double-strand-specific DNA dyes in the quantification of low initial copy numbers. Relatively large initial template copy numbers have been quantified using ethidium bromide (Higuchi & Watson, supra). However, at low initial copy numbers, the background amplification of primer dimers and other amplification artifacts interferes with the specific amplification signal. With the present invention's ability to differentiate specific products from non-specific artifacts, double-strand-specific DNA dyes can be used to quantify low initial template copy numbers. This is advantageous because of the simplicity of using these dyes. The double-strand-specific DNA dyes can be used in any amplification and custom fluorescently-labeled oligonucleotides are not necessary. Quantification of very low copy numbers with double-strand-specific DNA dyes requires very good amplification specificity or, as provided by the present invention, a means to differentiate the desired product from nonspecific amplification.

EXAMPLE 17

The present invention's approach to product purity determination was used to improve quantitative PCR based on once-per-cycle monitoring of double-strand-specific DNA dye fluorescence. Fluorescence was acquired once each cycle after polymerase extension of the product for a series of reactions varying in the initial concentration of purified beta-globin template (see FIG. 42A). The beta globin template and amplification conditions were as given in Example 7. The log-linear increase above background fluorescence began at a cycle number dependent on initial template concentration. The plots of the five reactions ranging from $10^6$ to $10^2$ copies per reaction were separated by about four cycles. The sample with an average $10^2$ copies per reaction showed a decrease in reaction efficiency, and reactions with initial copy number below 100 gave fluorescence profiles that were less useful. The fluorescence profiles for the reactions containing 10 and 1 (average) copies rise in reverse order, and the negative control showed amplification after about 30 cycles. This is due to amplification of primer dimers and other nonspecific amplification products that cannot be distinguished from the intended product by once-per-cycle fluorescence monitoring of double-strand-specific DNA specific dyes.

Figure 42C:
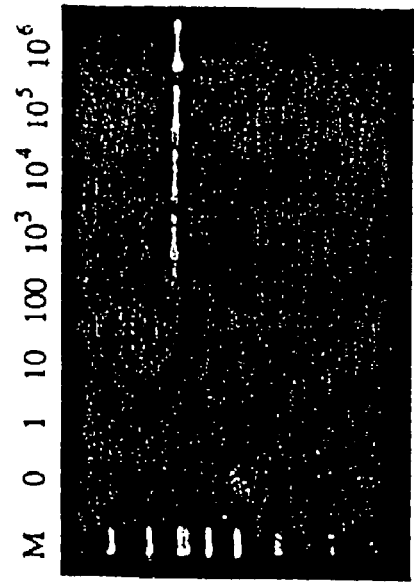

Melting peaks were acquired for each sample (FIG. 42B) and these were found to correlate well with electrophoresis results (FIG. 42C). The reaction containing zero and one average initial template copies produced no discernible electrophoresis band at the expected 536 base pair location. The reactions containing 10 and 100 initial copies of template showed weak electrophoresis bands. This agreed well with the melting peak analysis, which showed no DNA melting in the range of the intended product (90-92° C.) for the reactions containing zero and one initial copies and small peaks in this temperature range for 10 and 100 copies. Strong electrophoresis bands for the reactions containing $10^3$-$10^6$ initial copies correlate well with large melting peaks in the expected 90-92° C. range.

Figure 42D:
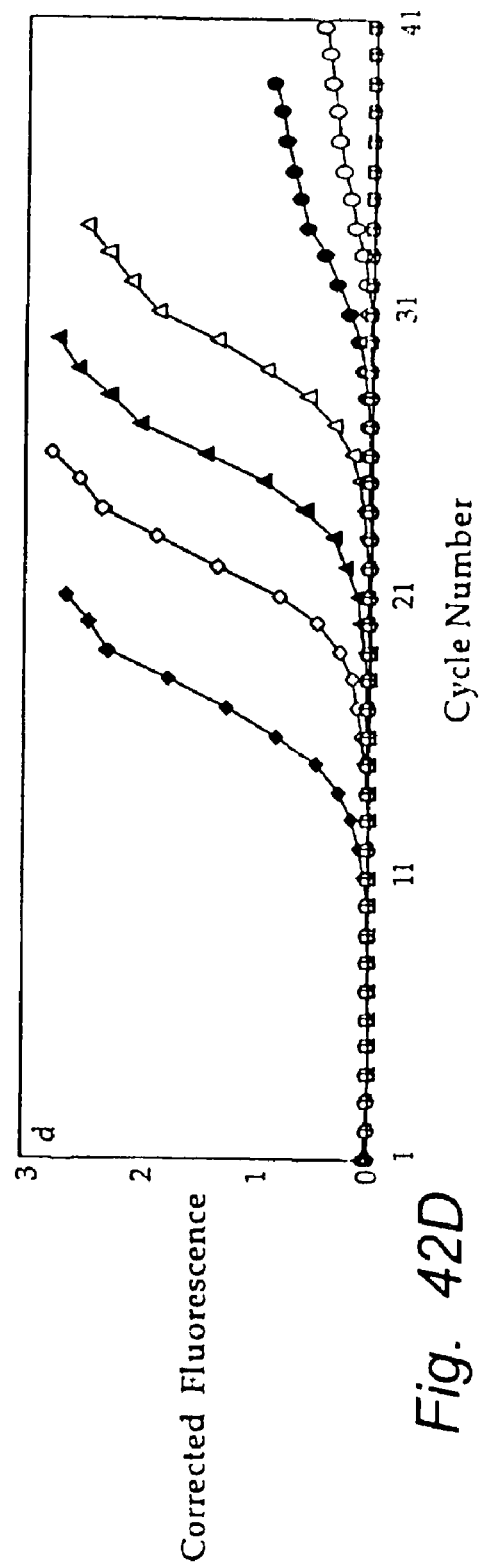

The ratio of intended product to total product, determined by melting peak integration, ranged from 0.28 for $10^5$ copies to 0.0002 for zero initial template copies. Each fluorescence value in FIG. 41A was multiplied by the appropriate ratio to give the corrected plot (designated "corrected fluorescence" in FIG. 42D). This procedure extended the effective dynamic range of quantitation to between 10 and 1 initial template copies.

Melting peaks can distinguish specific products from nonspecific products (FIG. 40) and they can distinguish two purified PCR products mixed together (FIG. 41) so they should also be useful for distinguishing two specific products amplified together in a single reaction tube. Melting curves obtained by continuous monitoring of PCR reactions according to the present invention are useful in multiplex PCR.

EXAMPLE 18

In this example, two gene fragments were simultaneously amplified from genomic DNA and monitored with SYBR™ Green I fluorescence. During each amplification cycle, different amplification products denature at melting temperatures dependent on the length of the product, GC ratio, and other factors well known in the art. The temperature at which each product melts can be monitored with the double-strand-specific dye, SYBR™ Green I. At 81 base pair fragment from the cystic fibrosis gene was amplified using the primers described herein as SEQ ID NO:14 and SEQ ID NO:15 along with a 98 base pair fragment of the c-erbB-2 (HER2/neu) oncogene using the primers described herein as SEQ ID NO:16 and SEQ ID NO:17.

Amplification reactions were comprised of 50 mM Tris-HCl, pH 8.3, 3 mM $MgCl_2$, 500 µg/ml of bovine serum albumin, 200 µM of each dNTP, and 0.5 µM of the cystic fibrosis primers, 0.3 µM of the HER2/neu primers, a 1:30,000 dilution of SYBR™ Green I, 1 U AmpliTaq Gold DNA polymerase (Perkin Elmer, Foster City, Calif.), and 50 ng of human genomic DNA in 10 µl.

Figure 43A:
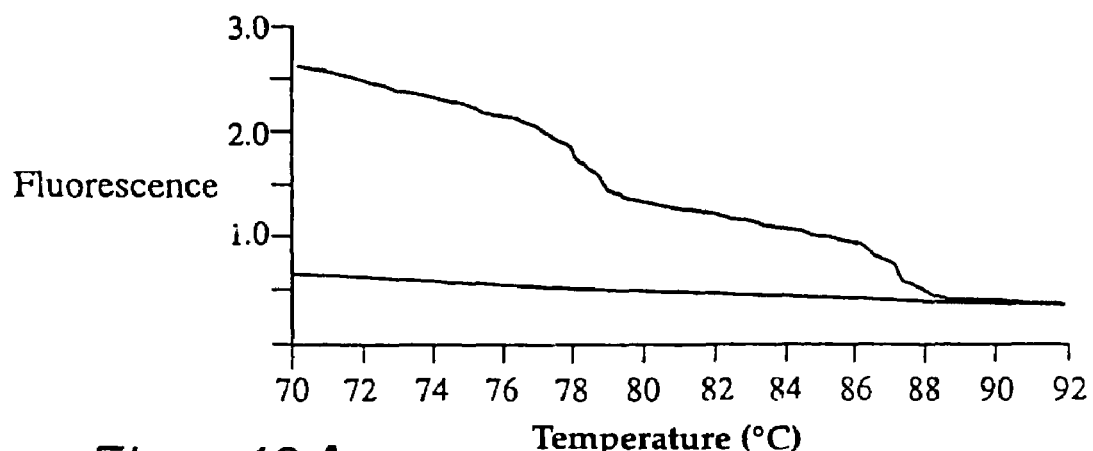
FIGS. 43A&B show (A) melting curves and (B) melting peaks from PCR amplified products of a mixture of the cystic fibrosis gene and the c-erbB-2 oncogene.
Figure 43B:
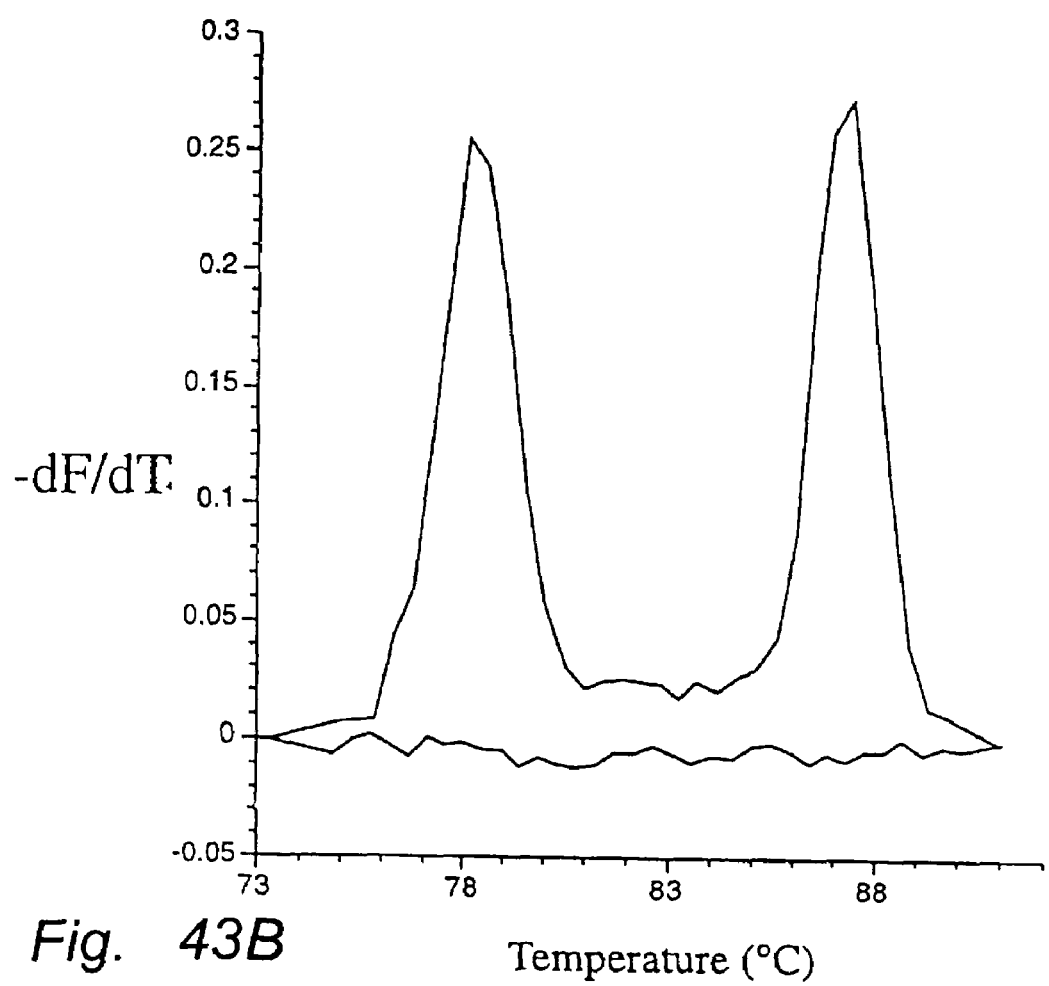

After activation of the polymerase at 95° C. for 30 minutes, the samples were cycled at 94° C. for 0 seconds (slope=20), 55° C. for 0 seconds (slope=20), and 70° C. (slope=20) for 35 cycles. The samples were cooled to 70° C., and the fluorescence was continuously acquired during a 0.2° C./sec ramp to 94° C. Melting curves (FIG. 43) clearly showed two distinct products melting at 78° C. (CFTR) and 88° C. (neu). The two products differ in Tm by approximately 10° C. and are easily distinguishable.

Multiplex amplification is useful in cases where an internal control is needed during amplification. For example, many translocations are detectable by PCR by placing primers on each side of the breakpoint. If no amplification occurs, the translocation is not present as long as the DNA is intact and no inhibitor is present. These possibilities can be ruled out by amplifying a positive control locus in the same reaction mixture. Such control amplifications are best done as internal controls with simultaneous amplification and detection.

EXAMPLE 19

Figure 44:
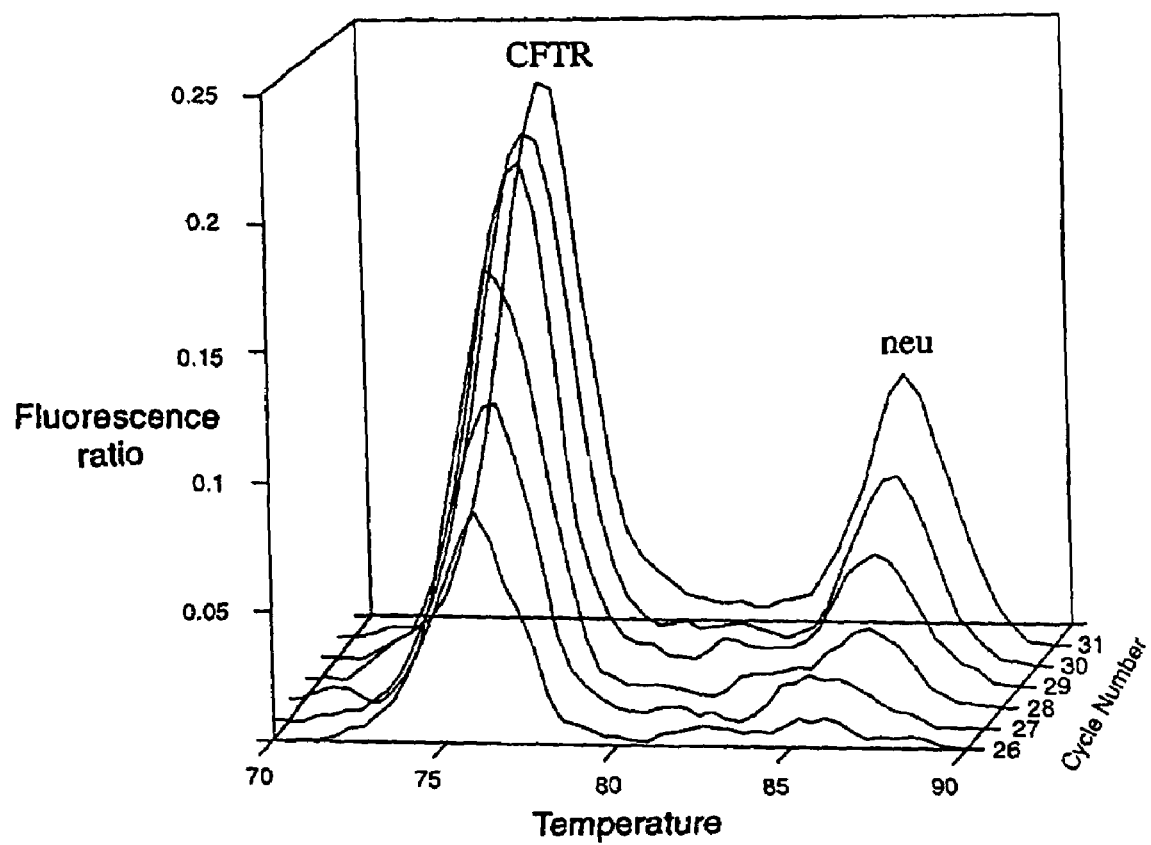
FIG. 44 show melting peaks at various cycle numbers for the cystic fibrosis gene (CFTR) and c-erbB-2 (neu).

In this example, the procedure of Example 18 was followed except that after activation of the polymerase at 95° C. for 30 minutes, the samples were cycled at 94° C. for 0 seconds (slope=20), 55° C. for 0 seconds (slope=20), and 70° C. for 10 seconds (slope=20) for 20 cycles, followed by 94° C. for 0 seconds (slope=1), 55° C. for 0 seconds (slope=20), and 70° C. for 20 seconds (slope=20) for 15 cycles. For cycles 26-31, fluorescence was continuously acquired during each 1° C./sec transition from 70° C. to 94° C. The melting curves were converted to melting peaks and displayed (FIG. 44). Note that the amplification efficiency of the CFTR fragment appears greater than the neu fragment. The amplification efficiency can be rigorously determined by integrating the melting peak data as in Example 16.

This kind of quantitative data referenced to a control has many applications. For instance, certain oncogenes, such as HER2/neu, are amplified in vivo in many tumors. That is, the genes are replicated in genomic DNA, sometimes many fold. Often, the clinical behavior of the tumor depends on the degree of oncogene replication. Amplification of the oncogene and a control template allows quantitative assessment of the relative copy number. As a further example, quantification of viral load in patients infected with HIV or hepatitis C is important in prognosis and therapy. Using a control template and monitoring the efficiency of amplification of both control and natural templates during amplification, accurate quantification of initial template copy number is achieved.

The present invention's feature of using melting curves for relative quantification will now be explained. In accordance with the present invention, an additional use for melting curves is quantitative PCR. FIG. 42 showed there was a correlation between the area under the melting peak and the amount of specific product. Relative quantification of two PCR products would be possible if the two products were amplified with similar efficiency (or if the differing efficiencies were known and compensated for). Relative quantification of two products by integrating melting peak areas (see Example 16) is an aspect of the current invention.

EXAMPLE 20

Figure 45:
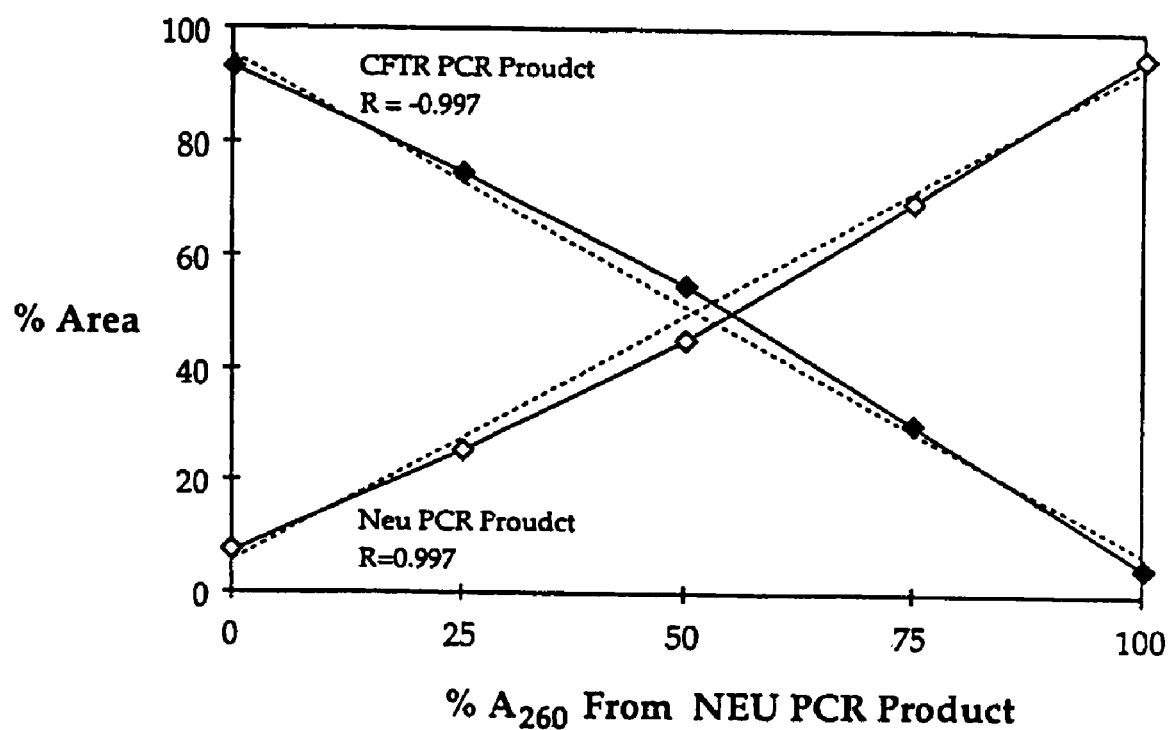
FIG. 45 shows a graph of integrated melting peaks of CFTR and neu PCT products.

The cystic fibrosis and HER-2-neu gene fragments of Example 18 were amplified, purified as in Example 2 and adjusted to 175 μg/ml. The samples were mixed in various ratios (total 8 μl) and added to buffer (1 μl) and SYBR™ Green I(1 μl). Final concentrations were 50 mM Tris, pH 8.3, 3 mM MgCl$_2$, 250 μg/ml bovine serum albumin, and a 1:30,000 dilution of SYBR™ Green I. Melting curves were acquired at 0.2° C./sec, background fluorescence subtracted and the peaks integrated as described in Example 16. The results are displayed in FIG. 45. Excellent correlation was found between the relative areas under melting peaks and the relative amounts of the two products.

Relative quantification of two PCR products is important in many quantitative PCR applications. Multiplex amplification of two or more products followed by integration of the areas under the melting peaks will be extremely useful in these areas. mRNA is often quantified relative to the amount of mRNA of a housekeeping gene.

Another important use of relative quantification is in competitive quantitative PCR. Typically a competitor is synthesized that has the same priming sites, but differs in length from the original target sequence. Known amounts of the competitor are spiked into an unknown sample and relative quantitation is performed. Competitors can be made that differ from the target sequence in Tm rather than length. The relative amounts of the products can be quantified by comparing the areas under their melting peaks. As the amount of one of the products is known, the quantity of the original target can be obtained. Using the melting peak method is significantly easier than the currently used methods which involve running multiple tubes for each unknown sample and often pulling tubes at various cycle numbers during the reaction to find the log-linear portion of the reaction. The relative amounts of the two products must then be determined. Usually this is done by labeling one of the dNTPs with a radioisotope and then quantifying the amount of label incorporated into each band after agarose gel electrophoresis. In comparison, the current invention allows the reaction to be monitored continuously so the log-linear portion of the amplification can be easily identified. Relative quantification can be done quickly by integration of melting peaks. An all day process is reduced to less than an hour.

From the foregoing discussion, it will be appreciated that fluorescence monitoring during DNA amplification is an extraordinarily powerful analytical technique. When sequence-specific detection and quantification are desired, resonance energy transfer probes can be used instead of double-strand-specific DNA dyes. The Tm of hybridization probes shifts about 4-8° C. if a single base mismatch is present. If a hybridization probe is placed at a mutation site, single base mutations are detectable as a shift in the probe melting temperature.

EXAMPLE 21

The factor V Leiden mutation is a single base change (G to A) that substitutes a glutamine residue for an arginine residue at amino acid residue 506 (R506Q). For further information, see R. M. Bertina et al., Mutation in Blood Coagulation Factor V Associated with Resistance to Activated Protein C, 369 Nature 64-67 (1994) and J. Voorberg et al., Association of Idiopathic Venous Thromboembolism with a Single Point-Mutation at Arg$^{506}$ of Factor V, 343 Lancet 1535-36 (1994), both of which are hereby incorporated by reference. As used herein, "factor V Leiden mutation locus" means the nucleotide position in the factor V gene at which a guanine base in the wild type is replaced by an adenine base in the factor V Leiden mutant. SEQ ID NO:9 shows a portion of the wild type factor V gene, and SEQ ID NO: 10 shows the corresponding portion of the factor V Leiden gene, with the relevant nucleotide at position 31 in each case. The complete nucleotide sequence of the factor V gene is described at R. J. Jenny et al., Complete cDNA and Derived Amino Acid Sequence of Human Factor V, 84 Proc. Nat'l Acad. Sci. USA 4846-50 (1987), hereby incorporated by reference, and sequences can also be obtained at Genbank locus HUMF10. The amino acid change in the mutant factor V protein makes this clotting factor resistant to degradation and increases the tendency to clotting and thrombosis. As the most common cause of inherited thrombophilia, this mutation is the target of a common laboratory test done in clinical molecular genetics laboratories.

The standard method of analysis for the factor V Leiden mutation is to amplify the gene segment by PCR, digest the resulting amplified products with a restriction endonuclease that cuts the wild type sequence but not the mutant, and distinguish digested wild type and undigested mutant products by gel electrophoresis. R. M. Bertina et al., supra. This is a method well known in the art for analysis for defined mutations. Such a test usually requires about 4 hours, including PCR amplification (2 hours), enzyme digestion (1 hour), and electrophoresis (1 hour). Post-amplification steps include opening the sample tube, adding the enzyme, and transferring the digested sample to the electrophoresis apparatus. Post-amplification processing increases the risk of end product contamination, and manual handling requires care to prevent mislabeling of samples. A method that simultaneously amplifies and analyzes for point mutations would eliminate these concerns.

A method for complete amplification and analysis of the factor V Leiden mutation within 30 min in the same instrument comprises asymmetrically amplifying a portion of a human genomic DNA sample containing the mutation locus, followed by obtaining and analyzing a melting curve for the amplified DNA. Genomic DNA is prepared according to methods well known in the art, e.g. J. Sambrook et al., Molecular Cloning: A Laboratory Manual (2d ed., 1989), hereby incorporated by reference. Preferably, the melting curve is obtained by the resonance energy transfer methodology described above with a fluorogenic hybridization probe. Such an assay easily discriminates between homozygous wild type, homozygous mutant, and heterozygous genotypes. In a preferred embodiment, the oligonucleotide probe is 3'-labeled with fluorescein and designed to hybridize on the amplified DNA near to a Cy5-labeled primer for resonance energy transfer. This method can be applied to any defined mutation.

The probe oligonucleotide is preferably about 15-40 nucleotide residues in length. The probe could conceivably contain as few as about 10 nucleotide residues, however, possible disadvantages of such short oligonucleotides include low specificity, low melting temperature, and increased background. Oligonucleotides larger than 40 residues could also be used, but would be unnecessarily expensive. Thus, the limits on the size of the probe oligonucleotide are only those imposed by functionality. The probe oligonucleotide should span the mutation, but the mutation preferably does not correspond to either the 5'- or 3'-terminal nucleotide residue of the probe. Since the present invention is based on melting curves, and lack of base pairing at the termini is known to have less of an effect on melting properties than at internal sites, the probe should be designed such that the mutation occurs at an internal position.

The oligonucleotide primers for amplification of the selected mutation locus are preferably about 15 to 30 residues in length. Primers shorter than the preferred range could be used but may not be as specific as would be desired. Similarly, primers longer than the preferred range could be used, but would be unnecessarily expensive. Thus, the limits on the sizes of the PCR primers are only those imposed by functionality.

The distance between the resonance energy transfer pair is also important for the proper functioning of the invention. The optimum distance between the resonance energy transfer pair is about 5 nucleotides. A distance of about 2 to 8 nucleotides is preferred, although a distance of up to about 10-15 nucleotides is functional. Having the resonance energy transfer pair on adjacent nucleotides is not necessarily beneficial because the distance between the resonance energy transfer pair is effected by the position on the DNA helix.

In this example, PCR amplification was carried out in 10 μl reaction mixtures comprising 50 mM Tris, pH 8.3, 3 mM MgCl$_2$, 500 μg/ml bovine serum albumin, 200 μM each dNTP, 0.5 μM Cy5-labeled primer (SEQ ID NO:11), 0.2 μM unlabeled opposing primer (SEQ ID NO:12), 0.1 μM fluorescein-labeled probe (SEQ ID NO:13), 0.4 U Taq polymerase, and fifty ng human genomic DNA. Four different samples of DNA were tested: human genomic DNA from an individual homozygous for the factor V Leiden mutation; human genomic DNA from a heterozygous individual; human genomic DNA from an individual homozygous for the wild type factor V allele; and a negative control without DNA. The orientation of the Cy5-labeled primer, the fluorescein-labeled probe, and the mutation site (identified by asterisk) are shown below:

the probe. A 5-base separation between the hybridized fluorophores and a mutation at base 8 of a 23-mer probe gave a melting curve shift of 8° C. between mutant and wild type sequences (FIG. 46).

Mutation detection by probe melting can also be performed with 2 labeled probes instead of one labeled probe and one labeled primer. In this embodiment, one probe is labeled 5' with Cy5 and the other probe is labeled 3' with fluorescein. Since both these fluorescent probes can be synthesized directly from the amidites, a manual synthesis step is not required as it is in the primer/probe system. The fluorescein-labeled probe should be designed such that the mutation locus is near the center of the fluorescein-labeled probe. The length of the Cy5-labeled probe should be designed such that it melts at a higher temperature (>5° C.) than the fluorescein-labeled probe which spans the mutation locus. Because background from fluorescein is more troublesome than that from Cy5, the concentration of the Cy5-labeled probe should preferably be 2-5 fold that of the fluorescein-labeled probe. The two probes should hybridize to the same strand of genomic DNA, and the resonance energy transfer pair should be separated by about 0 to 5 nucleotide residues. Alternately, the probe that spans the mutation site can be labeled with Cy5 and the other probe labeled with fluorescein.

It will be appreciated that the particular probes and primers disclosed herein for detection of the factor V Leiden mutation are merely illustrative, and that a person of ordinary skill in the art will be able to design other probes and primers for detection of mutations without undue experimentation by

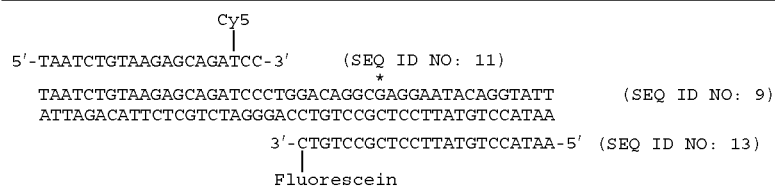

Figure 47:
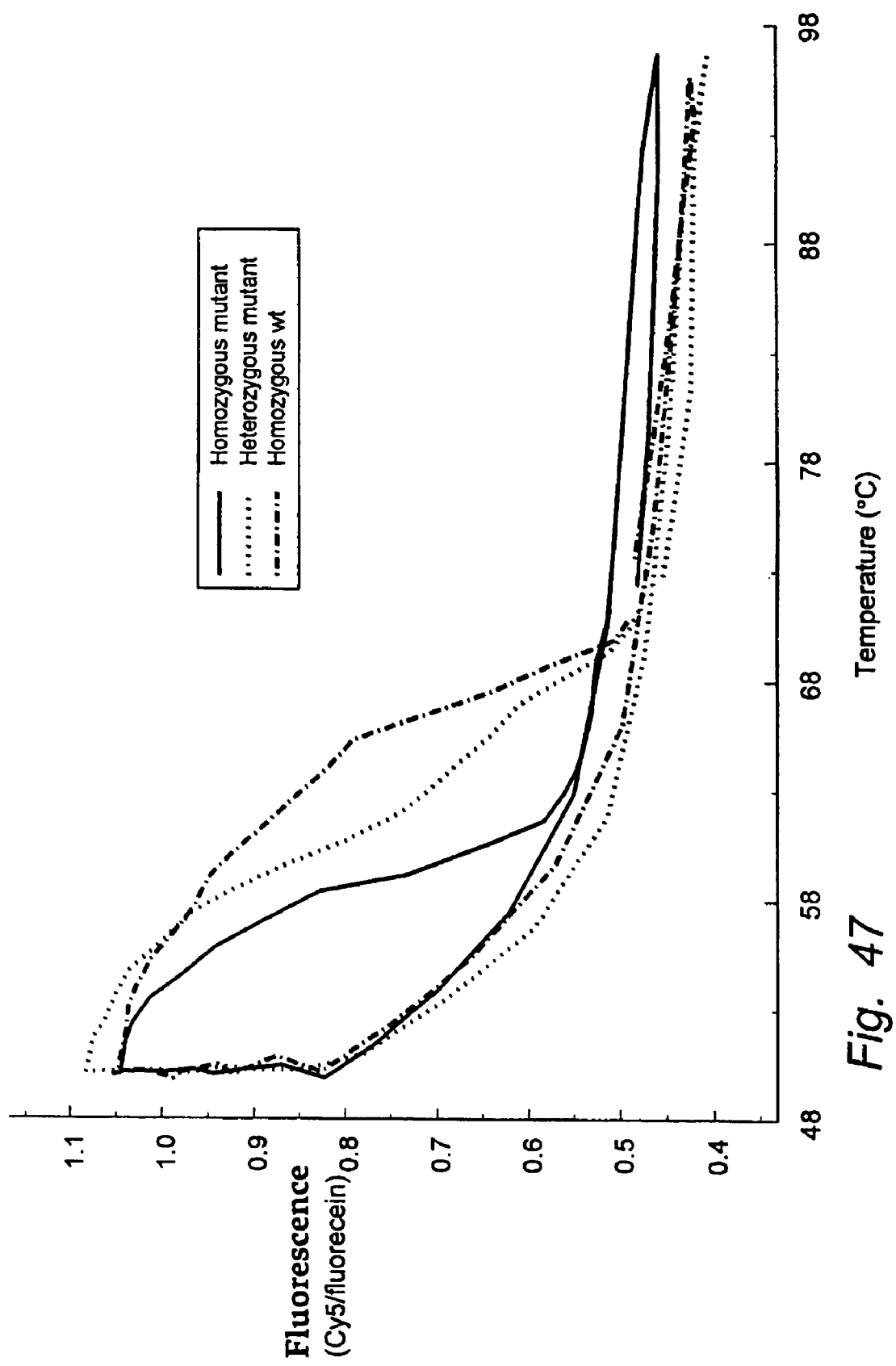
FIG. 47 shows a fluorescence ratio v. temperature plot of continuous monitoring during cycle 40 of PCR products of a sample homozygous for the factor V Leiden mutation (solid line), heterozygous for the factor V Leiden mutation (dotted line), and homozygous wild type (alternating dot and dash).

The sequence of the unlabeled opposing primer was TGT-TATCACACTGGTGCTAA (SEQ ID NO:12) and the amplified product was 186 base pairs in length. The Cy5-labeled primer was obtained as in Example 8. Cycling conditions were 94° C. for 0 sec (slope=20), 50° C. for 10 sec (slope=20), and 72° C. for 0 sec (slope=1) for 50 cycles, followed by cooling to 45° C. and continuous fluorescence monitoring at a slope of 0.2° C./sec to 94° C. for the melting curve. The highest quality melting curves were obtained at the end of amplification with a slow temperature transition rate (0.2° C./sec—FIG. 46), although monitoring during each cycle at 1° C./sec between 50° C. and 94° C. also provided clear genotype identification (FIG. 47). The melting curves are easiest to visualize by plotting the negative derivative of fluorescence with respect to temperature vs temperature (−dF/dT vs T). Such a plot allows facile visual identification of all possible genotypes from the raw fluorescence data.

The closer the Cy5 label is to the primer's 3'-end, the greater the resonance energy transfer signal. However, the 3'-end must have a free 3'-hydroxyl for polymerase extension, and placing the Cy5 too close to the 3'-end (either on the 3' or penultimate base) may inhibit polymerase attachment and extension. The 3'-fluorescein probe should hybridize as close to the primer as possible (minor overlap of 1-3 bases can be tolerated) and the mutation site should be near the middle of following the principles and guidelines set forth herein. It should also be recognized that although the invention is described with respect to detection of a single base mutation in genomic DNA, the same principles can be applied to detection of a mutation in cDNA. Preparation of the cDNA requires extra process steps and time, as is well known in the art, thus it is preferred to use genomic DNA because of the advantages of speed and lower cost. Further, the same technique can be used to detect insertions and deletions by designing the hybridization probe so that it melting temperature changes when the mutation or polymorphism is present. The invention can be used to detect any known mutation where a probe can be designed to differ in melting temperature when hybridized to mutant vs wild type.

Although fluorescein and Cy5 were used as resonance energy transfer labels in the example above, other acceptors, such as Cy5.5, can also be used with fluorescein.

EXAMPLE 22

The factor V locus of Example 21 was amplified as before except that the primer was labeled with Cy5.5 instead of Cy5. Cy5.5 emission was observed through a 683 nm long pass dichroic and a 683-703 nm bandpass interference filter. The Cy5.5 to fluorescein ratio increased above background at about cycle 30 and the ratio approximately doubled by 50 cycles of asymmetric amplification. When amplified with wild type DNA, the probe Tm was 65-66° C. as judged by melting peaks.

Another example for detecting single base mutations will now be given.

EXAMPLE 23

Figure 48:
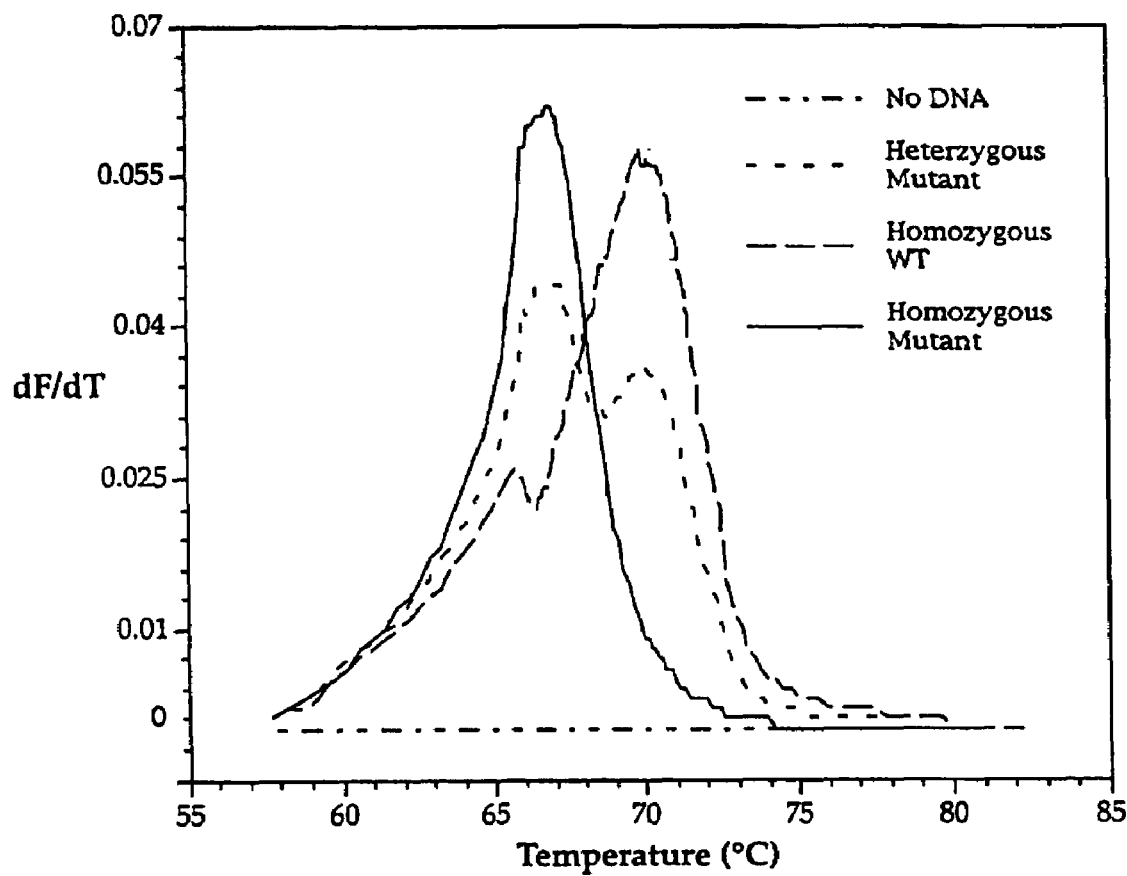
FIG. 48 shows melting peaks of a homozygous mutant of the methylenetatrahydrofolate gene (solid line), homozygous wild type (broken line), heterozygous mutant (dotted line), and no DNA control (alternating dot and dash).

There is a common point mutation in the methylenetetrahydrofolate reductase (MTHFR) gene ($C_{677}T$) that converts an alanine to a valine residue and results in a thermolabile enzyme. This mutation can reduce MTHFR activity and lead to elevated homocysteine plasma levels which has been implicated as an independent risk factor for early vascular disease and thrombosis as is well known in the art. One of the primers was labeled with Cy5 (TGAAGGAGAA GGTGTCT*GCGGGA) (SEQ ID NO:25) where T* represents a modified T residue linked to Cy5 (see Example 9 for synthesis and purification). The probe sequence was fluorescein-CCTCGGCTAAATAGTAGTGCGTCGA (SEQ ID NO:26) and the other primer was AGGACGGTGCGGT-GAGAGTG (SEQ ID NO:27). A 198 base pair fragment of the MTHFR gene was amplified from 50 ng of human genomic DNA in 50 mM Tris, pH 8.3, 2 mM $MgCl_2$, 500 µg/ml bovine serum albumin, 0.2 mM of each dNTP, 0.5 µM of the Cy5-labeled primer, 0.1 µM of the opposing primer, 0.1 µM of the fluorescein-labeled probe, and 0.4 U Taq DNA polymerase per 10 µl. Each cycle was 30 sec long and consisted of denaturation at 94° C. followed by a 20 sec combined annealing/extension step at 60° C. The temperature transition rate between steps was 20° C./sec. After 60 cycles, a melting curve was acquired as follows: heating from 50-65° C. at 0.5° C./sec, 65-75° C. at 0.1° C./sec, a 0.5° C./sec. After baseline subtraction and conversion to melting peaks, all possible genotypes were easily distinguished (FIG. 48).

The discriminatory power of hybridization probes is also used to great advantage in multiplex or competitive PCR. For example, an artificial template is designed with a single internal base change and a hybridization probe designed to cover the base change as in Examples 21 and 23. Relative amplification of the competitor and natural template are determined by acquiring and integrating melting peaks as in Example 16. Alternately, if multiple detection probes are used that sequentially melt off different targets at different temperatures, relative quantification is achieved by the same analysis. In general, any quantitative technique described previously for double-strand-specific DNA dyes can be made sequence specific with hybridization probes.

Absolute Product Concentration by Product Reannealing Kinetics. Product concentration determinations are also advantageously carried out using the present invention. Continuous monitoring of double stranded DNA formation allows DNA quantification at any cycle of amplification by reannealing kinetics. The sample temperature is quickly dropped from the denaturation temperature and held constant at a lower temperature that is still high enough to prevent primer annealing (FIG. 2). The rate of product reannealing follows second order kinetics (see B. Young & M. Anderson, Quantitative analysis of solution hybridization, In: Nucleic Acid Hybridization: A Practical Approach 47-71 (B. Hames & S. Higgins, eds., (1985), which is now incorporated herein by reference). For any given PCR product and temperature, a second order rate constant can be measured. Once the rate constant is known, any unknown DNA concentration can be determined from experimental reannealing data. Cooling is never instantaneous, and some reannealing occurs before a constant temperature is reached. Rapid cooling will maximize the amount of data available for rate constant and DNA concentration determination. The technique requires pure PCR product, but such can be assured by melting curves also obtained during temperature cycling using the present invention. This method of quantification by the present invention is advantageously independent of any signal intensity variations between samples.

EXAMPLE 24

Figure 49:
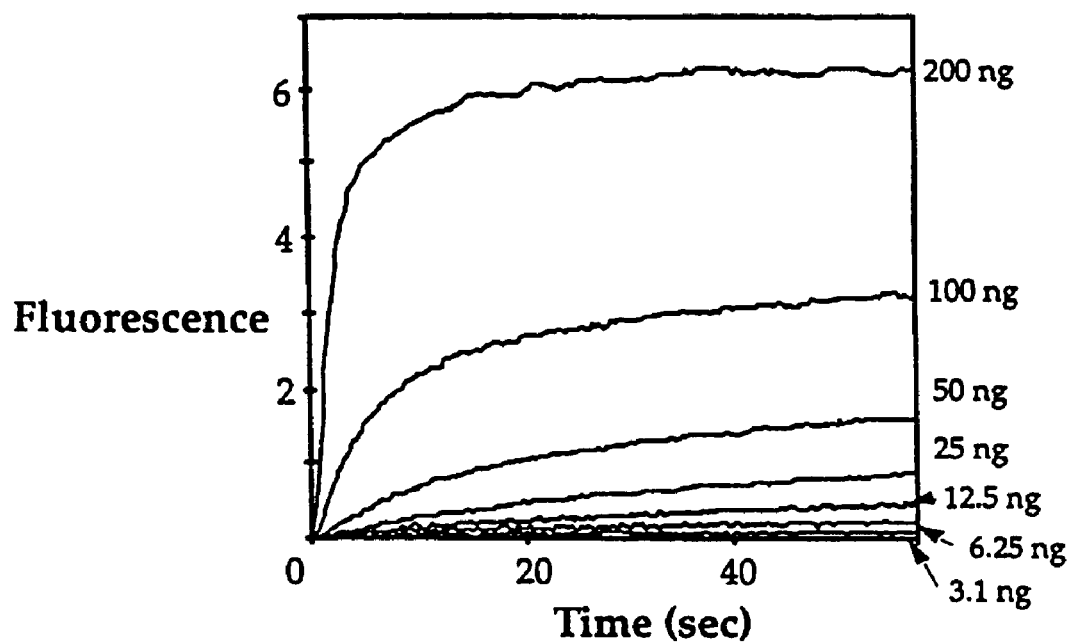
FIG. 49 shows the shape of reannealing curves of amplified β-globin PCR products from various initial template amounts.
Figure 50:
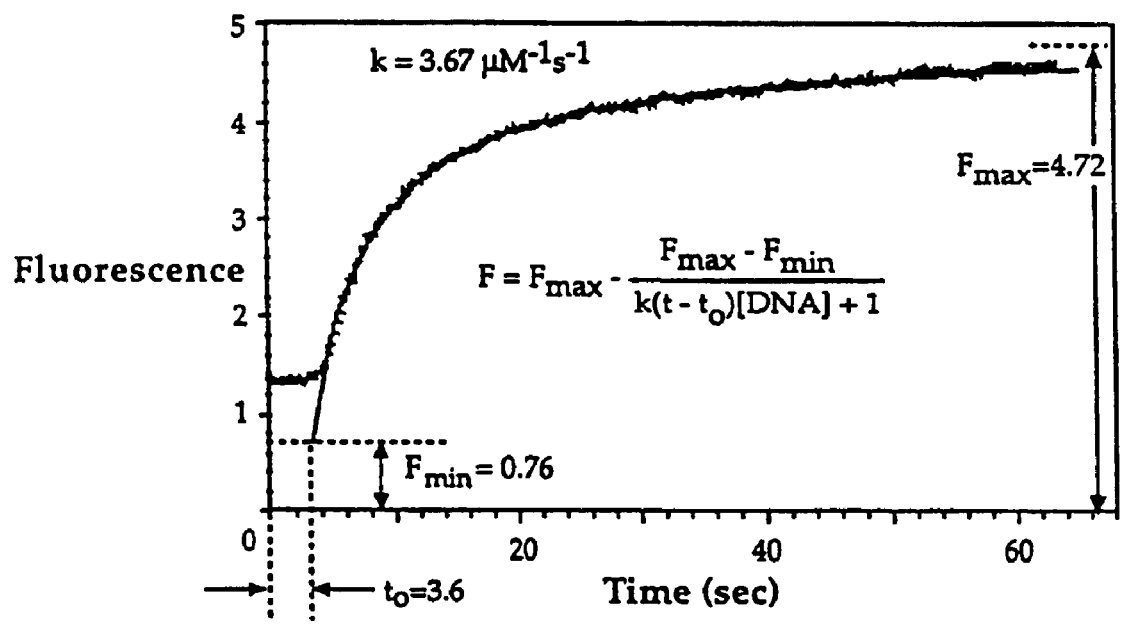
FIG. 50 shows the determination of a second order rate constant for determining initial template concentration.

A 536 base pair fragment of the beta-globin gene was amplified from human genomic DNA (Example 7) and purified (see Example 2). Different amounts of the purified DNA were mixed with a 1:30,000 dilution of SYBR™ Green I in 5 µl of 50 mM Tris, pH 8.3 and 3 mM $MgCl_2$. The samples were denatured at 94° C. and then rapidly cooled to 85° C. The fluorescence at 520-550 nm was monitored at 85° C. over time. When different concentrations of DNA were tested, the shape of the reannealing curve was characteristic of the DNA concentration (See FIG. 49). For any given PCR product and temperature, a second order rate constant can be determined. FIG. 50 shows the determination of a second order reannealing rate constant for 100 ng of the 536 base pair fragment in 5 µl at 85° C. The curve was fit by non-linear least squares regression with $F_{max}$, $F_{min}$, $t_0$ and k as the floating parameters using the second order rate equation shown in FIG. 50. Analysis programs for this kind of curve fitting are well known in the art (for example, the user defined curve fit of Delta Graph, DeltaPoint, Inc, Monterey, Calif.). Once the rate constant is known, an unknown DNA concentration can be determined from experimental reannealing data.

With the rate constant (k) defined, DNA concentrations are determined on unknown samples. The fluorescence vs time curves of unknown samples are fit by non-linear least squares regression, preferably during temperature cycling in real time (for example, using the nonlinear Levenberg-Marquardt method described in the LabView programming environment, National Instruments, Austin, Tex.). For this fit, $F_{max}$, $F_{min}$, $t_0$, and [DNA] are the floating parameters and k is constant.

Since some fluorescent dyes affect reannealing in a concentration dependent manner, the assumption of second order kinetics for product reannealing is checked by determining the rate constant at different standard DNA concentrations. The relationship is defined and alternate formula for fitting incorporated as necessary.

Also within the scope of the present invention is to use probe annealing rates to determine product concentrations. The rate of fluorescence resonance energy transfer is followed over time after a quick drop to a probe annealing temperature that is greater than the primer annealing temperature (FIG. 2). For the case of amplification with a labeled primer and one labeled probe, the rate of annealing (and fluorescence generation) is second order. When using two labeled probes, the rate of fluorescence development is third order. These two arrangements are shown in FIG. 18. When the concentration of the probe(s) is much greater than the product concentration, pseudo-first order and pseudo-second order equations are adequate to describe the possibilities. The appropriate rate equations for these different conditions are well known in the art (see Young, B. and Anderson, M., supra). For the purposes of this invention, it is adequate that the prior art suggests appropriate rate equations that are tested experimentally and corrected if necessary.

When probe annealing rates are used to determine product concentrations, possible interfering effects include product reannealing (with probe displacement by branch migration) and primer annealing and extension through the probe. The later is minimized when the probe Tm's are higher than the primer Tm's and a probe annealing temperature is chosen to minimize primer annealing. FIG. 13 shows that even if extension occurs, the fluorescence increases with time for about 20 sec. During this period, the fluorescence increase depends on product concentration.

Probe annealing rates are used to determine product concentration similar to the method described above for determining product concentration by product reannealing. The steps are summarized as follows: (1) choosing the appropriate rate equation for the system, (2) running known DNA standards to determine the rate constant, (3) checking the validity of the rate equation by comparing different rate constants derived from different concentrations, and (4) using the rates constants to determine the DNA concentration of unknowns from their probe annealing data.

Fluorescence Feedback for Control of Temperature Cycling. In contrast to endpoint and cycle-by-cycle analysis, the present invention can also monitor fluorescence throughout each temperature cycle. Continuous fluorescence monitoring can be used to control temperature cycling parameters. The present invention uses fluorescence feedback for real time control and optimization of amplification. Continuous fluorescence monitoring of PCR samples containing a double-strand-specific DNA dye or fluorescently labeled oligonucleotide probes can be used to monitor hybridization and melting during individual amplification cycles. This information can be used by the temperature control algorithms within the temperature cycling apparatus to improve and customize thermal cycling conditions. Conventional PCR is performed by programming all cycling parameters before amplification. With continuous monitoring, determination of temperature cycling requirements can occur during amplification, based on continuous observation of annealing, extension, and denaturation. The potential benefits of using hybridization information to control temperature cycling include:

1. Ensuring complete denaturation of the PCR product each cycle while:
   a. Minimizing exposure to excessively high denaturation temperatures thus avoiding heat-induced damage to the amplification products and polymerase. Limiting the time product is exposed to denaturation temperatures is especially useful for amplification of long products.
   b. Increasing reaction specificity by minimizing the denaturation temperature. This selects against products with a Tm higher than the intended amplification product.
2. Maximizing the amplification efficiency by ensuring adequate time for primer annealing each cycle while:
   a. Minimizing the amount of time required for amplification by allowing no longer than is needed to reach a certain efficiency of primer annealing.
   b. Enhancing reaction specificity by minimizing the time at the annealing temperature.
3. Maximizing the amplification efficiency by ensuring adequate time for product extension each cycle while:
   a. Minimizing the amount of time required for amplification by allowing no longer than needed to complete product extension.
   b. Enhancing reaction specificity by selecting against products longer than the intended amplification product. These would require longer than the allotted time to complete product extension.
4. Initiating thermal cycling changes dependent on the level of fluorescence obtained or the current efficiency of amplification. For example, over-amplification and nonspecific reaction products can be minimized by terminating thermal cycling when the efficiency drops to a certain level. As another example, temperature cycling can be modified to initiate slower temperature ramps for melting curve acquisition when the fluorescence becomes detectable. This saves time because the slower ramps need not be used on earlier cycles. Other desirable changes may become evident on continued practice of the invention.

Control is based on an estimate of reaction parameters from the fluorescence data. The original fluorescence data is either acquired as a change in fluorescence over time (temperature specific rates of denaturation, annealing, and extension), a change in fluorescence over temperature (product or probe Tm), or a change in extent of amplification (amplification yield and efficiency). These rates, Tm's and their first and second derivatives are used to determine optimal reaction parameters that include denaturation temperature and time, primer annealing temperature and time, probe annealing temperature and time, enzyme extension temperature and time, and number of cycles.

Double-strand-specific DNA dyes are used for the control of denaturation, control of extension, and to initiate thermal cycling changes at a certain amplification level or efficiency. Resonance energy transfer dyes are used for the control of annealing as will be described after the following example.

EXAMPLE 25

Figure 53:
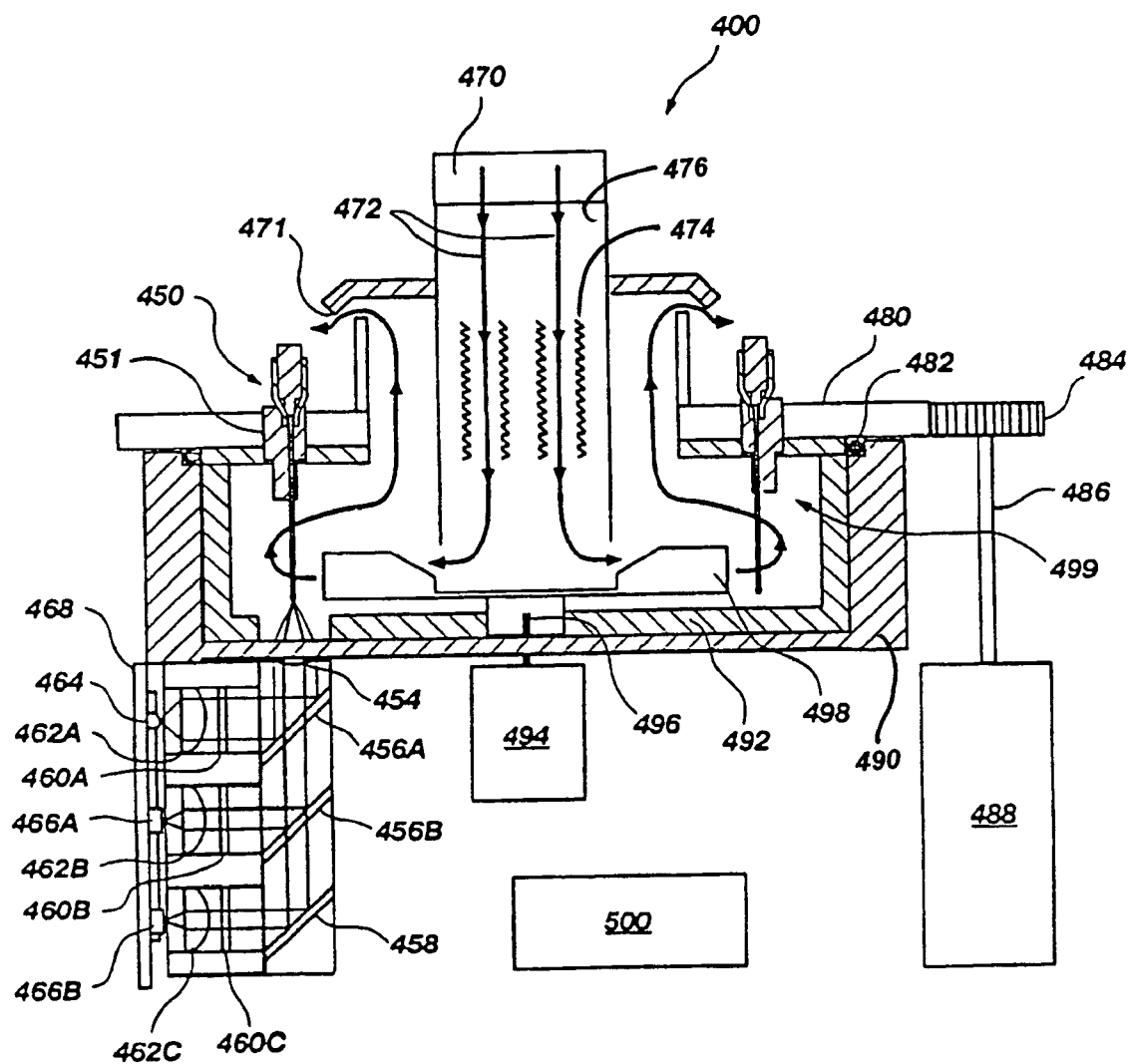
FIG. 53 is a schematic diagram of an illustrative thermal cycler for the present invention.

Illustratively, thermal cycling may be performed on a thermal cycler 400 as illustrated in FIG. 53. In the embodiment represented in FIG. 53, air is taken in through an aperture 470 and generally follows the flow path indicated by the lines 472. The temperature of the air, and thus the temperature of the plastic/glass sample container 450, is preferably adjusted using a heat exchange component such as a 400 watt heating cartridge 474 which is preferably one available from Reheat, Inc. The heating cartridge 474 is positioned within a central duct 476. A fan 498 is provided to move the air in the indicated path 472. The fan is driven via a shaft 496 and a motor 494. The motor 494 is preferably a DC rare earth brush motor which is preferably available from Escap AG. and having a maximum rpm of 15,000. When heating the plastic/glass sample tubes 450, the heating cartridge is proportionally controlled and the fan is run at a relatively low speed (12 volts, 0.5 amp) to provide temperature homogeneity for all of the plastic/glass sample containers 450. When cooling the plastic/glass sample containers 450, the heating cartridge 474 is disabled and the motor 494 is run at a fast speed (for example with the above-mentioned preferred motor maximum speed is obtained by applying 27 volts, 1.4 amps). The fan 498 forces air into the aperture 470 and out via exhaust ports 471.

In the illustrative temperature cycler with epifluorescence detection 400, twenty-four plastic/glass sample containers 450 (two of which are represented in FIG. 53) are symmetrically arranged around the heating cartridge 474 and the central duct 476. The plastic/glass sample containers 450 are received by sleeves 451 which (due to their offset structure) allow for precise adjusting of the position of the individual plastic/glass sample containers 450 in a circular carousel 480. The sleeves 451 are illustratively fabricated from brass. The off-axis structure of the sleeve 451 allows each sleeve 451 to be aligned so that the tip of the glass/plastic sample container 450 can be precisely adjusted to be at the optical focal point represented in FIG. 53, both laterally and longitudinally, at the time that the rapid temperature cycler with epifluorescence detection 400 is fabricated.

The optical components represented in FIG. 53 carry out paraxial epifluorescent illumination of the capillary tip, which provides advantageous results not otherwise obtainable. In FIG. 53, an excitation radiation source 464 is preferably a blue LED, such as one known in the industry as a super bright LED and available from LEDtronics. The emitted fluorescence signals are acquired by photo detectors 466A and 466B. The excitation radiation source 464 and the photo detectors 466A and 466B are supported on a mounting board 468 which also includes necessary circuitry and which integrates filters with the photo detectors 466A and 466B. A preferred mounting board is available from Ealing Electrooptics which includes 0.5 inch interference filters with high performance silicon photodiodes in TO5 packages. The excitation and detection components are supported directly on the mounting board 468 with associated electronics. It is preferred that the optical components are preferably $\leq 1.0$ inches in diameter. A collimating lens 454, two dichroic filters 456A and 456B, a mirror 458, interference filters 460 A-C, and aspheric focusing lenses 462 A-C direct the radiation to and from the sample.

While the embodiment of the present invention represented in FIG. 53 utilizes only two colors/wavelengths when performing an analysis, those skilled in the art can readily adapt the embodiment to provide three, or more, color analysis. To provide three or more color analysis, the apparatus represented in FIG. 53 can accommodate additional dichroic filters and photo detectors. Moreover, it is within the scope of the present invention to allow simultaneous separation of wavelengths onto a linear photo detector array, as is available in the industry, for multicolor acquisition. When a linear photo detector array-is used in accordance with the present invention, it is preferred that a prism or diffraction grating be utilized in cooperation with a lens and a photo detector array or CCD for detection of multiple wavelengths. One preferred linear photo detector array available in the industry collects 15-30 wavelength bins of 10-20 nm each between 500 and 800 nm. Various configurations of optical components, for example the Littrow autocollimating configuration for gratings used in most monochrometers, can be arrived at using the information set forth herein to arrive at the best accommodation between collection efficiency, spectral resolution and spatial requirements.

When detection of SYBR™ Green I emissions is desired, one of the filters is preferably a 520-580 nm band pass filter, available from Omega as model no. 550RDF60, which is preferably used for single wavelength acquisition. For detection of other emissions, other wavelength filters 456A and 456B can be used. For example, a 520-550 nm band pass filter, preferably available from Omega, model no. 535DF30, may be used for detection of fluorescein; and a 580-620 nm band pass filter, preferably available from Omega, model no. 600DF40, may be used for detection of rhodamine. Those skilled in the art will readily appreciate that the use of other components can be readily implemented using the information set forth herein in order to accommodate other fluorescent wavelengths.

The carousel 480 is supported on a bearing 482 above a housing 490. The carousel 480 is positioned by a stepper motor 488 provided with a drive gear 484 connected to the motor 488 via a shaft 486. The stepper motor 488 is microstepped (using a controller (not explicitly represented in FIG. 53) from New England Affiliated Technologies) to provide over 10,000 steps per revolution of the carousel 480, providing precise positioning of each the plastic/glass sample containers 450. The interior of the housing 490 is provided with an insulative material 492. Baffles 476 function to form the exhaust port 471 and to block ambient light.

Still referring to FIG. 53, a user interface and instrument control 500 can be provided. As one illustrative example of a user interface and instrument control 500, a PENTIUM™ microcomputer running the LabView programming language with a 12-bit multifunction input/output card (available from National Instruments) provides data acquisition and control. It is preferred that the analog output signals be used to adjust the amplifiers associated with the photo detectors 466A and 466B. Analog input channels also measure the temperature of the samples via a thermocouple 499 as well as the fluorescent detected from the sample by the photodiodes. The user interface and instrument control 500 represented in FIG. 53 also provides digital I/O control of the excitation radiation source 464, the direction of the stepper motor 488, the heating cartridge 474, and the fan 498.

When continuous fluorescence monitoring of PCR samples containing the dsDNA dye SYBR™ Green I or fluorescently labeled oligonucleotide probes can be used to monitor hybridization and melting during individual amplification cycles. This information can be used by preferred arrangements for the user interface and instrument control 500 to provide improved and customized thermal cycling conditions.

In accordance with the present invention, the user interface and instrument control 500 can follow preprogrammed time/temperature set points and/or, advantageously, can acquire detected fluorescence values and then use the acquired detected fluorescence values to alter or adjust one or more reaction parameters in real time to optimize the results obtained. As used herein, the term "reaction parameter" includes, but is not limited to, any parameter which is used as a basis for controlling a reaction. Such reaction parameters include, but are not limited to, denaturation temperature and time, primer annealing temperature and time, probe annealing temperature and time, enzyme extension temperature and time, and number of cycles. In general, control of the reaction is initially based on an estimate of reaction parameters from the fluorescence data. The original fluorescence data is either acquired as a change in fluorescence over time (temperature specific rates of denaturation, annealing, and extension), a change in fluorescence over temperature (product or probe $T_m$), or a change in extent of amplification (amplification yield and efficiency). These rates, $T_m$'s and their first and second derivatives, are used to determine optimal reaction parameters such as denaturation temperature and time, primer annealing temperature and time, probe annealing temperature and time, enzyme extension temperature and time, and number of cycles.

A commercial fluorescence monitoring thermal cycler (LC24 LightCycler, Idaho Technology Inc., Idaho Falls, Id.) was modified so that the software is no longer programmed with temperature/time setpoints, but is programmed to acquire fluorescence values, then to use these values for thermal cycler control.

Figure 51:
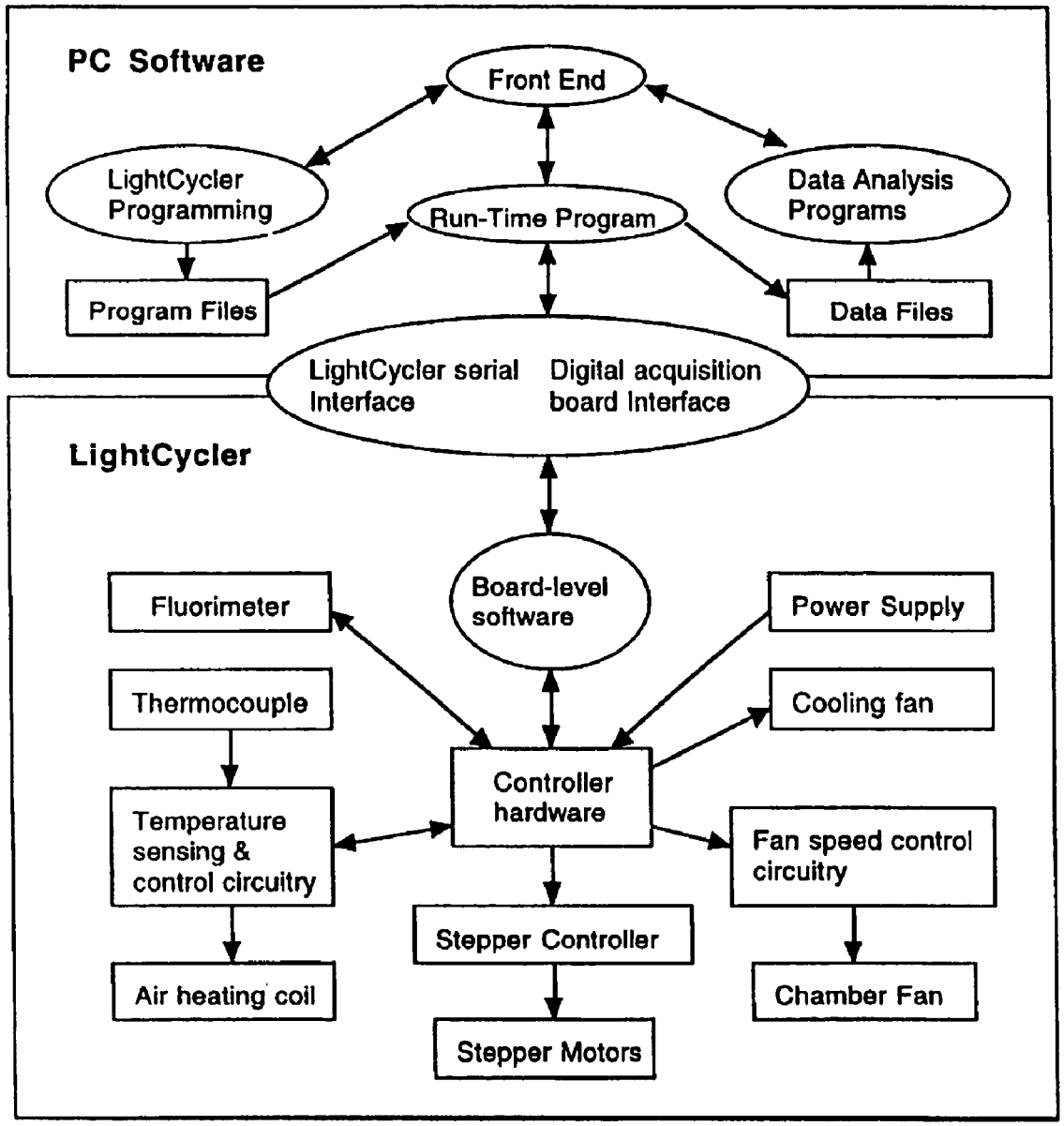
FIG. 51 shows a block diagram for controlling thermal cycling from fluorescence data.

As depicted in the Functional Block Diagram (FIG. 51), the Run-Time Program communicates through serial and DAQ-board interfaces with the LightCycler. This allows high level access to either temperature or fluorescence data and either can be used by the Board-level Software for temperature control. However, in the current embodiment of the instrument, only the temperature data is converted into digital form at the Controller Hardware level. The fluorescence data is sent in analog form through the Digital acquisition board interface, is analyzed by the Run-time Program, and is sent back to the Board-level software via the serial interface.

Product Melting Control:

A melting peak was acquired for the intended PCR product and a baseline fluorescence was acquired for the sample containing the reaction cocktail at the temperature at which the product was completely melted.

Each cycle of the reaction then used this fluorescence value as a target. The approach to product denaturation was made in two stages to overcome the time-lag due to the requirement of sending the fluorescence value to a remote computer for analysis, then returning the instruction that the value had been reached. With each product melting step, the temperature was increased until the fluorescence reached an intermediate value, then the heating power was reduced so that a temperature ramp rate of roughly 3°/sec gave the computer time to analyze the fluorescence and signal the thermal cycler that product denaturation had occurred.

Figure 52A:
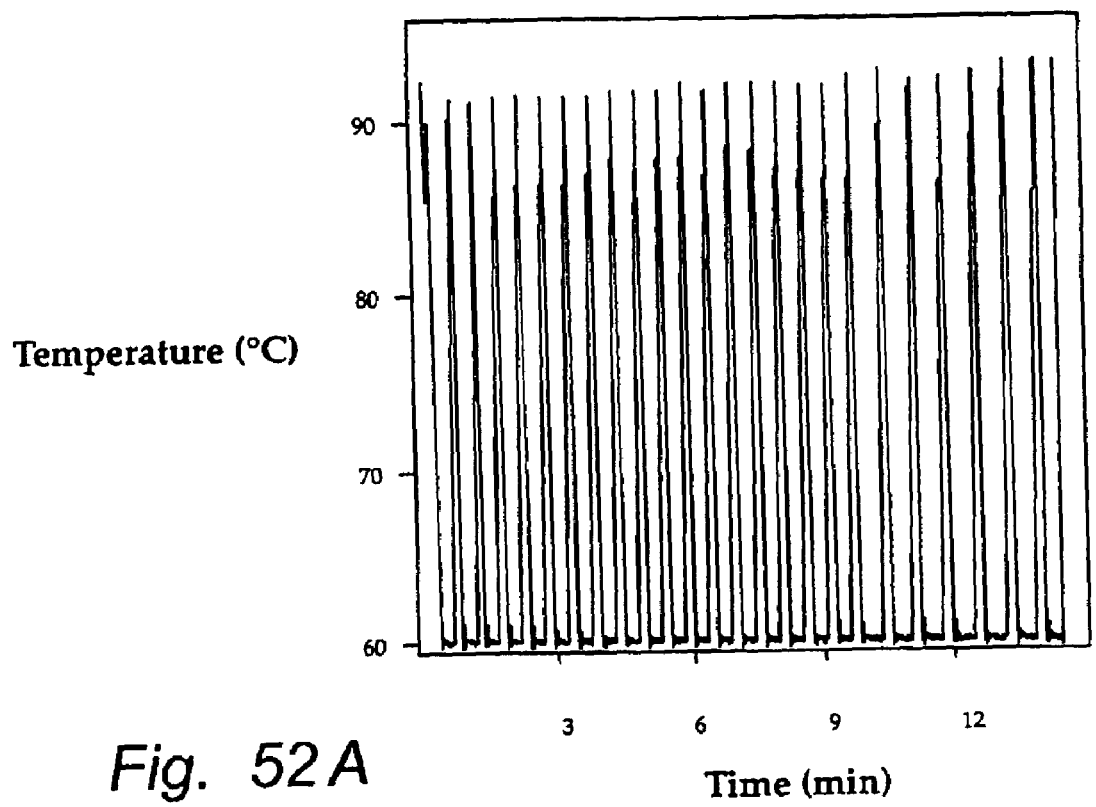
FIGS. 52A&B show (A) a temperature v. time plot acquired after 20 cycles and (B) a fluorescence v. time plot acquired after 25 cycles wherein thermal cycling was controlled from fluorescence data.
Figure 52B:
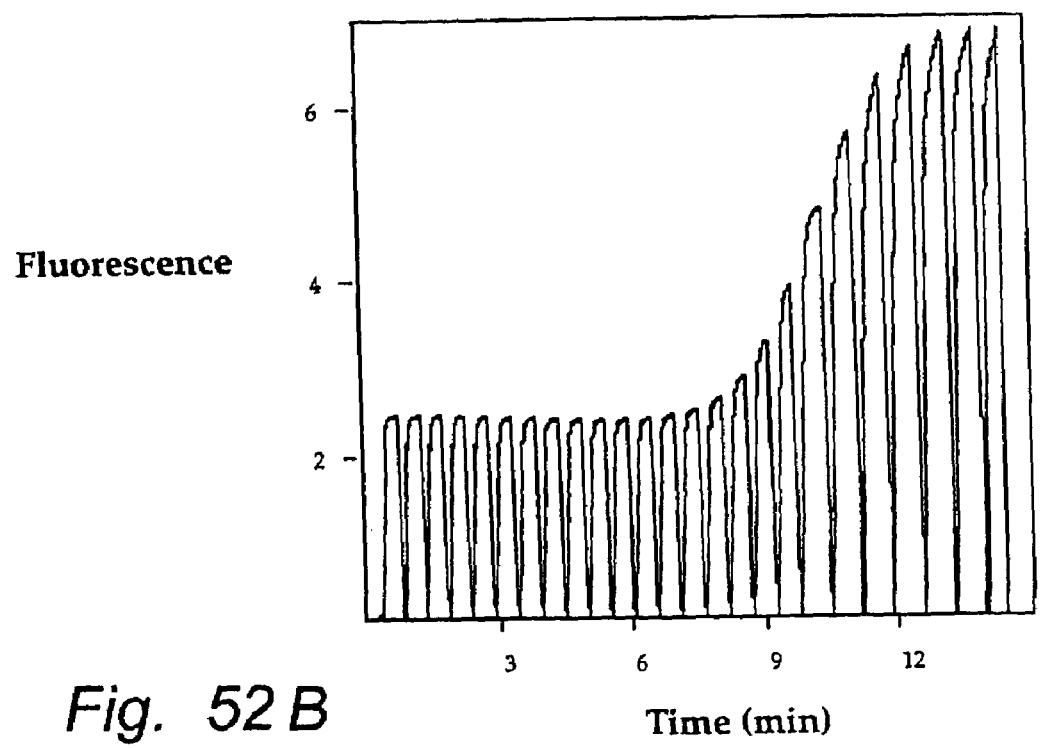

The resulting temperature/time plot (FIG. 52) shows a characteristic increase in the melting temperature after cycle 20 as the concentration of amplification product increases. Product Tm is a function of product concentration.

Product Annealing/extension:

During an extended hold at a combined annealing/extension temperature, the fluorescence was monitored and this information was used to ensure that adequate, but not excessive time had been allowed for product extension. The fluorescence was monitored at 10 second intervals, if the fluorescence increased more than a settable ratio (typically 1.00-1.05 ), then the annealing/extension step was continued. Otherwise, the next product melting step was initiated. The interval of 10 seconds was chosen to give a minimum of 20 seconds at the combined annealing/extension temperature.

The resulting fluorescence/time plot (FIG. 52) shows a characteristic increase in the dwell time at the combined annealing/extension temperature as the concentration of amplification product grows. As the primer concentration and polymerase become limiting, more time is needed to complete product extension with each cycle.

Amplification Plateau:

At the end of each annealing/extension step, the fluorescence value was acquired and stored. When this value had increased to 1.2 times the lowest end-cycle fluorescence value and had subsequently stopped increasing below a user settable ratio (typically 1.00-1.02), the thermal cycling was terminated. Alternately, a melting-curve acquisition step was initiated by entering a slow 0.1-0.2° C./second temperature ramp through the product Tm and monitoring the fluorescence of the sample continuously.

The resulting fluorescence/time plot (FIG. 52) shows that after twenty-five cycles of amplification the ratio of cycle-by-cycle fluorescence growth fell below 1.00 and the reaction was terminated.

In one embodiment of the present invention, detection of the amplification plateau is used to acquire a high-resolution melting curves for each sample in a multiple sample run at the optimal temperature cycle for each sample. As a sample reaches its amplification plateau, a melting-curve is acquired for that sample, then regular temperature cycling is resumed until another reaction reaches its amplification plateau.

Real time monitoring and control of annealing distinct from extension is also provided by the present invention. If one of the primers is 3'-labeled with Cy5, no extension can occur. However, if labeled primer (1-10%) is mixed with unlabeled primer (90-99%), amplification efficiency will be slightly decreased, but annealing is observable as fluorescence energy transfer from a double-strand-specific dye to Cy5. The primer with the lowest Tm (as determined by nearest neighbor thermodynamics as known in the art) is labeled with Cy5 and SYBR™ Green I is included as a double-strand-specific dye. Alternately, primer annealing can be monitored indirectly with equivalent complementary oligonucleotides. An oligonucleotide of the same length and Tm as the lowest melting primer is designed with no complementarity to the amplified sequence. This oligonucleotide is 5'-labeled with Cy5 and its complement is 3'-labeled with fluorescein or some other resonance energy transfer pair. Hybridization of these oligonucleotides is followed by resonance energy transfer. The concentration of one probe is made the same as the concentration of the lowest Tm primer and the concentration of the other probe is made much less than this in order to obtain pseudo-first-order kinetics that approximates the pseudo-first-order kinetics of primer annealing to product. The efficiency of annealing is monitored and used to control annealing temperature and times by one of these methods.

It is also within the scope of the present invention to entirely replace temperature and time setpoints with fluorescence feedback control. For example, three samples are placed in a fluorescence temperature cycler with feedback capacity. The samples are:

1. A non-reacting sample containing amplified product and SYBR™ Green I.

2. A non-reacting sample containing complementary fluorescently labeled primers with a Tm equal to the lowest Tm primer and concentrations as noted above.

3. The sample to be amplified and SYBR™ Green I.

With each cycle of amplification, product denaturation is ensured by monitoring sample 1 as the temperature is increased. A melting curve is determined in real-time and when the sample has denatured, the transition to the annealing step is begun. Primer annealing is monitored indirectly through the hybridization of two complementary primers in sample 2. One of the primers is 3' labeled with fluorescein and the other is 5' labeled with Cy5 or similar dye. The temperature is decreased until sample 2 shows primer hybridization as indicated by an increase in the ratio of fluorescence at 670 nm/540 nm. This ratio increases due to resonance energy transfer between the fluorophores when they are approximated by hybridization. Product extension is followed by monitoring the fluorescence of one or more of the actual samples as demonstrated in Example 25.

Summary. From the foregoing discussion, it will be appreciated that continuous fluorescence monitoring during DNA amplification to monitor hybridization is an extraordinarily powerful analytical technique. Using the methods described herein and depending on the number of initial template copies present, product identification and quantification can be achieved in five to twenty minutes after temperature cycling has begun. The present invention achieves several advantages not heretofore available in the art. For example, the present invention provides single-color fluorescence methods to monitor product purity, relative quantitation by multiplex PCR or competitive PCR, absolute product quantification by reannealing kinetics, and an improved method for initial template quantification by fluorescence vs cycle number plots. The present invention also provides dual-color, sequence-specific methods for sequence variation detection, relative quantitation by multiplex PCR or competitive PCR, product quantification by probe annealing kinetics, and initial template quantification by fluorescence vs cycle number plots.

The following table compares double-strand-specific DNA dyes, hydrolysis probes, and hybridization probes useful in continuous monitoring of PCR. The fluorescence of double-strand-specific DNA dyes depends on the strand status of the DNA. The dual-labeled hydrolysis probes are quenched while intact and donor fluorescence increases when the probe is hydrolyzed. Hybridization probes depend on increased resonance energy transfer when hybridization brings 2 fluorophores closer together.

Summary of Fluorescent Probes for Continuous Monitoring of PCR

|  | dsDNA dye | Fluorescent Probe Hydrolysis | Hybridization |
|---|---|---|---|
| Mechanism | Strand status | Quenching | Transfer |
| Probe Synthesis | Unnecessary | Difficult | Simple |
| Specificity | Product Tm | Sequence | Sequence |
| Melting Analysis | Yes | No | Yes |
| Multicolor Analysis | No | Yes | Yes |

In accordance with the present invention, time, temperature and fluorescence are acquired 1-10 times every sec and fine details of product and/or probe hybridization are observed during temperature cycling. With double-strand-specific DNA dyes, the hybridization of product with respect to temperature is used to identify products by melting curves. In addition, relative product quantification is achieved by multiplex amplification of two or more different products that differ in Tm. Further, competitive PCR is performed by altering the sequence internal to the common primers so that two or more products have different Tm's. Absolute product quantification is obtained by rapidly cooling the denatured product and observing reannealing kinetics. The sensitivity of initial template quantification with fluorescence vs cycle number plots is increased by analysis of product melting curves to control for nonspecific amplification and curve fitting algorithms. Finally, immediate fluorescence feedback for control of denaturation conditions, elongation times and product yield are obtained by monitoring product strand status with double-strand-specific DNA dyes.

The ability to monitor probe hybridization with fluorescence during temperature cycling is a powerful tool. The present invention provides dual-color fluorescence methods that depend on probe hybridization (not hydrolysis) for sequence-specific detection and quantification during PCR. The annealing kinetics and melting of hybridization probes provides information not available with probes that rely on exonuclease hydrolysis between fluorophores. Continuous monitoring of sequence-specific probe hybridization can be followed over temperature changes by resonance energy transfer. Probe melting occurs at a characteristic temperature determined by its sequence and complementarity to the product. Two schemes have been detailed by the present invention, (1) two adjacent hybridization probes, and (2) one labeled probe that hybridizes to a single stranded PCR product that incorporates a labeled primer. The melting temperature of sequence-specific probes identifies and discriminates products during PCR. DNA polymorphisms or mutations, including single base mutations, are detected by probe Tm shifts. In addition, relative product quantification is achieved by multiplex amplification of at least two different products with one or more probes that melt from their respective products at different temperatures. Further, competitive PCR is performed by altering the sequence internal to the primers so that one or more probes hybridize to the competitor and the natural template at different Tm's. Alternately, relative or competitive PCR are performed by multicolor analysis with probes labeled with different fluorophores, such as Cy5 and Cy5.5. Absolute product concentration is determined by analysis of probe annealing kinetics. Initial template copy number is determined from fluorescence vs cycle number plots by curve fitting algorithms.

When multiplex analysis in one PCR reaction is desired, it is common practice to use different fluorescent labels with distinguishable emission spectra to identify the multiple products. The analysis is complicated by the limited number of fluorophores available and the overlapping emission spectra of those fluorophores that are available (see H M Shapiro, supra). Analysis of product or probe hybridization with melting curves is another method to distinguish multiple PCR products. By following hybridization during temperature cycling, the number of probes and/or spectral colors needed to distinguish multiple products can be minimized.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

Programming code for carrying out melting curve and other analyses is found in the Programming Code Appendix (Microfiche) to U.S. application Ser. No. 08/869,276, already incorporated by reference.

The attached Sequence Listing is identical to the Sequence Listing contained in U.S. application Ser. No. 08/869,276, filed Jun. 4, 1997.

The invention claimed is:

1. A device for performing PCR and monitoring the reaction of a sample comprising a nucleic acid and a fluorescent dye comprising:
   a reaction vessel with the sample therein, wherein the sample further comprises a polymerase and a pair of primers configured for amplifying a locus of the nucleic acid,
   a heat exchange component for heating and cooling the sample,
   a control device programmed for repeatedly operating the heat exchange component to subject the sample to thermal cycling to generate an amplification product,
   an excitation source for optically exciting the sample to cause the sample to fluoresce,
   a photodetector for detecting temperature-dependent fluorescence levels from the sample, and
   a processor programmed to generate a melting curve of the amplification product contained within the reaction vessel during or subsequent to amplification.

2. The device of claim 1 wherein the device further comprises a chamber in thermal communication with the heat exchange component, and the chamber is further configured for receiving the reaction vessel.

3. The device of claim 1 wherein the heat exchange component further comprises a heater and a fan for heating and cooling forced air which is in thermal contact with the reaction vessel.

4. The device of claim 1 wherein the heat exchange component comprises a heat block device.

5. The device of claim 1 wherein the control device is programmed to repeatedly operate the heat exchange component between an annealing temperature and a denaturation temperature, where the denaturation temperature is sufficient to denature the amplification product, and the fluorescent dye is SYBR® Green I

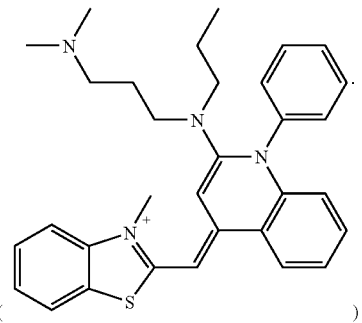

6. The device of claim 5 wherein the processor is further programmed to generate an amplification curve.

7. The device of claim 1 wherein the photodetector is configured to detect temperature-dependent fluorescence levels from the sample during amplification.

8. The device of claim 1 wherein the melting curve is a derivative plot.

9. The device of claim 1 wherein the fluorescent dye is a double-stranded nucleic acid binding dye.

10. The device of claim 1 wherein the control device operates the heat exchange device to heat the sample at a rate of $\geq 0.1°$ C./second.

11. A device for performing PCR and monitoring the reaction of a sample comprising a nucleic acid and a double-stranded nucleic acid binding dye comprising:
    a heat exchange component for heating and cooling the sample,
    a control device programmed for repeatedly operating the heat exchange component to subject the sample to thermal cycling,
    an excitation source for optically exciting the sample to cause the sample to fluoresce, a photodetector for detecting temperature-dependent fluorescence levels from the sample,
a processor programmed to generate a melting curve during or subsequent to amplification, and
further comprising a reaction vessel with the sample therein, wherein the sample further comprises a polymerase and a pair of primers configured for amplifying a locus of the nucleic acid.

12. The device of claim 11 wherein the dye is SYBR® Green I

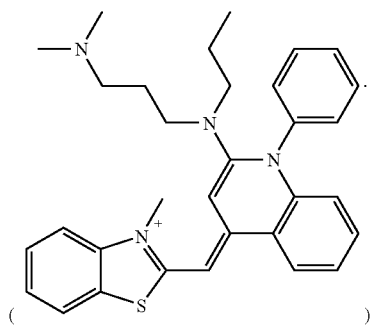

13. The device of claim 5, wherein the denaturation temperature is in excess of 90° C.

14. A device for performing PCR and monitoring the reaction of a sample comprising a nucleic acid and a fluorescent dye comprising:
    a reaction vessel with the sample therein, wherein the sample further comprises a polymerase and a pair of primers configured for amplifying a locus of the nucleic acid,
    a heat exchange component for heating and cooling the sample,
    a control device programmed for repeatedly operating the heat exchange component to subject the sample to thermal cycling to generate an amplification product,
    an excitation source for optically exciting the sample to cause the sample to fluoresce,
    a photodetector for detecting temperature-dependent fluorescence levels from the sample,
    a processor programmed to generate a melting curve of the amplification product contained within the reaction vessel during or subsequent to amplification; and
    wherein the sample further comprises at least one nucleic acid probe labeled with the fluorescent dye.

* * * * *

(12) EX PARTE REEXAMINATION CERTIFICATE (10717th)
United States Patent
Wittwer et al.

(10) Number: US 7,670,832 C1
(45) Certificate Issued: Sep. 22, 2015

(54) SYSTEM FOR FLUORESCENCE MONITORING

(75) Inventors: Carl T. Wittwer, Salt Lake City, UT (US); Kirk M. Ririe, Salt Lake City, UT (US)

(73) Assignee: University of Utah Research Foundation

Reexamination Request:
No. 90/012,369, Jun. 21, 2012

Reexamination Certificate for:
Patent No.: 7,670,832
Issued: Mar. 2, 2010
Appl. No.: 11/203,947
Filed: Aug. 15, 2005

Related U.S. Application Data

(60) Continuation of application No. 10/397,759, filed on Mar. 26, 2003, now Pat. No. 7,160,998, which is a continuation of application No. 09/799,160, filed on Mar. 5, 2001, now Pat. No. 6,569,627, which is a continuation of application No. 09/635,344, filed on Aug. 9, 2000, now Pat. No. 6,232,079, which is a division of application No. 08/869,276, filed on Jun. 4, 1997, now Pat. No. 6,174,670, which is a continuation-in-part of application No. 08/818,267, filed on Mar. 17, 1997, now abandoned, which is a continuation-in-part of application No. 08/658,993, filed on Jun. 4, 1996, now abandoned.

(51) Int. Cl.
*C12M 1/00* (2006.01)
*C12Q 1/68* (2006.01)
*B01L 3/00* (2006.01)
*G01N 21/25* (2006.01)
*G01N 21/64* (2006.01)
*B01L 7/00* (2006.01)

(52) U.S. Cl.
CPC ............ *B01L 3/5082* (2013.01); *B01L 7/52* (2013.01); *C12Q 1/686* (2013.01); *C12Q 1/6818* (2013.01); *C12Q 1/6823* (2013.01); *G01N 21/253* (2013.01); *G01N 21/6428* (2013.01); *G01N 21/6452* (2013.01)

(58) Field of Classification Search
None
See application file for complete search history.

(56) References Cited

To view the complete listing of prior art documents cited during the proceeding for Reexamination Control Number 90/012,369, please refer to the USPTO's public Patent Application Information Retrieval (PAIR) system under the Display References tab.

*Primary Examiner* — Sharon Turner

(57) ABSTRACT

The prevent invention is directed to devices for performing PCR and monitoring the reaction of a sample comprising a nucleic acid and a fluorescent dye. Illustrative devices comprise a heat exchange component for heating and cooling the sample, a control device for repeatedly operating the heat exchange component to subject the sample to thermal cycling an excitation source for optically exciting the sample to cause the sample to fluoresce, a photodetector for detecting temperature-dependent fluorescence levels from the sample, and a processor configured to record and process emissions from the fluorescent dye.

EX PARTE REEXAMINATION CERTIFICATE

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claims 1, 10-11 and 14 are determined to be patentable as amended.

Claims 2, 4 and 7-9, dependent on an amended claim, are determined to be patentable.

New claims 15-17 are added and determined to be patentable.

Claims 3, 5-6 and 12-13 were not reexamined.

1. A device for performing PCR and monitoring the reaction of a sample comprising a nucleic acid and a fluorescent dye comprising:
 a reaction vessel with the sample therein, wherein the sample further comprises a polymerase and a pair of primers configured for amplifying a locus of the nucleic acid *and wherein the fluorescent dye in the sample provides a detectable signal that can be used to generate a melting curve*,
 a heat exchange component for heating and cooling the sample,
 a control device programmed for repeatedly operating the heat exchange component to subject the sample to thermal cycling to generate an amplification product,
 an excitation source for optically exciting the sample to cause the sample to fluoresce,
 a photodetector for detecting temperature-dependent fluorescence levels from the sample, and
 a processor programmed to generate [a] *the* melting curve of the amplification product contained within the *same* reaction vessel [during or] *in which the amplifying takes place*, subsequent to amplification.

10. The device of claim 1 wherein the control device operates the heat exchange device to heat the sample at a rate of ≥0.1° C./second *while the processor generates the melting curve*.

11. A device for performing PCR and monitoring the reaction of a sample comprising a nucleic acid and a double-stranded nucleic acid binding dye, *wherein the dye provides a detectable signal that can be used to generate a melting curve*, comprising:
 a heat exchange component for heating and cooling the sample,
 a control device programmed for repeatedly operating the heat exchange component to subject the sample to thermal cycling,
 an excitation source for optically exciting the sample to cause the sample to fluoresce,
 a photodetector for detecting temperature-dependent fluorescence levels from the sample,
 a processor programmed to generate [a] *the* melting curve during or subsequent to amplification, and
further comprising a reaction vessel with the sample therein, wherein the sample further comprises a polymerase and a pair of primers configured for amplifying a locus of the nucleic acid *and wherein the dye is operable to allow the generating of the melting curve to occur within the reaction vessel*.

14. A device for performing PCR and monitoring the reaction of a sample comprising a nucleic acid and a fluorescent dye comprising:
 a reaction vessel with the sample therein, wherein the sample further comprises a polymerase and a pair of primers configured for amplifying a locus of the nucleic acid,
 a heat exchange component for heating and cooling the sample,
 a control device programmed for repeatedly operating the heat exchange component to subject the sample to thermal cycling to generate an amplification product,
 an excitation source for optically exciting the sample to cause the sample to fluoresce,
 a photodetector for detecting temperature-dependent fluorescence levels from the sample,
 a processor programmed to generate a melting curve of the amplification product contained within the *same* reaction vessel [during or] subsequent to amplification; and
 wherein the sample further comprises at least one nucleic acid probe labeled with the fluorescent dye *to provide a detectable signal that can be used to generate the melting curve*.

*15. The device of claim 1, wherein the processor is programmed to generate the melting curve such that amplification products of different length, GC content, or GC distribution are distinguishable.*

*16. The device of claim 11, wherein the processor is programmed to generate the melting curve such that amplification products of different length, GC content, or GC distribution are distinguishable.*

*17. A device for performing PCR and generating a melting curve comprising:*
 *a reaction vessel with a sample therein, wherein the sample comprises a target nucleic acid, a fluorescent dye, a polymerase, and a pair of primers configured for amplifying a locus of the target nucleic acid in the same reaction vessel in which both amplification and photodetection occur and wherein the fluorescent dye in the sample provides a detectable signal that can be used to generate a melting curve,*
 *a heat exchange component for heating and cooling the sample within the reaction vessel,*
 *a control device programmed for repeatedly operating the heat exchange component to subject the sample to thermal cycling to generate an amplification product in the sample within the reaction vessel,*
 *an excitation source for optically exciting the sample within the reaction vessel to fluoresce,*
 *a photodetector for detecting temperature-dependent fluorescence levels from the sample within the reaction vessel, and*
 *a processor programmed to generate the melting curve of the amplification product within the reaction vessel, subsequent to amplification, using the temperature-dependent fluorescence levels.*

\* \* \* \* \*

SEQUENCE LISTING (1) GENERAL INFORMATION:

(iii) NUMBER OF SEQUENCES:27

(2) INFORMATION FOR SEQ ID NO:1:

(i) SEQUENCE CHARACTERISTICS:
        (A) LENGTH: 20 base pairs
        (B) TYPE: nucleic acid
        (C) STRANDEDNESS: single-stranded
        (D) TOPOLOGY: linear (xi) SEQUENCE DESCRIPTION: SEQ ID NO:1:

CGTGGTGGAC TTCTCTCAAT                                           20

(2) INFORMATION FOR SEQ ID NO:2:

(i) SEQUENCE CHARACTERISTICS:
        (A) LENGTH:  20 base pairs
        (B) TYPE:  nucleic acid
        (C) STRANDEDNESS:  single-stranded
        (D) TOPOLOGY:  linear (xi) SEQUENCE DESCRIPTION: SEQ ID NO:2:

AGAAGATGAG GCATAGCAGC                                           20

(2) INFORMATION FOR SEQ ID NO:3:

(i) SEQUENCE CHARACTERISTICS:
        (A) LENGTH:  35 base pairs
        (B) TYPE:  nucleic acid
        (C) STRANDEDNESS:  single-stranded
        (D) TOPOLOGY:  linear (xi) SEQUENCE DESCRIPTION: SEQ ID NO:3:

CAAACAGACA CCATGGTGCA CCTGACTCCT GAGGA                           35

(2) INFORMATION FOR SEQ ID NO:4:

(i) SEQUENCE CHARACTERISTICS:
        (A) LENGTH:  30 base pairs
        (B) TYPE:  nucleic acid
        (C) STRANDEDNESS:  single-stranded
        (D) TOPOLOGY:  linear (xi) SEQUENCE DESCRIPTION: SEQ ID NO:4:

AAGTCTGCCG TTACTGCCCT GTGGGGCAAG                                 30

(2) INFORMATION FOR SEQ ID NO:5:

(i) SEQUENCE CHARACTERISTICS:
        (A) LENGTH:  27 base pairs
        (B) TYPE:  nucleic acid
        (C) STRANDEDNESS:  single-stranded
        (D) TOPOLOGY:  linear (xi) SEQUENCE DESCRIPTION: SEQ ID NO:5:

TCTGCCGTTA CTGCCCTGTG GGGCAAG                                    27

(2) INFORMATION FOR SEQ ID NO:6:

(i) SEQUENCE CHARACTERISTICS:
        (A) LENGTH:  20 base pairs
        (B) TYPE:  nucleic acid
        (C) STRANDEDNESS:  single-stranded
        (D) TOPOLOGY:  linear (xi) SEQUENCE DESCRIPTION: SEQ ID NO:6:

CAACTTCATC CACGTNCACC                                            20

(2) INFORMATION FOR SEQ ID NO:7:

(i) SEQUENCE CHARACTERISTICS:
        (A) LENGTH:  18 base pairs
        (B) TYPE:  nucleic acid
        (C) STRANDEDNESS:  single-stranded
        (D) TOPOLOGY:  linear -continued (xi) SEQUENCE DESCRIPTION: SEQ ID NO:7:

CTGTCCGTGA CGTGGATT                                                          18

(2) INFORMATION FOR SEQ ID NO:8:

(i) SEQUENCE CHARACTERISTICS:
        (A) LENGTH:  18 base pairs
        (B) TYPE:  nucleic acid
        (C) STRANDEDNESS:  single-stranded
        (D) TOPOLOGY:  linear (xi) SEQUENCE DESCRIPTION: SEQ ID NO:8:

AAGTCCTCCG AGTATAGC                                                          18

(2) INFORMATION FOR SEQ ID NO:9:

(i) SEQUENCE CHARACTERISTICS:
        (A) LENGTH:  46 base pairs
        (B) TYPE:  nucleic acid
        (C) STRANDEDNESS:  single-stranded
        (D) TOPOLOGY:  linear (xi) SEQUENCE DESCRIPTION: SEQ ID NO:9:

TAATCTGTAA GAGCAGATCC CTGGACAGGC GAGGAATACA GGTATT                            46

(2) INFORMATION FOR SEQ ID NO:10:

(i) SEQUENCE CHARACTERISTICS:
        (A) LENGTH:  46 base pairs
        (B) TYPE:  nucleic acid
        (C) STRANDEDNESS:  single-stranded
        (D) TOPOLOGY:  linear (xi) SEQUENCE DESCRIPTION: SEQ ID NO:10:

TAATCTGTAA GAGCAGATCC CTGGACAGGC AAGGAATACA GGTATT                            46

(2) INFORMATION FOR SEQ ID NO:11:

(i) SEQUENCE CHARACTERISTICS:
        (A) LENGTH:  20 base pairs
        (B) TYPE:  nucleic acid
        (C) STRANDEDNESS:  single-stranded
        (D) TOPOLOGY:  linear (xi) SEQUENCE DESCRIPTION: SEQ ID NO:11:

TAATCTGTAA GAGCAGATCC                                                        20

(2) INFORMATION FOR SEQ ID NO:12:

(i) SEQUENCE CHARACTERISTICS:
        (A) LENGTH:  20 base pairs
        (B) TYPE:  nucleic acid
        (C) STRANDEDNESS:  single-stranded
        (D) TOPOLOGY:  linear (xi) SEQUENCE DESCRIPTION: SEQ ID NO:12:

TGTTATCACA CTGGTGCTAA                                                        20

(2) INFORMATION FOR SEQ ID NO:13:

(i) SEQUENCE CHARACTERISTICS:
        (A) LENGTH:  23 base pairs
        (B) TYPE:  nucleic acid
        (C) STRANDEDNESS:  single-stranded
        (D) TOPOLOGY:  linear (xi) SEQUENCE DESCRIPTION: SEQ ID NO:13:

AATACCTGTA TTCCTCGCCT GTC                                    23

(2) INFORMATION FOR SEQ ID NO:14:

(i) SEQUENCE CHARACTERISTICS:
        (A) LENGTH: 20 base pairs
        (B) TYPE: nucleic acid
        (C) STRANDEDNESS: single-stranded
        (D) TOPOLOGY: linear (xi) SEQUENCE DESCRIPTION: SEQ ID NO:14:

ATGCCTGGCA CCATTAAAGA                                        20

(2) INFORMATION FOR SEQ ID NO:15:

(i) SEQUENCE CHARACTERISTICS:
        (A) LENGTH: 20 base pairs
        (B) TYPE: nucleic acid
        (C) STRANDEDNESS: single-stranded
        (D) TOPOLOGY: linear (xi) SEQUENCE DESCRIPTION: SEQ ID NO:15:

GCATGCTTTG ATGACGCTTC                                        20

(2) INFORMATION FOR SEQ ID NO:16:

(i) SEQUENCE CHARACTERISTICS:
        (A) LENGTH: 20 base pairs
        (B) TYPE: nucleic acid
        (C) STRANDEDNESS: single-stranded
        (D) TOPOLOGY: linear (xi) SEQUENCE DESCRIPTION: SEQ ID NO:16:

CGGATCTTCT GCTGCCGTCG                                        20

(2) INFORMATION FOR SEQ ID NO:17:

(i) SEQUENCE CHARACTERISTICS:
        (A) LENGTH: 20 base pairs
        (B) TYPE: nucleic acid
        (C) STRANDEDNESS: single-stranded
        (D) TOPOLOGY: linear (xi) SEQUENCE DESCRIPTION: SEQ ID NO:17:

CCTCTGACGT CCATCATCTC                                        20

(2) INFORMATION FOR SEQ ID NO:18:

(i) SEQUENCE CHARACTERISTICS:
        (A) LENGTH: 31 base pairs
        (B) TYPE: nucleic acid
        (C) STRANDEDNESS: single-stranded
        (D) TOPOLOGY: linear (xi) SEQUENCE DESCRIPTION: SEQ ID NO:18:

GAAGTCTGCC GTTACTGCCC TGTGGGGCAA G                           31

(2) INFORMATION FOR SEQ ID NO:19:

(i) SEQUENCE CHARACTERISTICS:
        (A) LENGTH: 26 base pairs
        (B) TYPE: nucleic acid
        (C) STRANDEDNESS: single-stranded
        (D) TOPOLOGY: linear -continued (xi) SEQUENCE DESCRIPTION: SEQ ID NO:19:

CTGCCGTACT GCCCTGTGGG GCAAGG                                    26

(2) INFORMATION FOR SEQ ID NO:20:

(i) SEQUENCE CHARACTERISTICS:
        (A) LENGTH: 26 base pairs
        (B) TYPE: nucleic acid
        (C) STRANDEDNESS: single-stranded
        (D) TOPOLOGY: linear (xi) SEQUENCE DESCRIPTION: SEQ ID NO:20:

ATGCCCTCCC CCATGCCATC CTGCGT                                    26

(2) INFORMATION FOR SEQ ID NO:21:

(i) SEQUENCE CHARACTERISTICS:
        (A) LENGTH: 20 base pairs
        (B) TYPE: nucleic acid
        (C) STRANDEDNESS: single-stranded
        (D) TOPOLOGY: linear (xi) SEQUENCE DESCRIPTION: SEQ ID NO:21:

CAACTTCATC CACGTTCACC                                           20

(2) INFORMATION FOR SEQ ID NO:22:

(i) SEQUENCE CHARACTERISTICS:
        (A) LENGTH: 27 base pairs
        (B) TYPE: nucleic acid
        (C) STRANDEDNESS: single-stranded
        (D) TOPOLOGY: linear (xi) SEQUENCE DESCRIPTION: SEQ ID NO:22:

GTCTGCCGTT ACTGCCCTGT GGGGCAA                                   27

(2) INFORMATION FOR SEQ ID NO:23:

(i) SEQUENCE CHARACTERISTICS:
        (A) LENGTH: 32 base pairs
        (B) TYPE: nucleic acid
        (C) STRANDEDNESS: single-stranded
        (D) TOPOLOGY: linear (xi) SEQUENCE DESCRIPTION: SEQ ID NO:23:

CCTCAAACAG ACACCATGGT GCACCTGACT CC                             32

(2) INFORMATION FOR SEQ ID NO:24:

(i) SEQUENCE CHARACTERISTICS:
        (A) LENGTH: 30 base pairs
        (B) TYPE: nucleic acid
        (C) STRANDEDNESS: single-stranded
        (D) TOPOLOGY: linear (xi) SEQUENCE DESCRIPTION: SEQ ID NO:24:

GAAGTCTGCC GTTACTGCCC TGTGGGGCAA                                30

(2) INFORMATION FOR SEQ ID NO:25:

(i) SEQUENCE CHARACTERISTICS:
        (A) LENGTH: 23 base pairs
        (B) TYPE: nucleic acid
        (C) STRANDEDNESS: single-stranded
        (D) TOPOLOGY: linear

```
        (xi) SEQUENCE DESCRIPTION: SEQ ID NO:25:

TGAAGGAGAA GGTGTCTGCG GGA                                       23

(2) INFORMATION FOR SEQ ID NO:26:

(i) SEQUENCE CHARACTERISTICS:
            (A) LENGTH: 25 base pairs
            (B) TYPE:   nucleic acid
            (C) STRANDEDNESS:  single-stranded
            (D) TOPOLOGY:  linear (xi) SEQUENCE DESCRIPTION: SEQ ID NO:26:

CCTCGGCTAA ATAGTAGTGC GTCGA                                     25

(2) INFORMATION FOR SEQ ID NO:27:

(i) SEQUENCE CHARACTERISTICS:
            (A) LENGTH: 20 base pairs
            (B) TYPE:   nucleic acid
            (C) STRANDEDNESS:  single-stranded
            (D) TOPOLOGY:  linear (xi) SEQUENCE DESCRIPTION: SEQ ID NO:27:

AGGACGGTGC GGTGAGAGTG                                           20
```